US 8,751,200 B2

(12) United States Patent
Takai et al.

(10) Patent No.: US 8,751,200 B2
(45) Date of Patent: Jun. 10, 2014

(54) SIGNAL PROCESSING FOR PREDICTING AN INPUT TIME SERIES SIGNAL AND APPLICATION THEREOF TO PREDICT POSITION OF AN AFFECTED AREA DURING RADIOTHERAPY

(75) Inventors: Yoshihiro Takai, Sendai (JP); Noriyasu Homma, Sendai (JP); Masao Sakai, Sendai (JP)

(73) Assignee: Tohoku University, Sendai-shi, Miyagi (JP)

( * ) Notice: Subject to any disclaimer, the term of this patent is extended or adjusted under 35 U.S.C. 154(b) by 136 days.

(21) Appl. No.: 13/112,361

(22) Filed: May 20, 2011

(65) Prior Publication Data

US 2011/0266464 A1 Nov. 3, 2011

Related U.S. Application Data

(63) Continuation of application No. PCT/JP2009/069992, filed on Nov. 19, 2009.

(30) Foreign Application Priority Data

Nov. 21, 2008 (JP) ................................. 2008-298634

(51) Int. Cl.
*G06F 17/15* (2006.01)
*A61N 5/10* (2006.01)

(52) U.S. Cl.
CPC ............ *G06F 17/153* (2013.01); *A61N 5/1037* (2013.01)
USPC .................................. 703/2; 378/65; 708/426

(58) Field of Classification Search
USPC ........................................................ 378/65
See application file for complete search history.

(56) References Cited

U.S. PATENT DOCUMENTS

| | | | |
|---|---|---|---|
| 6,335,961 B1 * | 1/2002 | Wofford et al. ................. | 378/65 |
| 7,191,100 B2 * | 3/2007 | Mostafavi ..................... | 708/426 |
| 7,570,738 B2 * | 8/2009 | Khamene et al. .............. | 378/65 |
| 7,880,154 B2 * | 2/2011 | Otto ........................... | 250/505.1 |
| 7,902,530 B1 * | 3/2011 | Sahadevan ................. | 250/494.1 |

(Continued)

FOREIGN PATENT DOCUMENTS

| | | |
|---|---|---|
| JP | 2006-051199 A | 2/2006 |
| JP | 2008-514352 A | 5/2008 |

OTHER PUBLICATIONS

Sawant, Amit, et al. "Management of Three-Dimensional Intrafraction Motion Through Real-Time DMLC Tracking" Medical Physics, vol. 35, No. 5, pp. 2050-2061 (Apr. 25, 2008).*

(Continued)

*Primary Examiner* — Kamini S Shah
*Assistant Examiner* — Jay B Hann
(74) *Attorney, Agent, or Firm* — Westerman, Hattori, Daniels & Adrian, LLP

(57) ABSTRACT

A certain component of an input time series signal (hereinafter referred to as input) is assumed as a cycle time-variable time series signal and a prediction model for predicting a value of the input after the predetermined time is produced, and the value of the input after the predetermined time is predicted and outputted using the prediction model.

14 Claims, 31 Drawing Sheets

(56) References Cited

U.S. PATENT DOCUMENTS

| | | | |
|---|---|---|---|
| 7,906,770 B2* | 3/2011 | Otto | 250/492.3 |
| 7,907,987 B2* | 3/2011 | Dempsey | 600/411 |
| 8,027,430 B2* | 9/2011 | Nord et al. | 378/65 |
| 8,229,068 B2* | 7/2012 | Lu et al. | 378/65 |
| 2004/0174949 A1* | 9/2004 | Yamashita et al. | 378/65 |
| 2006/0074292 A1* | 4/2006 | Thomson et al. | 600/411 |
| 2007/0299798 A1* | 12/2007 | Suyama et al. | 706/21 |
| 2008/0031404 A1* | 2/2008 | Khamene et al. | 378/6 |
| 2008/0159478 A1* | 7/2008 | Keall et al. | 378/65 |
| 2009/0034819 A1* | 2/2009 | Nord et al. | 382/132 |
| 2009/0189092 A1* | 7/2009 | Aoi et al. | 250/492.1 |

OTHER PUBLICATIONS

Rüdiger, Heinz, et al. "Trigonometric Regressive Spectral Analysis" Computer Methods and Programs in Biomedicine, vol. 58, pp. 1-15, (1999).*

International Search Report for PCT/JP2009/069992 mailed on Feb. 9, 2010.

Brockwell, Peter J. et al. "Introduction to Time Series and Forecasting." 2002, Second Edition, Springer-Verlag, New York.

Keall, Paul J. et al. "The Management of Respiratory Motion in Radiation Oncology Report of AAPM Task Group 76." Medical Physics, Oct. 2006, pp. 3874-3900, vol. 33, No. 10, American Association of Physicists in Medicine, USA.

* cited by examiner

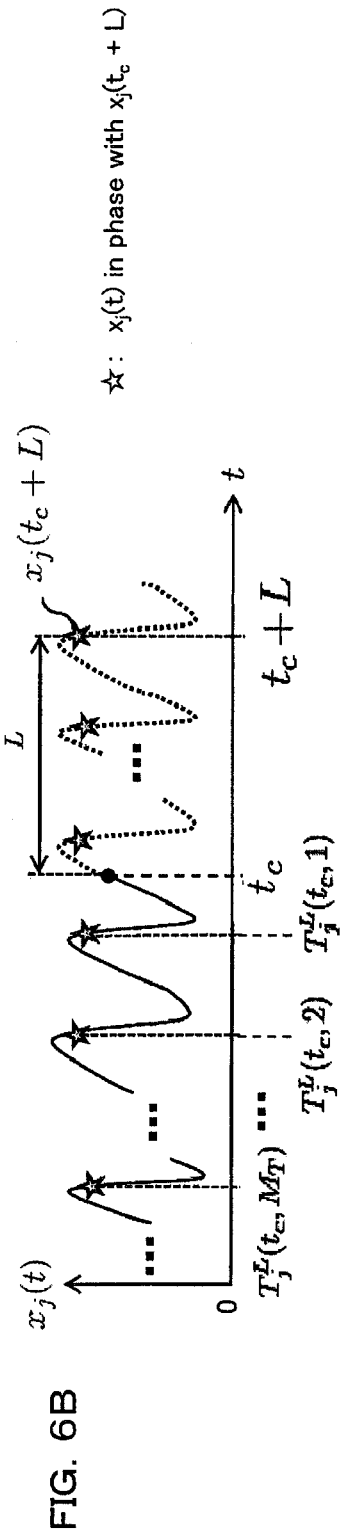

FIG. 7A

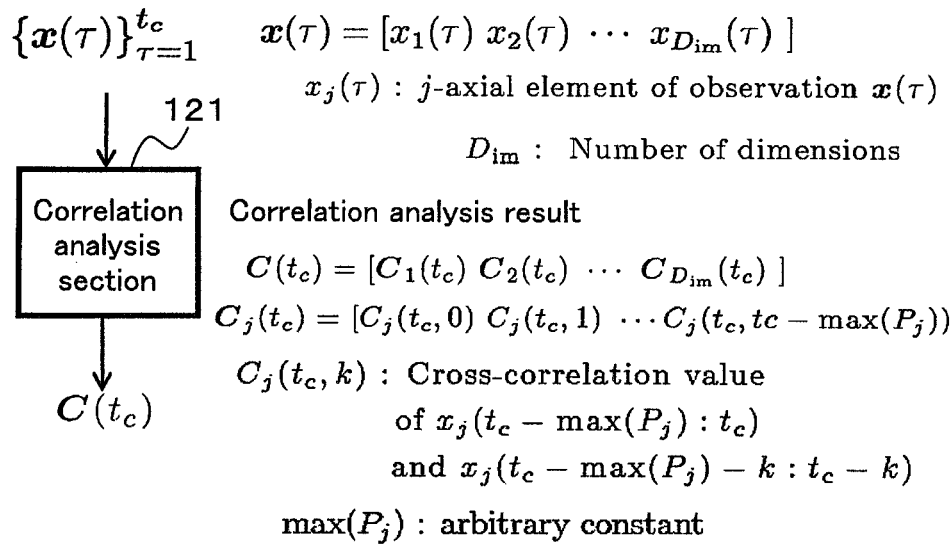

Input time series $\{x(\tau)\}_{\tau=1}^{t_c}$    $x(\tau) = [x_1(\tau)\ x_2(\tau)\ \cdots\ x_{D_{im}}(\tau)]$ $x_j(\tau)$ : $j$-axial element of observation $x(\tau)$ $D_{im}$ : Number of dimensions Correlation analysis result $C(t_c) = [C_1(t_c)\ C_2(t_c)\ \cdots\ C_{D_{im}}(t_c)]$ $C_j(t_c) = [C_j(t_c, 0)\ C_j(t_c, 1)\ \cdots C_j(t_c, tc - \max(P_j))]$ $C_j(t_c, k)$ : Cross-correlation value
of $x_j(t_c - \max(P_j) : t_c)$
and $x_j(t_c - \max(P_j) - k : t_c - k)$ $\max(P_j)$ : arbitrary constant

FIG. 7B

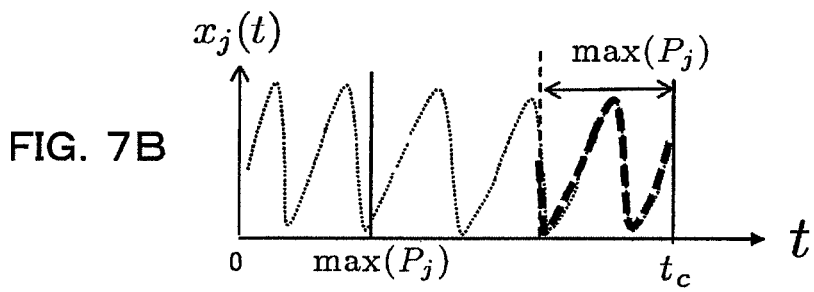

FIG. 7C

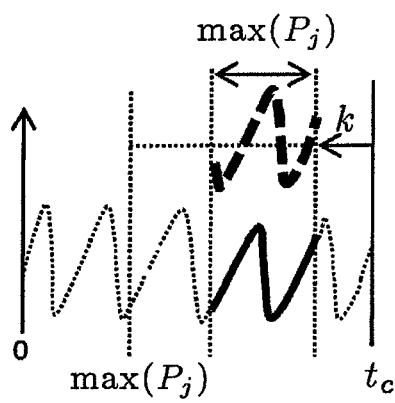

FIG. 7D

Cross-correlation value

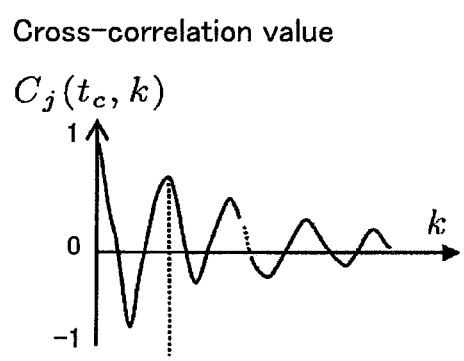

FIG. 8A
Time series of
correlation analysis result
$\{C(\tau)\}_{\tau=1}^{t_c}$

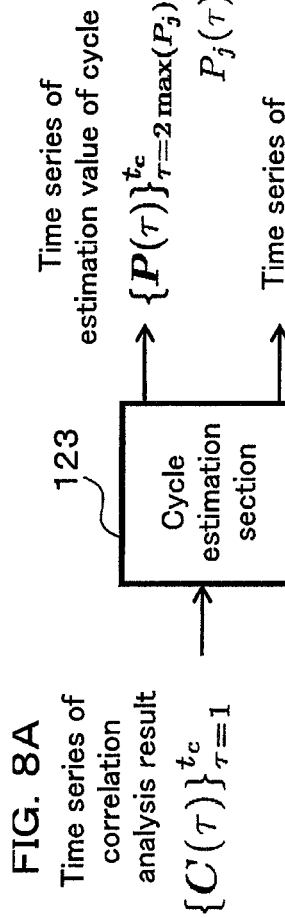

Time series of
estimation value of cycle
$\{P(\tau)\}_{\tau=2\max(P_j)}^{t_c}$   $P(\tau) = [P_1(\tau)\ P_2(\tau)\ \cdots\ P_{D_{im}}(\tau)]$ $P_j(\tau)$ : seasonal dynamics period of $x_j(\tau)$ Time series of
reliability of P($\tau$)   $C_P(\tau) = [C_{P_1}(\tau)\ C_{P_2}(\tau)\ \cdots\ C_{P_{D_{im}}}(\tau)]$
$\{C_P(\tau)\}_{\tau=2\max(P_j)}^{t_c}$   $C_{P_j}(\tau)$ : reliability of $P_j(\tau)$

FIG. 8B

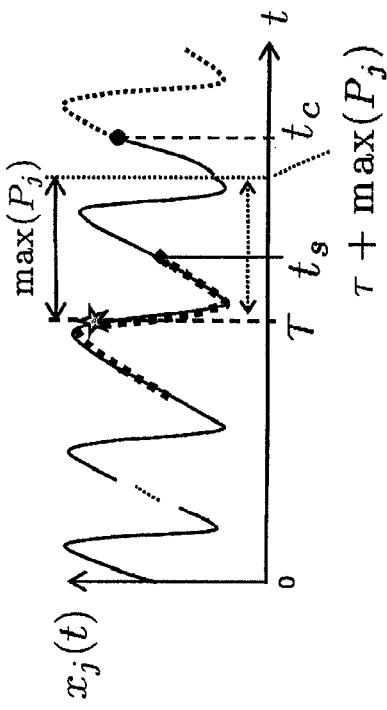

FIG. 8C

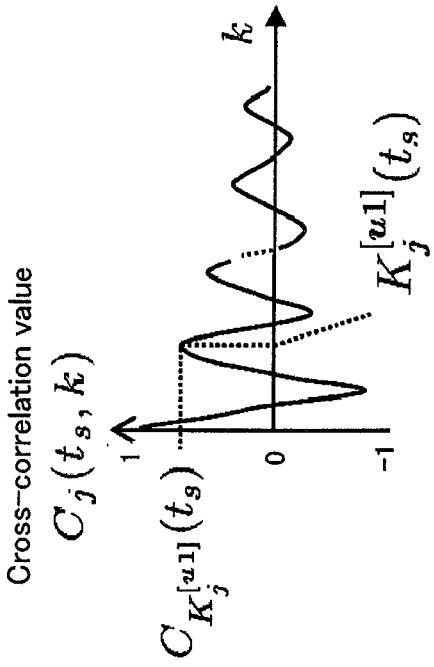

FIG. 10A

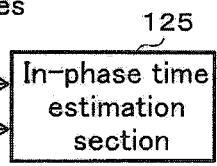

Input time series
$\{x(\tau)\}_{\tau=1}^{t_c}$
$\{C(\tau)\}_{\tau=1}^{t_c}$

Time series of correlation analysis result $\{\tilde{P}(t_c, \tau)\}_{\tau=t_c+1}^{t_c+L}$ 125 In-phase time estimation section Time information in phase with prediction target $x(t_c + L)$ $T^L(t_c) = \begin{bmatrix} T_1^L(t_c) & T_2^L(t_c) & \cdots & T_{D_{im}}^L(t_c) \end{bmatrix}$ $T_j^L(t_c) = \begin{bmatrix} T_j^L(t_c, 1) & T_j^L(t_c, 2) & \cdots & T_j^L(t_c, M_T) \end{bmatrix}^T$ $T_j^L(t_c, i)$ : $i$-th corresponding period times of target dynamics of $x_j(t_c + L)$ Reliability information of time information $T^L(t_c)$ $C_{T^L}(t_c) = \begin{bmatrix} C_{t_1^L}(t_c) & C_{t_2^L}(t_c) & \cdots & C_{t_{D_{im}}^L}(t_c) \end{bmatrix}$ $C_{T_j^L}(t_c) = \begin{bmatrix} C_{T_j^L}(t_c, 1) & C_{T_j^L}(t_c, 2) & \cdots & C_{T_j^L}(t_c, M_T) \end{bmatrix}^T$ $C_{T_j^L}(t_c, i)$ : reliability of $T_j^L(t_c, i)$ $M_T$ : arbitrary constant

FIG. 10B

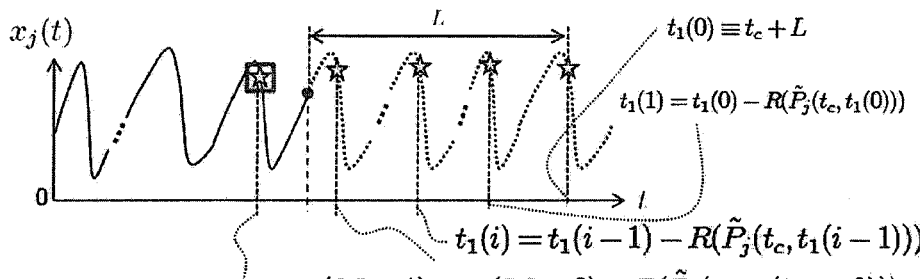

$t_1(0) \equiv t_c + L$
$t_1(1) = t_1(0) - R(\tilde{P}_j(t_c, t_1(0)))$
$t_1(i) = t_1(i-1) - R(\tilde{P}_j(t_c, t_1(i-1)))$
$t_1(M_l - 1) = t_1(M_l - 2) - R(\tilde{P}_j(t_c, t_1(M_l - 2)))$ starting value
$\begin{bmatrix} T_j^L(t_c, 1) = t_1(M_l) = t_1(M_l - 1) - R(\tilde{P}_j(t_c, t_1(M_l - 1))) \\ C_{t_j^L}(t_c, 1) = 1 \end{bmatrix}$

FIG. 10C

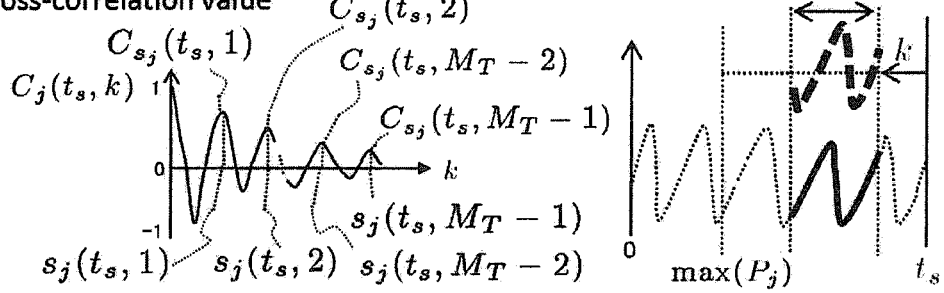

Cross-correlation value

FIG. 10D

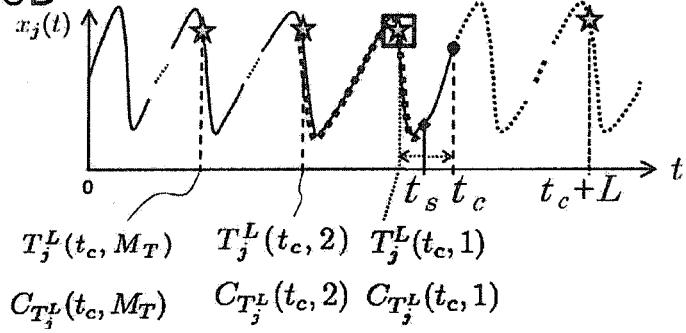

$T_j^L(t_c, M_T) \quad T_j^L(t_c, 2) \quad T_j^L(t_c, 1)$
$C_{T_j^L}(t_c, M_T) \quad C_{T_j^L}(t_c, 2) \quad C_{T_j^L}(t_c, 1)$

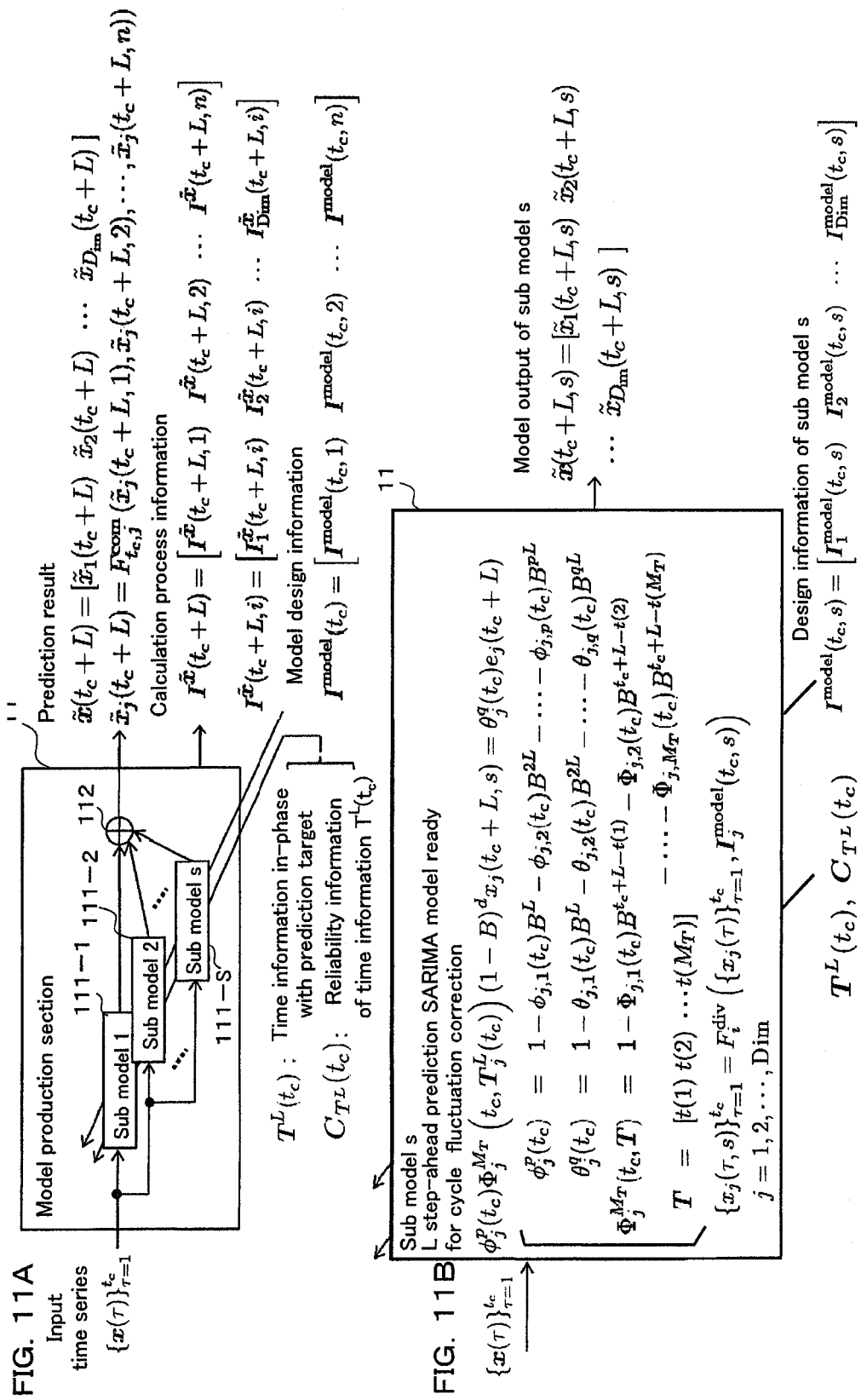

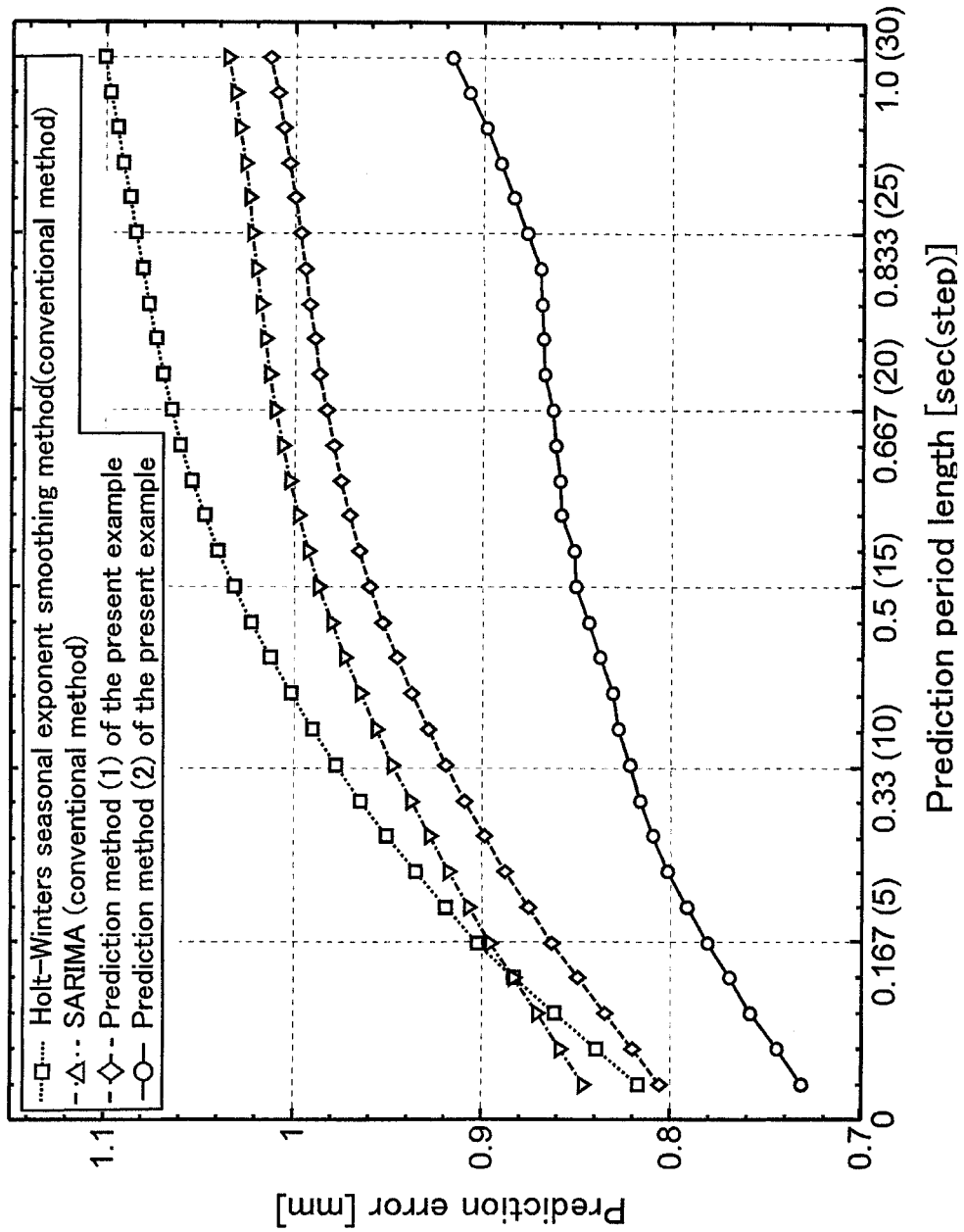

US 8,751,200 B2

SIGNAL PROCESSING FOR PREDICTING AN INPUT TIME SERIES SIGNAL AND APPLICATION THEREOF TO PREDICT POSITION OF AN AFFECTED AREA DURING RADIOTHERAPY

CROSS-REFERENCE TO RELATED APPLICATIONS

This application is a continuation application of a PCT international application No. PCT/JP2009/069992 filed on Nov. 19, 2009 in Japan, and this application is based upon and claims the benefit of priority of the prior Japanese Patent Application No. 2008-298634, filed on Nov. 21, 2008 in Japan, the entire contents of which are incorporated by references.

FIELD

The embodiments discussed herein are related to a signal processing apparatus, a signal processing method, and a signal processing program, a computer-readable recording medium storing the signal processing program, and a radiotherapy apparatus.

BACKGROUND

A radiotherapy apparatus for irradiating a radiation upon an affected area of a patient to perform medical treatment is known.

In the case where a radiation is irradiated upon an affected area of a patient by the radiotherapy apparatus, the position or the shape of the affected area is sometimes fluctuated by breath of the patient, and so on.

In order to irradiate a radiation upon an affected area organization while suppressing an influence of the radiation on a normal organization of the patient, there is a method that the radiation is intermittently irradiated only in the case where an affected area organization is moved to an irradiation position of the radiation.

However, since the time of medical treatment is prolonged by such a method as just described, a heavy burden is imposed on the patient. Further, where the sum total of the energy amount of an irradiated radiation is constant, the effect of medical treatment increases as the irradiation time decreases. Hence, the method described above has the possibility that a biological effect (medical treatment effect) may decrease.

Therefore, another method is known that, by predicting the movement of the affected area position, the irradiation position of a radiation is moved to follow up the affected area position to irradiate a radiation.

It is to be noted that, as an existing technique relating to a radiotherapy apparatus, a method of controlling the irradiation timing for radioscopic image capture and a startup timing of a medical treatment radiation to acquire a radioscopic image in which a subtle shading difference is secured, another method of predicting the most likely certain affected area position at a point of time of medical treatment radiation irradiation based on time series data to accurately and securely irradiate a radiation upon the affected area, and a further method of comparing an acquired radioscopic image of an irradiation target with a reference image regarding a specific evaluation factor to carry out irradiation control with high reliability for an irradiation target and so forth are known.

[Patent Document 1] Japanese Laid-Open Patent Publication No. 2006-51199

In the conventional method described above, for example, prediction is carried out by simply applying an autoregressive model to an input time series signal obtained from an observation signal of an affected area position used as an input. Such prediction as just described is used, for example, when the affected area position after a very short period of time (for example, approximately 0.15 seconds) is predicted.

Further, in the method described above, in order to move the irradiation position of a radiation to follow up the affected area position, for example, the shape and the size of a passage window of a collimator for forming an irradiation range of a radiation are controlled.

However, there is the possibility that, if the time required for control of a collimator becomes long, then the shape and the size of the collimator cannot be controlled to the desired shape and size within a period of prediction time assumed for an autoregressive model, and as a result, irradiation following up the movement of an affected area position cannot be implemented.

SUMMARY (1) According to an aspect of the embodiments, an apparatus includes a signal processing apparatus including: a cycle fluctuation analysis section adapted to assume a certain component of an input time series signal as a time series signal whose cycle varies with respect to time to carry out a correlation analysis between part of the input time series signal and the input time series signal, estimate a cycle fluctuation of the input time series signal and reliability of the cycle fluctuation using a result of the correlation analysis, predict a cycle of the input time series signal after predetermined time using the cycle fluctuation and the reliability of the cycle fluctuation and calculate, using the result of the correlation analysis and the predicted cycle, in-phase time information which represents time of the input time series signal whose phase becomes same as a phase of the input time series signal after the predetermined time and the reliability of the in-phase time information, a prediction accuracy estimation section adapted to estimate model design information for predicting a value of the input time series signal after the predetermined time and accuracy of the prediction of the value of the input time series signal after the predetermined time based on the model design information using the input time series signal, the time series information of a variation per unit time of the input time series signal and the in-phase time information and reliability of the in-phase time information calculated by the cycle fluctuation analysis section, and a model production section adapted to produce, using the input time series signal, the in-phase time information and the reliability of the in-phase time information calculated by the cycle fluctuation analysis section and the model design information estimated by the prediction accuracy estimation section, a prediction model for predicting the value of the input time series signal after the predetermined time and predict and output the value of the input time series signal after the predetermined time using the prediction model.

(2) The prediction accuracy estimation section may estimate the model design information using information outputted from the model production section regarding a calculation process of the value of the input time series signal after the predetermined time.

(3) The cycle fluctuation analysis section may include a correlation analysis section for carrying out a correlation analysis between part of the input time series signal and the input time series signal, a cycle estimation section for estimating the cycle fluctuation and the reliability of the cycle fluctuation using a result of the analysis by the correlation analysis section, a cycle prediction section for predicting a cycle of the input time series signal after the predetermined time using the cycle fluctuation and the reliability of the cycle fluctuation estimated by the cycle estimation section, and an in-phase time estimation section for estimating the in-phase time information and reliability of the in-phase time information using a result of the correlation analysis by the correlation analysis section and the cycle predicted by the cycle prediction section.

(4) Further, the model production section may produce the prediction model using a plurality of sub models whose structures or characteristics are different from each other.

(5) The plurality of sub models may include at least one of a SARIMA (Seasonal Auto-Regressive Integrated Moving Average) model, a seasonal adjustment index smoothing method model, a non-linear ARIMA (Auto-Regressive Integrated Moving Average) model and a soft computing model such as a neural network, fuzzy or the like.

(6) Further, the model production section may change the sub models using the accuracy of the prediction of the value of the input time series signal after the predetermined time estimated by the prediction accuracy estimation section.

(7) According to an aspect of the embodiments, a method includes a signal processing method including: assuming a certain component of an input time series signal as a time series signal whose cycle varies with respect to time to carry out a correlation analysis between part of the input time series signal and the input time series signal, estimating a cycle fluctuation of the input time series signal and reliability of the cycle fluctuation using a result of the correlation analysis, predicting a cycle of the input time series signal after predetermined time using the cycle fluctuation and the reliability of the cycle fluctuation and calculating, using the result of the correlation analysis and the predicted cycle, in-phase time information which represents time of the input time series signal whose phase becomes same as a phase of the input time series signal after the predetermined time and the reliability of the in-phase time information, estimating model design information for predicting a value of the input time series signal after the predetermined time and accuracy of the prediction of the value of the input time series signal after the predetermined time based on the model design information using the input time series signal, the time series information of a variation per unit time of the input time series signal and the calculated in-phase time information and reliability of the in-phase time information, and producing, using the input time series signal, the calculated in-phase time information and reliability of the in-phase time information and the estimated model design information, a prediction model for predicting the value of the input time series signal after the predetermined time and predicting and outputting the value of the input time series signal after the predetermined time using the prediction model.

(8) According to an aspect of the embodiments, an apparatus includes a radiotherapy apparatus for irradiating a radiation on an affected area of a patient, the radiotherapy apparatus including: a radiation generation section adapted to generate the radiation, a collimator section adapted to form an irradiation range of the radiation generated from the radiation generation section into a desired shape, a measurement section adapted to measure a position of the affected area, the signal processing apparatus described above adapted to estimate prediction of a position of the affected area after predetermined time and accuracy information of the prediction position using an input time series signal regarding the position of the affected area measured by the measurement section, and a driving controlling section adapted to calculate, using the position of the affected area after the predetermined time and the accuracy information predicted by the signal processing apparatus, an irradiation position and an irradiation range of the radiation and control and drive the collimator section based on a result of the calculation.

(9) The radiotherapy apparatus may further include a timing controlling section adapted to control a generation timing of the radiation by the radiation generation section using the position of the affected area after the predetermined time and the accuracy information predicted by the signal processing apparatus.

(10) According to an aspect of the embodiments, an apparatus includes a radiotherapy apparatus for irradiating a radiation on an affected area of a patient, the radiotherapy apparatus including: a radiation generation section adapted to generate the radiation, a measurement section adapted to measure a position of the affected area, the signal processing apparatus described above adapted to estimate prediction of a position of the affected area after predetermined time and accuracy information of the predicted position using an input time series signal regarding the position of the affected area measured by the measurement section, and a controlling section adapted to control an irradiation timing of the radiation by the radiation generation section using the position of the affected area after the predetermined time and the accuracy information predicted by the signal processing apparatus.

(11) According to an aspect of the embodiments, a program includes a signal processing program for causing, in a signal processing apparatus for predicting a value of an input time series signal after predetermined time, a computer to implement a prediction function, the signal processing program causing a computer to implement a cycle fluctuation analysis function for assuming a certain component of an input time series signal as a time series signal whose cycle varies with respect to time to carry out a correlation analysis between part of the input time series signal and the input time series signal, estimating a cycle fluctuation of the input time series signal and reliability of the cycle fluctuation using a result of the correlation analysis, predicting a cycle of the input time series signal after predetermined time using the cycle fluctuation and the reliability of the cycle fluctuation and calculating, using the result of the correlation analysis and the predicted cycle, in-phase time information which represents time of the input time series signal whose phase becomes same as a phase of the input time series signal after the predetermined time and the reliability of the in-phase time information, a prediction accuracy estimation function for estimating model design information for predicting a value of the input time series signal after the predetermined time and accuracy of the prediction of the value of the input time series signal after the predetermined time based on the model design information using the input time series signal, the time series information of a variation per unit time of the input time series signal and the in-phase time information and reliability of the in-phase time information calculated by the cycle fluctuation analysis function, and a model production function for producing, using the input time series signal, the in-phase time information and the reliability of the in-phase time information calculated by the cycle fluctuation analysis function and the model design information estimated by the prediction accuracy estimation function, a prediction model for predicting the value of the input time series signal after the predetermined time and predicting and outputting the value of the input time series signal after the predetermined time using the prediction model.

(12) According to an aspect of the embodiments, a medium includes a computer-readable recording medium storing a signal processing program for causing, in a signal processing apparatus for predicting a value of an input time series signal after predetermined time, a computer to implement a prediction function is recorded, the signal processing program causing the computer to implement a cycle fluctuation analysis function for assuming a certain component of an input time series signal as a time series signal whose cycle varies with respect to time to carry out a correlation analysis between part of the input time series signal and the input time series signal, estimating a cycle fluctuation of the input time series signal and reliability of the cycle fluctuation using a result of the correlation analysis, predicting a cycle of the input time series signal after predetermined time using the cycle fluctuation and the reliability of the cycle fluctuation and calculating, using the result of the correlation analysis and the predicted cycle, in-phase time information which represents time of the input time series signal whose phase becomes same as a phase of the input time series signal after the predetermined time and the reliability of the in-phase time information, a prediction accuracy estimation function for estimating model design information for predicting a value of the input time series signal after the predetermined time and accuracy of the prediction of the value of the input time series signal after the predetermined time based on the model design information using the input time series signal, the time series information of a variation per unit time of the input time series signal and the in-phase time information and reliability of the in-phase time information calculated by the cycle fluctuation analysis function, and a model production function for producing, using the input time series signal, the in-phase time information and the reliability of the in-phase time information calculated by the cycle fluctuation analysis function and the model design information estimated by the prediction accuracy estimation function, a prediction model for predicting the value of the input time series signal after the predetermined time and predicting and outputting the value of the input time series signal after the predetermined time using the prediction model.

The object and advantages of the embodiment will be realized and attained by means of the elements and combinations particularly pointed out in the claims.

It is to be understood that both the foregoing general description and the following detailed description are exemplary and explanatory and are not restrictive of the embodiment, as claimed.

BRIEF DESCRIPTION OF THE DRAWINGS

FIGS. 6A to 6C are views illustrating an example of operation of a cycle fluctuation analysis section 12;

FIGS. 7A to 7D are views illustrating an example of operation of a correlation analysis section 121;

FIGS. 8A to 8C are views illustrating an example of operation of a cycle estimation section 123;

FIGS. 10A to 10D are views illustrating an example of operation of an in-phase time estimation section 125;

FIGS. 11A and 11B are views illustrating an example of operation of a model production section 11;

FIG. 31 is a view illustrating an example of a comparison result between the prediction method of the present example and the conventional prediction method.

DESCRIPTION OF EMBODIMENTS

Hereinafter, description will now be made in relation to an embodiment with reference to accompanying drawings. However, the embodiment to be detailed below is merely example, so there is no intention of excluding another embodiments and variations and application of techniques that are not mentioned in this specification. In other words, various changes and modifications (e.g., combination of the embodiments and the modifications) can be suggested without departing from the spirit the embodiment.

[1] First Embodiment (1.1) Apparatus Outline

Figure 1:
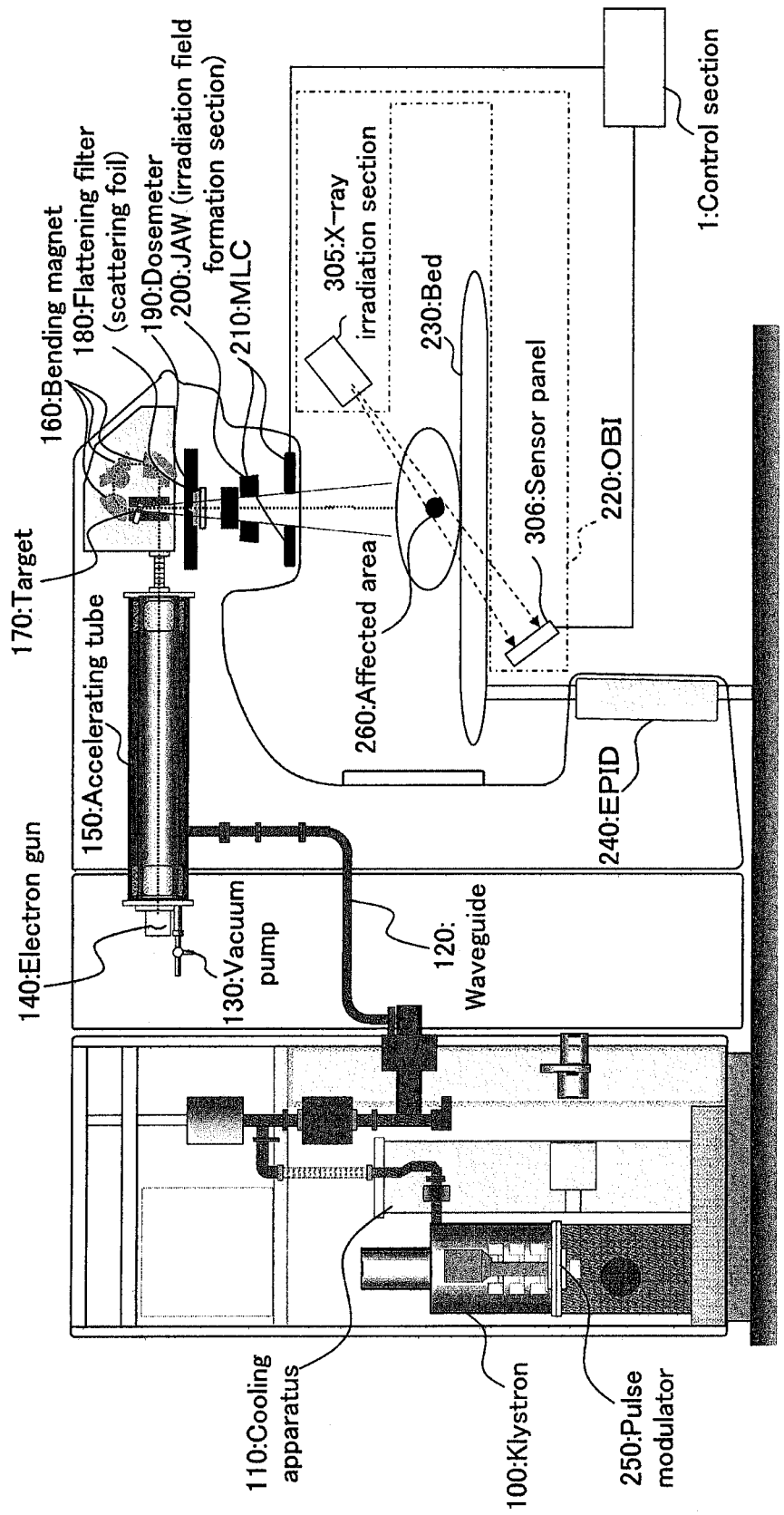
FIG. 1 is a view illustrating an outline of a radiotherapy apparatus.

An outline of a radiotherapy apparatus is illustrated in FIG. 1. The radiotherapy apparatus illustrated in FIG. 1 includes, for example, a control section 1, a klystron 100, a cooling apparatus 110, a waveguide 120, a vacuum pump 130, an electrons gun 140, an accelerating tube 150, a bending magnet 160, a target 170 and a smoothing filter (scattering filter) 180. Further, the radiotherapy apparatus illustrated in FIG. 1 includes, for example, a dosemeter 190, an irradiation field formation section (JAW) 200, an MLC (Multi Leaf Collimator) 210, an OBI (On-Board Imager) 220, a bed 230, an EPID (Electronic Portal Imaging Device) 240 and a pulse modulator 250.

In the present embodiment, for example, the control section 1 predicts position information of an affected area 260 after predetermined time from position information (a position, a shape, a size and so forth) of the affected portion 260 measured by the OBI 220. Then, the control section 1 drives and controls, for example, the MLC 210 based on a result of the prediction to implement radiation irradiation in response to the position, shape, size and so forth of the affected area 260 after the predetermined time.

Figure 2:
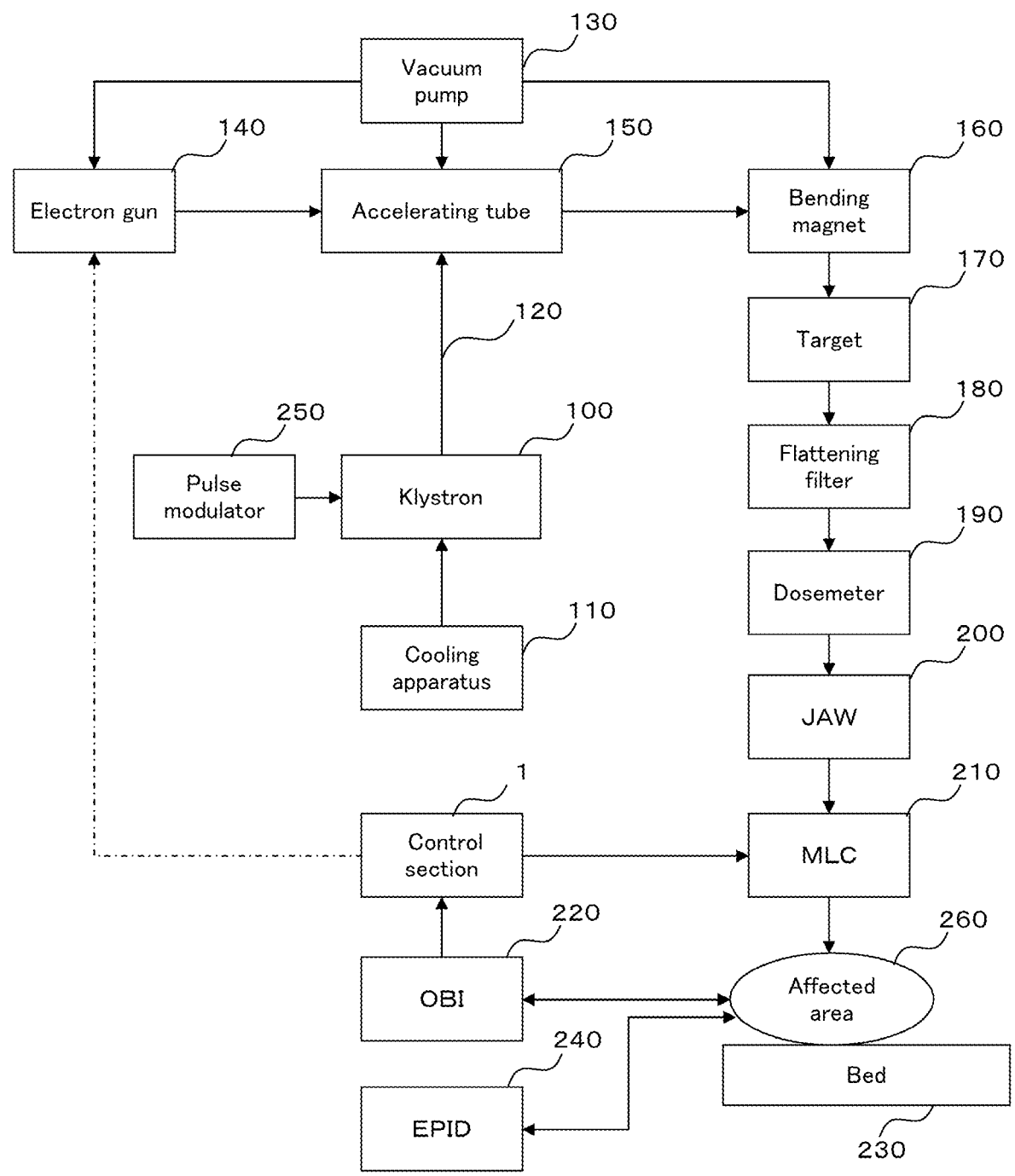
FIG. 2 is a functional block diagram of the radiotherapy apparatus illustrated in FIG. 1.

To this end, the radiotherapy apparatus illustrated in FIG. 1 includes functional blocks illustrated in FIG. 2.

Here, the pulse modulator 250 is a voltage generator for generating a pulse voltage. The pulse modulator 250 in the present embodiment generates a predetermined pulse voltage taking, for example, an input of a trigger pulse from a trigger pulse generator (not illustrated) as an opportunity.

The klystron 100 is an electronic tube for utilizing an interaction between electron beam and a high frequency wave to amplify the high frequency wave to output a microwave having high power. The klystron 100 of the present example generates electron beam, for example, in response to the pulse voltage received from the pulse modulator 250 and carries out speed modulation for the electron beam and then outputs the electron beam from a gap so that microwave pulse power to be used as energy for accelerating electrons in the accelerating tube 150 is outputted.

The cooling apparatus 110 includes a function for cooling the klystron 100. As a cooling method, for example, a method is available in which a cavity is provided between an armor section which covers a main body section of the klystron 100 and the main body section and cooling water is supplied to the cavity to carry out cooling.

The waveguide 120 transmits microwave pulse power outputted from the klystron 100 to the accelerating tube 150. For example, while a hollow waveguide can be used for the waveguide 120, also a coaxial cable for which a dielectric such as Teflon (registered trademark) is used can be used.

The vacuum pump 130 is a pump for exhausting gas from the inside of a container to form a vacuum state. In the present example, for example, the vacuum state is formed in the proximity of electron beam emitting portion of the electron gun 140, in an internal space of the accelerating tube 150 and in the proximity of the bending magnet 160. By maintaining the portions just described in the vacuum state, loss of microwave pulse power outputted from the klystron 100 and energy loss of an electron beam emitted from the electron gun 140 can be reduced. It is to be noted that, for example, while a dry pump whose degree of erosion to the inside of the accelerating tube 150 or the like is low can be used for the vacuum pump 130, also a wet pump for which oil is used can be used.

The electron gun 140 extracts free electrons from a predetermined metal material or the like to emit an electron beam. For example, electrons in a solid body are discharged into a space by high heat or a high electric field and the discharged electrons are accelerated by applying an electric field thereto, and the electron beam is converged into a beam by an electron lens and then the converged beam is irradiated. For example, while an electric field emission type electron gun for extracting electrons to a space by a quantum-mechanical tunnel effect can be used for the electron gun 140, also a thermoelectric emission type electron gun for carrying out electron emission by thermal energy or the like can be used.

The accelerating tube 150 amplifies the energy of the electron beam emitted from the electron gun 140 using the microwave pulse power outputted from the klystron 100 and transmitted thereto through the waveguide 120. The electron beam is accelerated by the microwave pulse power and is emitted from the accelerating tube 150.

The bending magnet 160 generates a magnetic field in a predetermined direction to correct the orbit of the electron beam emitted from the accelerating tube 150. The bending magnet 160 of the present example exemplarily uses three bending magnets 160 to correct the orbit of the electron beam, for example, in order to irradiate the electron beam upon the target 170. It is to be noted that the number of the bending magnets 160 is not limited to that of the example illustrated in FIG. 1.

The target 170 is a material for irradiating a radiation by being irradiated by an electron beam.

For example, tungsten (Tg) can be used for the target 170. It is to be noted that a different material may be used if it is a material capable of generating a radiation when it is irradiated by an accelerated electron beam.

In particular, the pulse modulator 250, klystron 100, cooling apparatus 110, waveguide 120, vacuum pump 130, electron gun 140, accelerating tube 150, bending magnet 160 and target 170 function as an example of a radiation generation section for generating a radiation.

The smoothing filter 180 is a filter for attenuating and smoothing the dose distribution of a radiation irradiated from the target 170. For example, the smoothing filter 180 of the present example attenuates the dose level of the radiation irradiated from the target 170 in accordance with the wavelength to control the dose level of the radiation to a predetermined level (for example, a dose level capable of being irradiated on a human body).

The dosemeter 190 measures the dose level of the radiation. For example, by the dosemeter 190 of the present example, it can be measured and confirmed whether or not the dose level of the radiation after passing through the smoothing filter 180 is attenuated to a predetermined level. Where the dose level of the radiation is not attenuated to the predetermined level, the dose level can be adjusted, for example, by controlling the microwave pulse power in the klystron 100 or the like.

The JAW 200 is an irradiation field formation member formed from a material for blocking a radiation. The JAW 200 is configured, for example, from a plurality of plate-like members, and, by determining the position of the plate members, part of the radiation irradiated from the target 170 is passed while the other part of the radiation is blocked so that an irradiation field of the radiation is formed roughly. For example, the irradiation field of the radiation can be adjusted such that the radiation falls within a range within which it can be inputted to the MLC 210 positioned at the following stage to the JAW 200.

The MLC (collimator section) 210 forms the irradiation range of the radiation irradiated from the target 170 into a desired shape. For example, the MLC 210 in the present embodiment can vary the irradiation range of the radiation after passing through the JAW 200 in response to the position of the affected area 260 after the predetermined time predicted by the control section 1 and prediction accuracy information.

Figure 3:
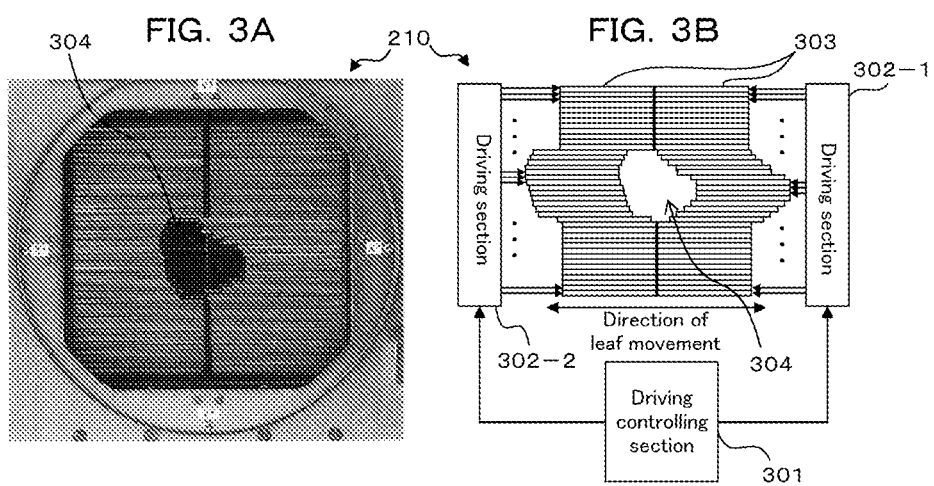
FIG. 3A is a view illustrating an appearance of an MLC 210.
FIG. 3B is a view illustrating an example of a configuration of the MLC 210.

An example of an appearance and a configuration of the MLC 210 are illustrated in FIGS. 3A and 3B.

As illustrated in FIG. 3A, the MLC 210 is configured including, for example, a plurality of pairs of plate-like members (leafs) which block a radiation. By displacing the leaves in a leftward and rightward direction in the plane of the figure independently of each other, the leaves cooperate with each other to form the radiation irradiation field (central blank portion in FIG. 3A) in a desired shape. The radiation passing through the JAW 200 passes through the MLC 210 in the figure-plane leftward and rightward direction so that the radiation can be irradiated on the affected area 260 within a range conforming to the shape of a radiation irradiation field 304.

Here, as illustrated in FIG. 3B, the MLC 210 includes a plurality of leaves 303, driving sections 302-1 and 302-2 and a driving controlling section 301.

Each of the leaves 303 is a plate-like member capable of blocking a radiation. In the present example, for example, two leaves 303 opposed to each other are paired with each other, and a plurality of leaf pairs are formed. The leaves 303 are driven independently of each other by the driving sections 302-1 and 302-2. It is to be noted that the number of the leaves 303 is not limited to that of the illustrated example.

The driving sections 302-1 and 302-2 displace the leaves 303 independently of each other. For example, the driving sections 302-1 and 302-2 drive the leaves 303 by means of a motor provided individually for the leaves 303 so that the leaves 303 are displaced along a leaf moving direction in FIG. 3B. In the example illustrated in FIG. 3B, the leaves 303 on the right side of the plane of the figure are driven by the driving section 302-1 and the leaves 303 on the left side of the plane of the figure are driven by the driving section 302-2. Further, for example, the leaves 303 can be displaced also in an interlocking relationship with each other by the driving sections 302-1 and 302-2. For example, using displacement of a leaf 303 as a trigger, the leaves 303 around the leaf may be displaced in an interlocking relationship with each other.

The driving controlling section 301 controls the driving sections 302-1 and 302-2 to determine individual positions of the leaves 303. Positioning control is carried out for the leaves 303 independently of each other to individual desired positions so that a radiation irradiation field 304 having a desired shape is formed.

For example, based on a result of the prediction (the prediction position of the affected area 260 after the predetermined time and the prediction accuracy information) by the control section 1, the driving controlling section 301 of the present example controls the driving sections 302-1 and 302-2 to determine the positions of the leaves 303. Consequently, since the radiation irradiation field 304 having a desired shape can be formed in response to the position, shape and size of the affected area 260 after the predetermined time predicted by the control section 1, radiation irradiation suitable for the prediction position, shape, size and so forth of the affected area 260 can be implemented.

The OBI (measurement section) 220 measures the position of the affected area 260. For example, an X-ray can be irradiated on a measurement target so that position information regarding a position, a shape, a size and so forth of the measurement target can be outputted.

The OBI 220 of the present example calculates observation values (actual measurement values) of a position, a shape, a size and so forth of the affected area 260, for example, based on plural pieces of position information obtained by irradiating an X-ray from various angles on the affected area 260 of a patient. The position information regarding the position, shape, size and so forth of the affected area 260 actually measured by the OBI 220 is inputted to the control section 1 and is used for a prediction process hereinafter described.

Figure 4:
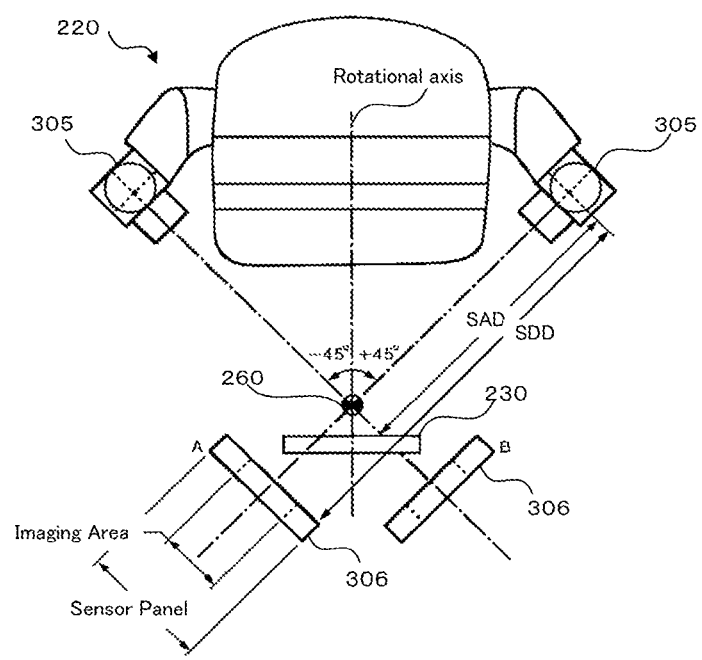
FIG. 4 is a view illustrating an example of a configuration of an OBI 220.

Here, an example of a configuration of the OBI 220 is illustrated in FIG. 4. As illustrated in FIG. 4, the OBI 220 includes, for example, an X-ray irradiation section 305 and a sensor panel 306.

The X-ray irradiation section 305 irradiates an X-ray on the affected area 260 of a patient on the bed 230. It is to be noted that the X-ray is a kind of a radiation and is an electromagnetic wave whose wavelength is approximately 1 pm to 10 nm.

The sensor panel 306 includes a sensor for detecting an X-ray at the surface thereof and outputs a position coordinate of the irradiated X-ray. For example, the sensor panel 306 in the present embodiment receives the X-ray after passing through the affected area 260 in an imaging region (Imaging Area) and calculates and outputs a two-dimensional coordinate of the reception position.

The X-ray irradiation section 305 and the sensor panel 306 are configured such that they can integrally rotate around the center provided by a rotational axis in FIG. 4, and the sensor panel 306 in the present embodiment calculates a three-dimensional coordinate P(X, Y, Z) of the affected area 260, for example, based on a two-dimensional coordinate P1 (x1, y1) of the affected area 260 calculated at a position (position at which an X-ray irradiation axis and the rotational axis form an angle of +45°) indicated by reference character A in FIG. 4 and a two-dimensional coordinate P2(x2, y2) of the affected area 260 calculated at a position (position at which the X-ray irradiation axis and the rotational axis form an angle of −45°) denoted by reference character B in FIG. 4.

For example, where the distance from an irradiation point of the X-ray irradiation section 305 to the affected area 260 is represented as an SAD (source-axis distance) and the distance from the X-ray irradiation point of the X-ray irradiation section 305 to the surface of the sensor panel 306 is represented as an SDD (source-detector distance), the position coordinate P(X, Y, Z) of the affected area 260 is represented by the following expression (1).

[Expression 1]

$$\left. \begin{array}{l} X = x1y2*SAD/(SDD*y1+x1y2) \\ Y = y1x2*SAD/(SDD*y2+y1y2) \\ Z = y1y2*SAD/(SDD*y1+x1y2) \end{array} \right\} \quad (1)$$

The three-dimensional coordinate P(X, Y, Z) of the affected area 260 calculated by the expression (1) given described is inputted, for example, as an actual measurement value (input signal) which indicates the present position of the affected area 260 to the control section 1, and the control section 1 can predict the three-dimensional coordinate of the affected area 260 after the predetermined time using time series information of the actual measurement value.

The bed 230 is an equipment for supporting a patient so that the affected area 260 is placed at a position and a height suitable for radiation irradiation. To this end, the bed 230 in the present embodiment is configured, for example, from a supporting section whose position and height can be adjusted, and a mat section.

The EPID 240 visualizes the position, shape and size of the affected area 260. For example, the position and the height of the bed 230 or the like are determined by the operator based on the visualized shape and so forth of the affected area 260.

The control section 1 carries out prediction of a position coordinate of the affected area 260 after the predetermined time and supposition of the prediction accuracy information using time series information of the position coordinate P(X, Y, Z) of the affected area 260 obtained by the OBI 220. Further, various controls are carried out using a result of the prediction and the prediction accuracy information. For example, the control section 1 of the present example controls the MLC 210 using the prediction result and the prediction accuracy information to form the radiation irradiation field 304 into a shape corresponding to the position, prediction accuracy information, size, shape and so forth of the affected area 260 after the predetermined time. Consequently, since prediction control for the MLC 210 can be carried out before time required for physical driving (positioning) control of the MLC 210, radiation irradiation can be carried out following up the position of the affected area 260.

In particular, the control section 1 of the present example functions as an example of a signal processing apparatus for predicting the position of the affected area 260 after the predetermined time and the prediction accuracy information using the time series information of the position of the affected area 260 measured by the OBI 220. Further, the control section 1 functions as an example of a driving controlling section for calculating an irradiation position and an irradiation range of a radiation using the predicted position of the affected area 260 after the predetermined time and the accuracy information of the prediction position and driving and controlling the MLC 210 based on a result of the calculation.

Further, the control section 1 may carryout not only the driving control of the MLC 210 but also control of the irradiation timing of a radiation using the predicted position of the affected area 260 after the predetermined time and the prediction accuracy information. For example, the control section 1 may control the emission timing of an electron beam from the electron gun 140 thereby to control the generation timing of the radiation, or may control the microwave power amount to be outputted from the klystron 100 thereby to control the generation timing of the radiation in the target 170.

In particular, the control section 1 of the present example functions as an example of a timing controlling section for controlling the generation timing of the radiation using the position of the affected area 260 after the predetermined time and the accuracy information of the prediction position predicted by the method described above.

It is to be noted that the control section 1 may carry out only one of the driving control and the timing control. For example, where the control section 1 carries out only the timing control, since the irradiation position of the radiation is fixed and the radiation is irradiated aiming at a timing at which the affected area 260 moves to the irradiation position based on the prediction result described above, an effect similar to that in the example described above is obtained. Further, since the MLC 210 may not be provided, the apparatus can be simplified and the cost of the apparatus can be decreased.

An example of a configuration of and a prediction method by the control section 1 are described below.

(1.2) Control Section 1

The control section 1 receives an arbitrary time series signal whose principal component is cycle time-variable season dynamics (periodically repeated time series signal) as an input and outputs a prediction value after predetermined time passes and information (prediction accuracy information) regarding the prediction accuracy.

Figure 5:
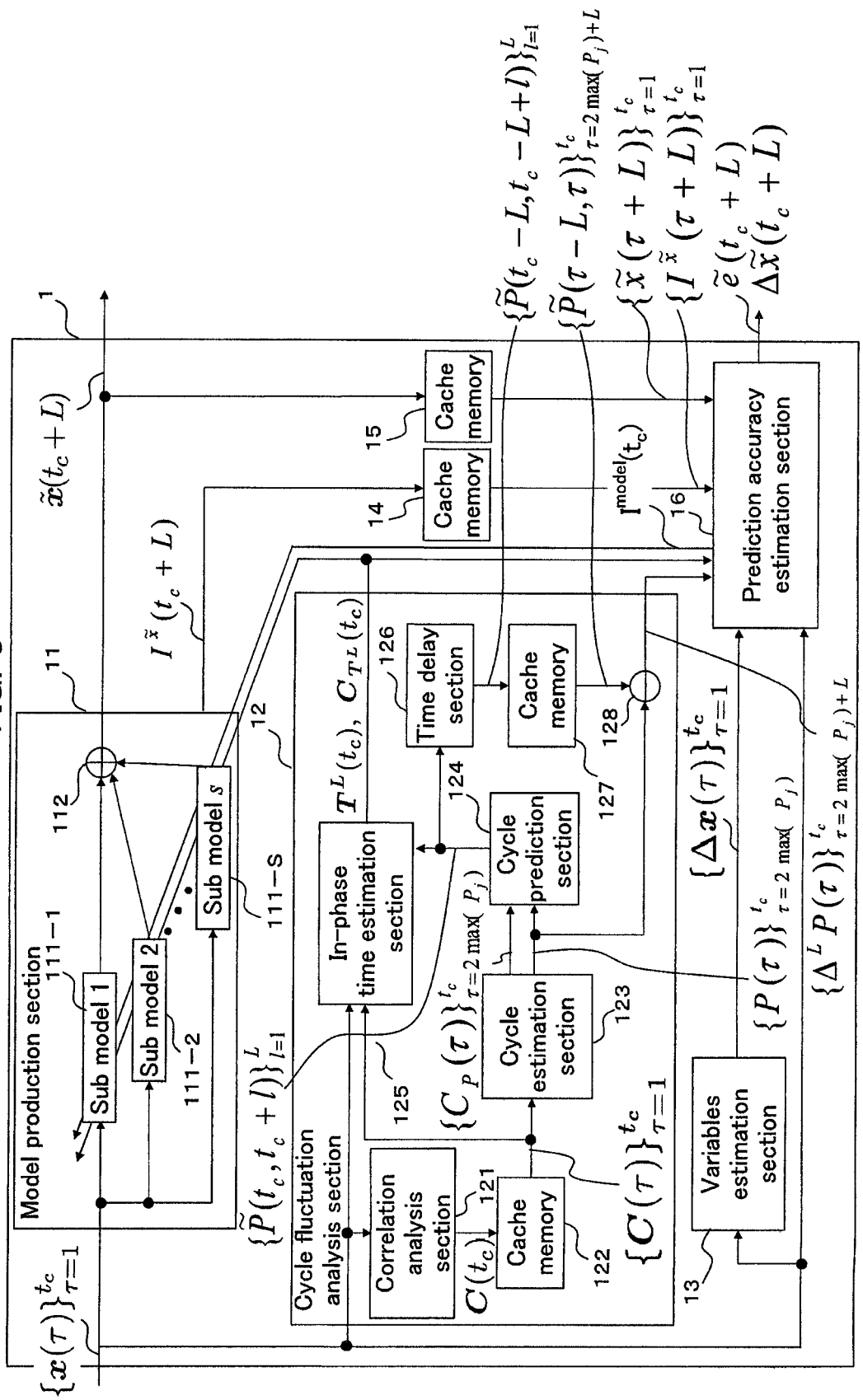
FIG. 5 is a view illustrating an example of a configuration of a control section 1.

The control section 1 illustrated in FIG. 5 includes a model production section 11, a cycle fluctuation analysis section 12, a variables estimation section 13, a cache memory 14, another cache memory 15 and a prediction accuracy estimation section 16.

Here, the input to the control section 1 is a time series signal $$\{x(\tau)\}_{\tau=1}^{t_c}$$

corresponding to a variation of the position of the affected area 260 after the observation starting time to current time $t_c$. Here, $$x(\tau)=[x_1(\tau)x_2(\tau)\ldots x_{Dim}(\tau)] \quad \text{[Expression 2]}$$

is satisfied, and $$x_j(\tau)$$

is the position of the affected area in a jth (j=1 to Dim) dimension direction at time $\tau$, and Dim is a dimension number of the position information.

On the other hand, outputs of the control section 1 are a prediction value $$x(t_c+L) \quad \text{[Expression 3]}$$

of the position $$\tilde{x}(t_c+L)=[\tilde{x}_1(t_c+L)\tilde{x}_2(t_c+L)\ldots \tilde{x}_{D_{im}}(t_c+L)]$$

of the affected area 260 at prediction target time $(t_c+L)$ where an arbitrary prediction period is represented by L, an estimation value $$\tilde{e}(t_c+L)=[\tilde{e}_1(t_c+L)\tilde{e}_2(t_c+L)\ldots \tilde{e}_{D_{im}}(t_c+L)] \quad \text{[Expression 4]}$$

of an error which is accuracy information of the prediction value, and an estimation value $$\Delta\tilde{x}(t_c+L)=[\Delta\tilde{x}_1(t_c+L)\Delta\tilde{x}_2(t_c+L)\ldots \Delta\tilde{x}_{D_{im}}(t_c+L)] \quad \text{[Expression 5]}$$

of a position fluctuation amount per unit time.

(1.3) Model Production Section 11

The model production section 11 produces a prediction model using the time series signal described above which is an input to the control section 1, in-phase time information which has a phase same as that of the prediction target time and which is part of an output of the cycle fluctuation analysis section 12, reliability of the in-phase time information, and model design information which is part of an output of the prediction accuracy estimation section 16, and outputs a prediction value of the input time series signal after the predetermined time passes and detailed information of the procedure in which the prediction value is calculated using the produced prediction model. It is to be noted that the model production section 11 may produce a plurality of sub models in which kinds of filters and models or parameter values are different from each other with an influence of the cycle time variation into consideration and synthesize the sub models to produce the prediction model. Further, the model production section 11 may produce the prediction model using a plurality of sub models produced in advance.

The model production section 11 illustrated in FIGS. 5 and 11A includes sub models 111-1 to 111-S (S is a total number of the sub models) and a synthesis processing section 112.

The model production section 11 of the present example receives, as inputs thereto, the input time series signal $$\{x(\tau)\}_{\tau=1}^{t_c}$$

to the control section 1, time $$x(t_c+L)$$

$$T^L(t_c)=[T_1^L(t_c)T_2^L(t_c)\ldots T_{D_{im}}^L(t_c)] \quad \text{[Expression 6]}$$

$$T_j^L(t_c)=[T_j^L(t_c,1)T_j^L(t_c,2)\ldots T_j^L(t_c,M_T)]^T \quad \text{[Expression 7]}$$

of the input time series signal whose phase is same as that of a signal of the prediction target time ($t_c+L$), which is part of the output of the cycle fluctuation analysis section 12, and the reliability $$C_{T^L}(t_c)=[C_{t1}^L(t_c)C_{t2}^L(t_c)\ldots C_{tD_{im}}^L(t_c)] \quad \text{[Expression 8]}$$

$$C_{T_j^L}(t_c)=[C_{T_j^L}(t_c,1)C_{T_j^L}(t_c,2)\ldots C_{T_j^L}(t_c,M_T)]^T \quad \text{[Expression 9]}$$

of the time and model design information $$I^{model}(t_c)=[I^{model}(t_c,1)I^{model}(t_c,2)\ldots I^{model}(t_c,S)] \quad \text{[Expression 10]}$$

which is part of the output of the prediction accuracy estimation section 16, and outputs a prediction value $$\tilde{x}(t_c+L)=[\tilde{x}_1(t_c+L)\tilde{x}_2(t_c+L)\ldots \tilde{x}_{D_{im}}(t_c+L)] \quad \text{[Expression 11]}$$

$$\tilde{x}_j(t_c+L)=F_{t_c,j}^{com}(\tilde{x}_j(t_c+L,1),\tilde{x}_j(t_c+L,2),\ldots,\tilde{x}_j(t_c+L,S)) \quad \text{[Expression 12]}$$

of the prediction target time ($t_c+L$) and detailed information $$\tilde{I}^{\tilde{x}}(t_c+L)=[\tilde{I}^{\tilde{x}}(t_c+L,1)\tilde{I}^{\tilde{x}}(t_c+L,2)\ldots \tilde{I}^{\tilde{x}}(t_c+L,S)] \quad \text{[Expression 13]}$$

$$\tilde{I}^{\tilde{x}}(t_c+L,s)=[I_1^{\tilde{x}}(t_c+L,s)I_2^{\tilde{x}}(t_c+L,s)\ldots I_{D_{im}}^{\tilde{x}}(t_c+L,s)] \quad \text{[Expression 14]}$$

$$I_j^{\tilde{x}}(t_c+L,s)=[I_j^{\tilde{x}}(t_c+L,s,1)I_j^{\tilde{x}}(t_c+L,s,2)\ldots] \quad \text{[Expression 15]}$$

of the procedure of the prediction value calculation. Here, $$\tilde{x}_j(t_c+L,s)$$

is an output value in the jth dimension direction of a sub model s (s=1, 2, ..., S). Further, a function $$F_{t_c,j}^{com}(\bullet)$$

corresponds to an addition and multiplication process by the synthesis processing section 112 and is determined using model design information $$I^{model}(t_c,s)$$

and the prediction value at the prediction target time ($t_c+L$) is calculated as a synthesis of outputs of the sub models 111-1 to 111-S. Here, $$I^{model}(t_c,s)$$

is model design information of the sub model s, and $$I_j^{\tilde{x}}(t_c+L,s)$$

is information (calculation procedure information) of the output calculation procedure of an output $$\tilde{x}_j(t_c+L,s)$$

of the sub model s and part of design information of a function $$F_{t_c,j}^{com}(\bullet)$$

Further, $$I_j^{\tilde{x}}(t_c+L,s,i), i=1,2,$$

which is a factor of the function is information of a model parameter or particular information of the output calculation procedure or the function design.

In particular, the model production section 11 of the present example functions as an example of a model production section adapted to produce, using the input time series signal, the in-phase time information and the reliability of the in-phase time information calculated by the cycle fluctuation analysis section 12 and the model design information esti-mated by the prediction accuracy estimation section 16, a prediction model for predicting the value of the input time series signal after the predetermined time and predict and output the value of the input time series signal after the predetermined time using the prediction model.

Also it is possible for the model production section 11 to produce a plurality of sub models whose kinds of filters and models and parameter values are different from each other and a model of a synthesis of the sub models using an arbitrary time series signal which is an input to the control section 1 and whose principal component is cycle time-variable season dynamics, in-phase time information whose phase is same as that at the prediction target time which is part of the output of the cycle fluctuation analysis section 12 and reliability information of the in-phase time information, and model design information which is part of the output of the prediction accuracy estimation section 16, and output the prediction value of the input time series signal after the predetermined time and detailed information of the calculation procedure of the prediction value.

Further, the model production section 11 in the present embodiment can change the design of the sub models and the model of the synthesis of the sub models using the prediction accuracy information estimated by the prediction accuracy estimation section 16.

(1.3.1) Sub Models 111-1 to 111-S

The sub models 111-1 to 111-S are produced using model design information (information of a kind of a filter and a model or parameters of the filter and model) and are models for predicting a value of the input time series signal (or a specific component of the input time series signal) after the predetermined time. The number of the sub models is determined based on the total number of combinations of kinds of filters and models and kinds of parameters of the filters and models.

Where, in the design of the sub models 111-1 to 111-S, the cycle of season dynamics of a time series signal after a filter process varies with respect to time (time-variable), a problem that a prediction error increases from a cause of the cycle time variation is avoided using the in-phase time information in the input time series signal whose phase is same as that at the prediction target time which is an input from the cycle fluctuation analysis section 12 and the reliability information of the in-phase time information.

For the kind of the filter used for each sub model, for example, at least one of a moving average filter, a difference filter, a band-pass filter and a Kalman filter can be used.

For the sub models 111-1 to 111-S, for example, at least one of an SARIMA (Seasonal Auto-Regressive Integrated Moving Average) model, a seasonal adjustment exponential smoothing model, a non-linear type ARIMA (Auto-Regressive Integrated Moving Average) model and a soft computing model such as a neural network, a fuzzy or the like and so forth can be used.

Further, for the design of a model, for example, a design algorithm of the Yule Walker method, the Burg method, a least-square method and a gradient method, an arbitrary design parameter, an evaluation function and an evaluation algorithm of the AIC (Akaike information criterion) or a maximum likelihood procedure can be used.

The sub model s (111-1 to 111-S) illustrated in FIG. 11B is an example for implementing a scheme for effectively modeling cycle time-variable season dynamics and another scheme for directly predicting the prediction target time ($t_c+L$) using a SARIMA model as a kind of the model and further using time information $$T^L(t_c)$$

in the input time series signal whose phase is same as that of the signal of the prediction target time ($t_c$+L). Here, an output where the input time series signal $$\{x(\tau)\}_{\tau=1}^{t_c}$$

is used as an input is calculated by the following expression.
[Expression 16]

$$\tilde{x}(t_c+L,s)=[\tilde{x}_1(t_c+L,s)\tilde{x}_2(t_c+L,s)\ldots\tilde{x}_{D_{im}}(t_c+L,s)]$$

$$\phi_j^p(t_c)\Phi_j^{M_T}(t_c,T_j^L(t_c))(1-B)^d x_j(t_c+L,s)=\theta_j^q(t_c)e_j(t_c+L)$$

$$\phi_j^p(t_c)=1-\phi_{j,1}(t_c)B^L-\phi_{j,2}(t_c)B^{2L}-\ldots-\phi_{j,p}(t_c)B^{pL}$$

$$\theta_j^q(t_c)=1-\theta_{j,1}(t_c)B^L-\theta_{j,2}(t_c)B^{2L}-\ldots-\theta_{j,q}(t_c)B^{qL}$$

$$\Phi_j^{M_T}(t_c,T)=1-\Phi_{j,1}(t_c)B^{t_c+L-t(1)}-\Phi_{j,2}(t_c)B^{t_c+L-t(2)}-\ldots-\Phi_{j,M_T}(t_c)B^{t_c+L-t(M_T)}$$

$$T=[t(1)t(2)\ldots t(M_\tau)]$$

$$\{x_j(\tau,s)\}_{\tau=1}^{t_c}=F_s^{div}([x_j(\tau)]_{\tau=1}^{t_c},I_j^{model}(t_c,s)) \quad (2)$$

Here, a derivation method of the expression (2) given just above is described.

The expression (2) given above is an expression of a time series model for describing time series data whose cycle of a seasonal component fluctuates.

Further, in order to facilitate understandings of the derivation method of the expression (2) given above, description of a definition of some terms and models of AR (Auto-Regression: auto regression), MA (Moving Average: moving average), ARMA (Auto-Regression Moving Average: auto regression moving average), ARIMA (Auto-Regression Integrated Moving Average: auto regression integrated moving average) and SARIMA is carried out.

First, the time series model signifies a relational expression which describes a regulation of a behavior of time series data. Further, a steady process signifies a probability process in which a probability distribution does not vary. Further, a steady time series signifies time series data produced by the steady process and has a characteristic that the average value and the variance do not vary within any interval of the time series. It is to be noted that a design method for AR and ARMA models with respect to the steady time series has been established.

Further, a trend component signifies a component which varies the average value of the time series continuously for longtime. Further, a seasonal component signifies a component which periodically varies the average value of the time series and a non-steady time series signifies a time series other than the steady time series. As the non-steady time series, for example, a time series with which the trend component or the seasonal component is mixed is available.

First, the AR model is described.

The AR model represents values of a steady time series $z(t)$ (t=0, 1, 2, . . . ) as a linear equation of time series data in the past with respect to the steady time series like the following expression (3).

$$z(t)=\phi_1 z(t-1)+\phi_2 z(t-2)+\ldots+\phi_p z(t-p)-e(t) \quad (3)$$

Here, p is an order of the model, $\phi_i$ (i=1, 2, . . . , p) is a model coefficient, and e(t) is a model error at time t.

If the terms other than e(t) are moved from the left side of the expression (3) to the right side, then the following expression (4) is obtained.

$$z(t)-\phi_1 z(t-1)-\phi_2 z(t-2)-\ldots-\phi_p z(t-p)=e(t) \quad (4)$$

Further, if, as a delay operator B, for example, B which satisfies the following expression (5)

$$B^d z(t)=z(t-d) \quad (5)$$

is used to describe the expression (4) given above, then the following expressions (6) and (7) are obtained.

$$\phi^p z(t)=e(t) \quad (6)$$

$$\phi^p\equiv(1-\phi_{1B}-\phi_2 B^2-\ldots-\phi_p B^p) \quad (7)$$

Now, the MA model is described.

The MA model represents values of the steady time series z(t) as a linear equation of time series data e(t) of noise generated till then like the following expression (8).

$$z(t)=e(t)-\theta_1 e(t-1)-\theta_2 e(t-2)-\ldots-\theta_q e(t-q) \quad (8)$$

Here, q is an order of the model and $\theta_j$ (j=1, 2, . . . , q) is a model coefficient.

If the expression (8) given above is represented using the delay operator B, then the following expressions (9) and (10) are obtained.

$$z(t)=\theta^q e(t) \quad (9)$$

$$\theta^q\equiv(1-\theta_1 B-\theta_2 B^2-\ldots-\theta_q B^q) \quad (10)$$

Further, the ARMA model is described.

The ARMA model represents values of the steady time series z(t) as a linear equation between time series data in the past with respect to the steady time series and time series data e(t) of noise generated till then by like the following expression (11).

$$z(t)=\phi_1 z(t-1)+\phi_2 z(t-2)+\ldots+\phi_p z(t-p)e(t)-\theta_1 e(t-1)-\theta_2 e(t-2)-\ldots-\theta_q e(t-q) \quad (11)$$

Here, if the terms other than terms relating to noise are moved from the left side of the expression (11) given above to the right side, then the following expression (12) is obtained.

$$z(t)-\phi_1 z(t-1)-\phi_2 z(t-2)-\ldots-\phi_p z(t-p)=e(t)-\theta_1 e(t-1)-\theta_2 e(t-2)-\ldots-\theta_q e(t-q) \quad (12)$$

Further, if the expression (12) given just above is represented using delay operators B, $\phi^p$ and $\theta^q$, then the following expression (13) is obtained.

$$\phi^p z(t)=\theta^q e(t) \quad (13)$$

Now, the ARIMA model is described.

The ARIMA model is a model for describing values of a non-steady time series y(t) (t=1, 2, . . . ) including a trend component.

The trend component involved in the non-steady time series y(t) can be removed by calculating a difference from time series data of a delay 1 by a predetermined number d of times (≥1). In particular, a residual z(t) at this time is represented by the following expression (14).

$$z(t)=(1-B)^d y(t) \quad (14)$$

Here, since the time series of the residual z(t) where the difference is suitably calculated is a steady time series, it can be modeled by the ARMA model. In particular, the following expression (15) is satisfied.

$$\phi^p z(t)=\theta^q e(t) \quad (15)$$

Accordingly, the ARIMA model is represented by the following expression (16) obtained by substituting the expression (14) into the expression (15) given above.

$$\phi^p(1-B)^d y(t)=\theta^q e(t) \quad (16)$$

Now, the SARIMA model is described.

The SARIMA model is a model for describing values of a non-steady time series x(t) (t=1, 2, . . . ) including a trend component and a seasonal component. It is to be noted that, in the following description, a case in which the cycle c of the seasonal component is c>>1 is considered.

The trend component involved in the non-steady time series x(t) can be removed by calculating a difference from the time series data of the delay 1 by d (≥1) times as described in the description of the ARIMA model. A residual w(t) at this time is represented by the following expression (17).

$$w(t)=(1-B)^d x(t) \quad (17)$$

Further, the seasonal component involved in the non-steady time series x(t) after the trend component thereof is removed can be removed by any one of methods [1] to [3] described below.

As the method [1], for example, by calculating the difference from the time series data of a delay c by D (≥0) times, a residual v(t) at this time is represented by the following expression (18).

$$v(t)=(1-B^c)^D w(t) \quad (18)$$

Further, as the method [2], for example, an AR model is produced from the time series data (in particular, time series data sampled at a time distance c) in which only in-phase data are extracted, and a difference of the AR model is calculated. In particular, a residual v(t) at this time is represented by the following expressions (19) and (20).

$$v(t)=\Phi^P w(t) \quad (19)$$

$$\Phi^P \equiv (1-\Phi_1 B^c - \Phi_2 B^{2c} - \ldots - \Phi_P B^{Pc}) \quad (20)$$

Further, as the method [3], for example, a method which uses both of the methods [1] and [2] described above is available. In particular, a residual v(t) at this time is represented by the following expression (21).

$$v(t)=\Phi^P(1-B^c)^D w(t) \quad (21)$$

Here, since the residual time series v(t) from which the seasonal component is removed is a steady time series, it can be modeled with the ARMA model. In particular, the following expression (22) is satisfied using the v(t).

$$\phi^P v(t)=\theta^q e(t) \quad (22)$$

Accordingly, the SARIMA model is represented by the following expression (23) by substituting the expressions (17) and (21) into the expression (22) given above.

$$*\phi^P \Phi^P (1-B^c)^D (1-B)^d x(t) = \theta^q e(t) \quad (23)$$

Now, taking the foregoing into consideration, the expression (2) given above is described.

As described hereinabove, it is assumed that, in an ordinary SARIMA model, the cycle c of a seasonal component is always fixed.

Figure 29:
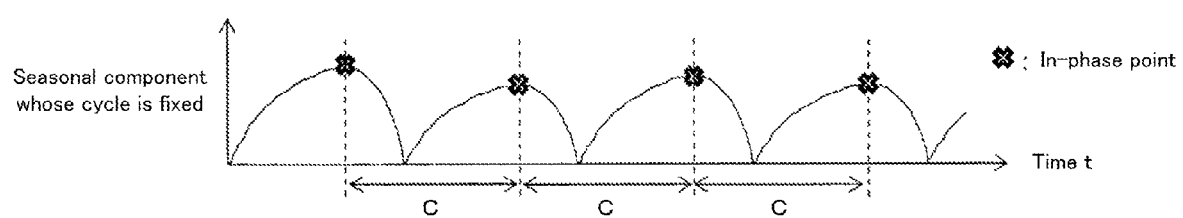
FIG. 29 is a view illustrating a seasonal component of a fixed cycle.

This signifies that, in a time series of a seasonal component, a portion of the same phase appears after every cycle c as illustrated in FIG. 29. In the SARIMA model described hereinabove, the seasonal component is removed by the expressions (18) through (21).

Figure 30:
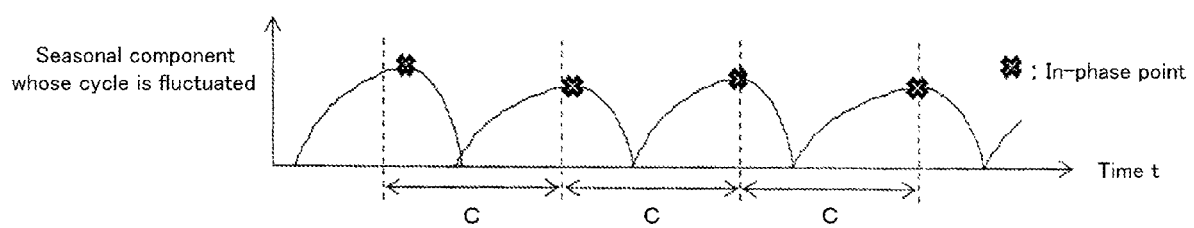
FIG. 30 is a view illustrating a seasonal component whose cycle fluctuates.

Meanwhile, since the cycle of a seasonal component of an input time series signal such as the tumor position which is determined as a prediction target by the prediction process of the present example varies as illustrated in FIG. 30, different from the example illustrated in FIG. 29, a portion of the same phase does not necessarily appear after every cycle c.

Consequently, from an input time series signal such as the tumor position, it is impossible to remove a seasonal component involved in the input time series signal using the expressions (18) through (21) given hereinabove.

Therefore, in the present embodiment, the expressions (18) through (21) given hereinabove are improved so that they function appropriately for a non-steady time series in which the cycle of a seasonal component fluctuates. This is the expression (2) given hereinabove.

As an improved point described above, for example, the value of D of the expression (18) is determined to be zero so that the processing of the expression (18) is not carried out.

Further, time series data formed by extracting data of the same phase to be used for the processing of the expressions (19) and (20) are produced not by sampling by the cycle c as in an ordinary SARIMA model but using in-phase time information calculated by the cycle fluctuation analysis section 12.

It is to be noted that, in order to carryout effective time series prediction using the expression (2) given hereinabove, it is demanded to appropriately design the values of the model coefficients φ,θ,Φ and the model orders p, q, d.

In the present example, as the design method of the model coefficients φ,θ,Φ, such methods as, for example, the Yule Walker method, the Burg method, a least-square method and a gradient method as described hereinabove, and as the design method for the model orders p, q, d, such methods as, for example, the ACI and a maximum likelihood method can be used.

It is to be noted that, as described hereinabove, B is an operator for delaying the time parameter. For example, by using the operator B to act on the variable x having a time parameter t from the front, the relationship of $$B^d x(t) = x(t-d) \quad \text{[Expression 17]}$$

is satisfied. Further, $$F_s^{div}(\bullet)$$

is a function for calculating, from the input time series signal $$\{x_j(\tau)\}_{\tau=1}^{t_c}$$

to the control section 1 and the mode design information $$I_j^{model}(t_c,s)$$

the time series signal $$\{x_j(\tau,s)\}_{\tau=1}^{t_c}$$

after the filter process which is made a target by the sub model s. Here, $$M_T$$

is an arbitrary constant. Further, the model orders p, q, d and the model parameters $$\phi_{j,i}, i=1,2,\ldots,p$$

$$\theta_{j,k}, k=1,2,\ldots,q$$

$$\Phi_{j,l}, l=1,2,\ldots,M_T \quad \text{[Expression 18]}$$

are determined using the reliability information of $$T_j^L(t_c)$$

the model design information $$C_{t_j}^L(t_c)$$

and an evaluation algorithm of the AIC or the most likelihood method.

For example, in the case where, for certain constants, $$M_m, \delta_{C_T}$$

a condition of $$\|\{m|m=1,2,\ldots,M_T \wedge C_{T_j}^L(t_c,m) > \delta_{C_T}\}\| \leq M_m \quad \text{[Expression 19]}$$

is satisfied, it is decided that the seasonal dynamics of the input time series signal are not suitable for prediction, and $$\begin{cases} \bar{x}_j(t_c+L,s) = \bar{x}_j(t_c+L-1,s) \\ I_j^{\bar{x}}(t_c+L,s,1) = 0 \end{cases} \quad \text{[Expression 20]}$$

is outputted and the model production process is ended. Here, $$I_j^{\bar{x}}(t_c+L,s,1)$$

is factor information of information $$I_j^{\bar{x}}(t_c+L,s)$$

of the output calculation procedure, and the value thereof is zero (corresponding to absence of updating of the output value).

On the other hand, if the condition described hereinabove is not satisfied, then the design algorithm for the model parameter is set as $$\Phi_i(t_c) = C_{T_j^L}(t_c, m) \Big/ C_{T_j^L}^\Sigma(t_c), \quad \text{[Expression 21]}$$

$$m = 1, 2, \ldots, M_T$$

$$C_{T_j^L}^\Sigma(t_c) \equiv \sum_{m=1}^{M_T} C_{T_j^L}(t_c, m)$$

Further, an output $$\tilde{x}_j(t_c+L,s)$$

where the model orders p, q, d are determined by the AIC or the maximum likelihood method is calculated, and the factor information of the output calculation procedure is set to $$I_j^{\tilde{x}}(t_c+L,s,1)=1 \quad \text{[Expression 22]}$$

which corresponds to presence of updating of the output value. In the present example, where p=0 and d=0, the output of the sub model s is $$\tilde{x}_j(t_c+L,s) = \sum_{m=1}^{M_T} C_{T_j^L}(t_c, m) \cdot x_j(T_j^L(t_c,m),s) \Big/ C_{T_j^L}^\Sigma(t_c) \quad \text{[Expression 23]}$$

It is to be noted here that, where $$T_j^L(t_c,m)$$

is a real number, a function $$R(\bullet)$$

for rounding up an input and outputting the rounded input is used to determine $$x_j(T_j^L(t_c,m),s)$$

by linear approximation of $$x_j(R)T_j^L(t_c,m)-0.5),s)$$

and $$x_j(R(T_j^L(t_c,m)+0.5),s)$$

In particular, by using the model design information (the type of the filter or the model and information of parameters of them), the sub models 111-1 to 111-S function as an example of a prediction model for predicting the value of the input time series signal (or a particular portion of the same) after the predetermined time elapses.

Further, the sub models 111-1 to 111-S may have different structures or characteristics.

(1.3.2) Synthesis Processing Section 112

The synthesis processing section 112 carries out addition-multiplication processes of outputs of the sub models 111-1 to 111-S to calculate a prediction value of prediction target time ($t_c+L$) of the input time series signal to the control section 1. The synthesis processing section 112 illustrated in FIGS. 5 and 11A uses the outputs $$\tilde{x}_j(t_c+L,s), s=1,2,\ldots,S \quad \text{[Expression 24]}$$

of all sub models 111-1 to 111-S to calculate a prediction value of the input time series signal to the control section 1 at the prediction target time ($t_c+L$) in accordance with the following expression.

$$\tilde{x}_j(t_c+L)=F_{t_c,j}^{com}(\tilde{x}_j(t_c+L,1),\tilde{x}_j(t_c+L,2),\ldots,\tilde{x}_j(t_c+L,S)) \quad \text{[Expression 25]}$$

Here, particular specifications of the function $$F_{t_c,j}^{com}(\bullet)$$

can be determined arbitrarily while taking the model design information $$I^{model}(t_c)$$

into consideration as occasion demands.

(1.4) Cycle Fluctuation Analysis Section 12

The cycle fluctuation analysis section 12 analyzes and calculates information effective to prevent a problem that the prediction accuracy of the control section 1 deteriorates by a cause of a cycle fluctuation of the input time series signal.

The cycle fluctuation analysis section 12 illustrated in FIGS. 5 and 6A includes a correlation analysis section 121, a cache memory 122, a cycle estimation section 123, a cycle prediction section 124, an in-phase time estimation section 125, a time delay section 126, another cache memory 127, and a difference processing section 128.

The cycle fluctuation analysis section 12 of the present example receives the time series signal $$\{x(\tau)\}_{\tau=1}^{t_c}$$

as an input and calculates the time $$T^L(t_c)=[T_1^L(t_c)T_2^L(t_c)\ldots T_{D_{im}}^L(t_c)] \quad \text{[Expression 26]}$$

$$T_j^L(t_c)=[T_j^L(t_c,1)T_j^L(t_c,2)\ldots T_j^L(t_c,M_T)]^T \quad \text{[Expression 27]}$$

of the position of the input time series signal at which it becomes in phase with the signal of the prediction target time ($t_c+L$), and the reliability $$C_{T^L}(t_c)=[C_{T_1}^L(t_c)C_{T_2}^L(t_c)\ldots C_{tD_{im}^L}(t_c)] \quad \text{[Expression 28]}$$

$$C_{T_j^L}(t_c)=[C_{T_j^L}(t_c,1)C_{T_j^L}(t_c,2)\ldots C_{T_j^L}(t_c,M_T)]^T \quad \text{[Expression 29]}$$

of the time of the position of the input time series signal, as well as the prediction accuracy information $$\{\Delta^L P(\tau)\}_{\tau=2max(P_j)+L}^{t_c} \quad \text{[Expression 30]}$$

$$\Delta^L P(\tau)=[\Delta^L P_1(\tau)\Delta^L P_2(\tau)\ldots \Delta^L P_{D_{im}}(\tau)] \quad \text{[Expression 31]}$$

of the cycle. Here, $$T_j^L(t_c,m)$$

is the mth highest value from among the time values of the positions of the input time series which becomes in phase with the seasonal dynamic of the prediction target time ($t_c+L$) and has such a relationship as illustrated in FIG. 6B. Further, $$C_{T_j^L}(t_c,m)$$

is the reliability of $T_j^L(t_c, m)$ and $M_T$ is an arbitrary positive constant. Further, $\Delta^{LP}_j(\tau)$ is accuracy information of the prediction value $P_j(\tau)$ in the case where the cycle (estimated value)

$\{x_j(t)\}_{t=1}^{\tau-L}$ at time $\tau$ is predicted using information of the time series signal $\check{P}_j(\tau)$ till time ($\tau$-L), and has such a relationship as illustrated in FIG. 6C.

In particular, the cycle fluctuation analysis section 12 of the present example functions as an example of a cycle fluctuation analysis section adapted to assume a certain component of an input time series signal as a time series signal whose cycle varies with respect to time to carry out a correlation analysis between part of the input time series signal and the input time series signal, estimate a cycle fluctuation of the input time series signal and reliability of the cycle fluctuation using a result of the correlation analysis, predict a cycle of the input time series signal after predetermined time using the cycle fluctuation and the reliability of the cycle fluctuation and calculate, using the result of the correlation analysis and the predicted cycle, in-phase time information which represents time of the input time series signal whose phase becomes same as a phase of the input time series signal after the predetermined time and the reliability of the in-phase time information.

In short, the cycle fluctuation analysis section 12 can calculate information effective to prevent the problem that the prediction accuracy, after predetermined time passes, of the input time series signal to the control section 1 whose principal component is cycle time-variable seasonal dynamics, deteriorates by a cause of a cycle fluctuation of the input time series signal.

(1.4.1) Correlation Analysis Section 121

The correlation analysis section 121 calculates a correlation analysis result necessary to estimate or predict a cycle fluctuation of the input time series signal by a correlation analysis of the input time series signal.

The correlation analysis section 121 illustrated in FIGS. 5 and 7A receives the time series signal $\{x(\tau)\}_{\tau=1}^{t_c}$ as an input thereto and outputs a result $C(t_c) = [C_1(t_c) C_2(t_c) \ldots C_{D_{im}}(t_c)]$  [Expression 32]

$C_j(t_c) = [C_j(t_c, 0) C_j(t_c, 1) \ldots C_j(t_c, t_c - \max(P_j))]$  [Expression 33]

of the correlation analysis. Here, $\max(P_j)$ is an estimated value of a maximum value of the cycle fluctuation which is estimated to possibly appear with ordinary seasonal dynamics of the input time series signal. Further, the value of $C_j(t_c, k)$ is calculated in accordance with $$C_j(t_c, k) = \begin{cases} 0 & \text{if } t_s < 2\max(P_j) \\ \dfrac{\sum_{l=1}^{\max(P_j)} (y_j(t_c, 0, l) - \bar{y}_j(t_c, 0))(y_j(t_c, k, l) - \bar{y}_j(t_c, k))}{\sqrt{\sum_{l=1}^{\max(P_j)} (y_j(t_c, 0, l) - \bar{y}_j(t_c, 0))^2} \sqrt{\sum_{l=1}^{\max(P_j)} (y_j(t_c, k, l) - \bar{y}_j(t_c, k))^2}} & \text{otherwise} \end{cases}$$  [Expression 34]

$y_j(t_c, k, l) \equiv x_j(t_c - \max(P_j) + l - k)$ $\bar{y}_j(t_c, k) \equiv \dfrac{1}{\max(P_j)} \sum_{l=1}^{\max(P_j)} x(t_c, k, l)$ and this value is a correlation function of the time series signal $\{x(\tau)\}_{\tau=t_c-\max(P_j)+1}^{t_c}$ of thick broken line portions of FIGS. 7B and 7C and the time series signal $\{x(\tau)\}_{\tau=t_c-\max(P_j)-k+1}^{t_c-k}$ of a solid line portion of FIG. 7C, and varies, in the case where seasonal dynamic are involved in the input time series signal, as illustrated in FIG. 7D by varying the value of k.

In particular, the correlation analysis section 121 functions as an example of a correlation analysis section for carrying out a correlation analysis between part of the input time series signal and the input time series signal. For example, the correlation analysis section 121 can calculate a correlation analysis result to be used for estimation or prediction of a cycle fluctuation of the input time series signal by a correlation analysis for the input time series signal and output the correlation analysis result to the cache memory 122.

(1.4.2) Cache Memory 122

The cache memory 122 is a memory for storing a correlation analysis result $C(t_c)$ which is an output of the correlation analysis section 121 and outputs an arbitrary piece of information from among pieces of information stored for a fixed period in the past.

The cache memory 122 illustrated in FIG. 5 outputs a time series $\{C(\tau)\}_{\tau=1}^{t_c}$ of all information stored therein after time $\tau=1$ till current time $t_c$.

(1.4.3) Cycle Estimation Section 123

The cycle estimation section 123 calculates, using time series information of a correlation analysis result of the input time series signal, time series information of an estimated value of the fluctuation of the cycle of the input time series signal and time series information of the reliability of the estimated value.

The cycle estimation section 123 illustrated in FIGS. 5 and 8A receives, as an input thereto, time series information $\{C(\tau)\}_{\tau=1}^{t_c}$ of a correlation analysis result which is an output of the cache memory 122 and outputs time series information $$\{P(\tau)\}_{\tau=2max(P_j)}^{t_c}$$

$$P(\tau)=[P_1(\tau)P_2(\tau)\ldots P_{D_{im}}(\tau)] \quad \text{[Expression 35]}$$

of the estimated value of the cycle of the input time series signal to the control section 1 and time series information $$\{C_P(\tau)\}_{\tau=2max(P_j)}^{t_c}$$

$$C_P(\tau)=[C_{P_1}(\tau)C_{P_2}(\tau)\ldots CP_{D_{im}}(\tau)] \quad \text{[Expression 36]}$$

of the reliability of the time series information of the estimated value. Here, the period $$P_j(\tau)$$

of the phase (corresponding to an asterisk in FIG. 8B) at time τ in the jth dimension direction of the input time series signal corresponds to the length of the seasonal dynamics component of the time series signal $$\{x_j(\tau)\}_{\tau=1}^{t_c}$$

corresponding to the latest one period after time τ, and $$C_{P_j}(\tau)$$

is reliability of the value and is calculated, as illustrated in FIG. 8B, as a weighted average of a value determined within the range from $t_s=\tau$ to $t_s=\tau+\max(P_j)$, from the correlation analysis result $$\{C_j(\tau)\}_{\tau=1}^{t_c}$$

with regard to the time series signal in the jth dimension direction, in accordance with the following expressions.

$$P_j(\tau) = \begin{cases} 0 & \text{if } \sum_{t_s=\tau}^{N(\tau,max(P))} C_{K_j^{[u1]}}(t_s) = 0 \\ \dfrac{\sum_{t_s=\tau}^{N(\tau,max(P))} C_{K_j^{[u1]}}(t_s)}{\sum_{t_s=\tau}^{N(\tau,max(P))} C_{K_j^{[u1]}}(t_s)} & \text{otherwise} \end{cases} \quad \text{[Expression 37]}$$

$$C_{P_j}(\tau) = \frac{\sum_{t_s=\tau}^{N(\tau,max(P))} C_{K_j^{[u1]}}(t_s)}{N(\tau,max(P))-\tau+1} \quad \text{[Expression 38]}$$

$$N(\tau,max(P)) = \begin{cases} \tau+max(P) & \text{if } \tau+max(P) < t_c \\ t_c & \text{otherwise} \end{cases} \quad \text{[Expression 39]}$$

$$K_j^{[u1]}(t) = \quad \text{[Expression 40]}$$

$$\begin{cases} 0 & \text{if there is no upper peak} \\ \arg_k \text{Get\_[1]st\_Upper\_Peak}(C_j(t,k)) & \text{otherwise} \end{cases}$$

$$C_{K_j^{[u1]}}(t) = \quad \text{[Expression 41]}$$

$$\begin{cases} 0 & \text{if there is no upper peak} \\ C_j(t, K_j^{[u1]}(t)) & \text{otherwise} \end{cases}$$

Here, $$\arg_k \text{Get\_[1]st\_Upper\_Peak}(C_j(t,k))$$

is a function which outputs, in the case where k is gradually changed from 0 to $$\max(P_j)$$

the value of k at which the value of $$C_j(t,k)$$

exhibits a convex peak first (refer to FIG. 8C).

In particular, the cycle estimation section 123 of the present example functions as an example of a cycle estimation section for estimating the cycle fluctuation of the input time series signal and the reliability of the cycle fluctuation using a result of the analysis by the correlation analysis section 121. For example, the cycle estimation section 123 can calculate, from time series information of the correlation analysis result of the input timer series signal which is an output of the cache memory 122, time series information of the estimated value of the fluctuation of the cycle of the input time series signal and time series information of the reliability of the estimated value.

(1.4.4) Cycle Prediction Section 124

The cycle prediction section 124 predicts a cycle from time $(t_c+1)$ to prediction target time $(t_c+L)$ using time series information of the estimated value of the fluctuation of the cycle of the input time series signal till current time $t_c$ and time series information of the accuracy of the estimated value.

Figure 9:
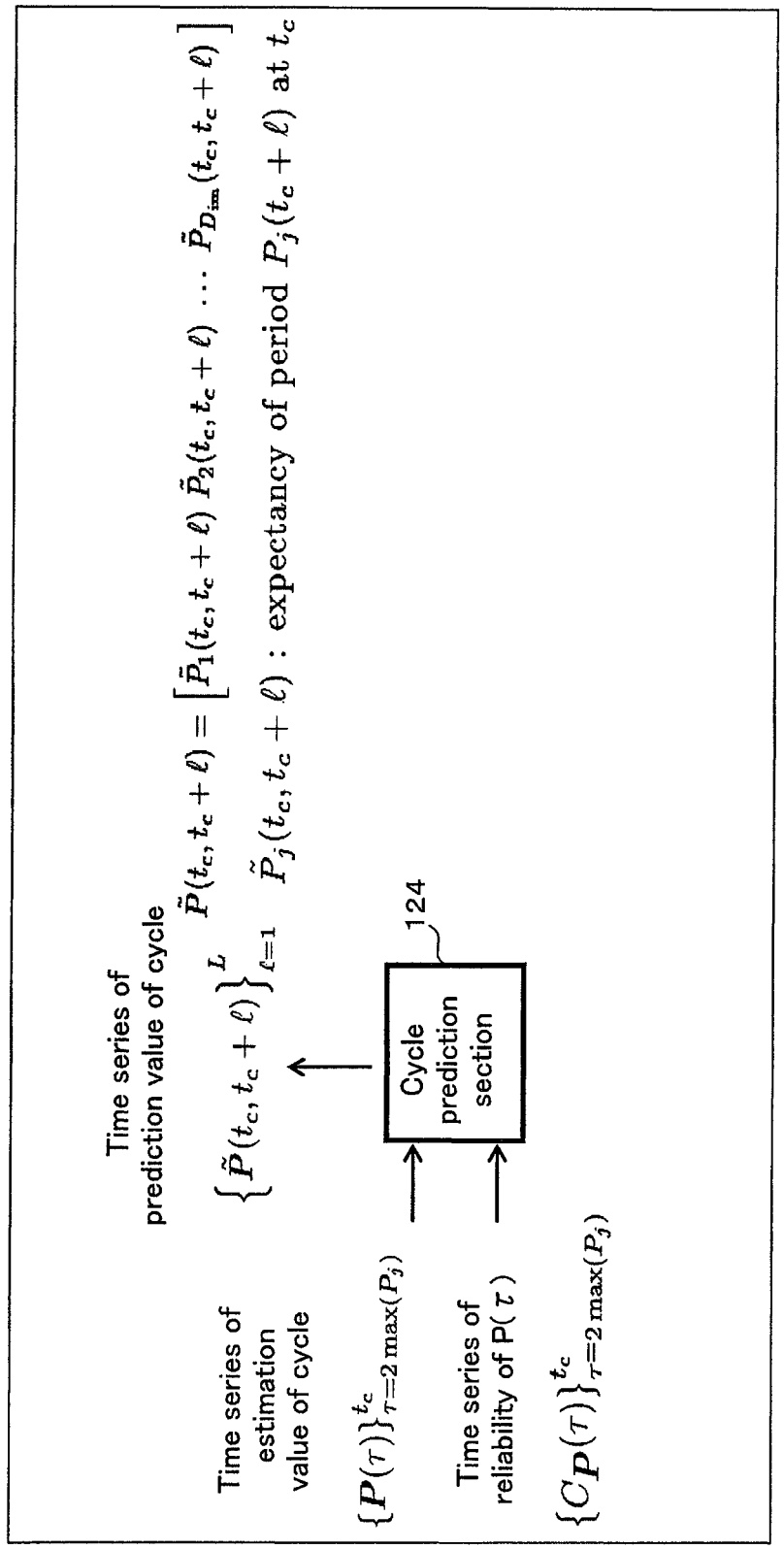
FIG. 9 is a view illustrating an example of operation of a cycle prediction section 124.

The cycle prediction section 124 illustrated in FIGS. 5 and 9 receives, as inputs thereto, time series information $$\{P(\tau)\}_{\tau=2max(P_j)}^{t_c}$$

of the estimated value of the fluctuation of the cycle of the input time series signal which is an output of the cycle estimation section 123 till current time $t_c$ and the time series information $$\{C_P(\tau)\}_{\tau=2max(P_j)}^{t_c}$$

of the reliability of the time series information of the estimated value, $$\{P(t_c+l)\}_{l=1}^{L}$$

and outputs the predicted time series information $$\{\tilde{P}(t_c,t_c+l)\}_{l=1}^{L}$$

$$\tilde{P}(t_c,t_c+l)=[\tilde{P}_1(t_c,t_c+l)\tilde{P}_2(t_c,t_c+l)\ldots \tilde{P}_{D_{im}}(t_c,t_c+l)] \quad \text{[Expression 42]}$$

at current time $t_c$. Here, $$\tilde{P}_j(t_c,t_c+l)$$

is a prediction value of the period $$P_j(t_c+l)$$

of the signal in the jth dimension direction at time $(t_c+1)$ as predicted at time $t_c$. This value is calculated, using, for example, data $$\{P(\tau)\}_{\tau=2max(P_j)}^{t_c}$$

whose reliability is higher than an arbitrary constant $$\delta C_{P_j}$$

that is, appropriate data, from among the data of the estimated value $$P_j(\tau_c),\tau_c \in \{\tau|(2\max(P_j)\leq\tau\leq t_c)\wedge(C_{P_j}(\tau)>\delta C_{P_j})\wedge(\min(P_j)\geq P_j(\tau)\geq\max(P_j))\} \quad \text{[Expression 43]}$$

of the cycle which is an input to the cycle prediction section 124, from such an autoregressive model as given by the following expression.

$$\tilde{P}_j(t_c, t_c+l) = \overline{P_j} + \sum_{i=0}^{M_P} \phi_{j,i}^l (P_j(t_c - il) - \overline{P_j}) \ldots \quad \text{[Expression 44]}$$

$$l = 1, 2, \ldots, L$$

Here, $$\min(P_j)$$

is an estimated value of a minimum value of the cycle fluctuation which may possibly appear in ordinary dynamic of the time series signal $$\{x_j(\tau)\}_{\tau=1}^{t_c}$$

Further, $$M_P$$

and $$\phi_{j,i}^l, i=0,1,2,\ldots,M_P$$

are a dimension number and an autoregressive coefficient of the model, and can be determined, for example, from a model design algorithm such as the Yule Walker method, the Burg method, a least-square method and a gradient method, and a model evaluation algorithm such as the AIC or the most likelihood method.

In particular, the cycle prediction section 124 functions as an example of a cycle prediction section for predicting a cycle of the input time series signal after the predetermined time using the cycle fluctuation and the reliability of the cycle fluctuation estimated by the cycle estimation section 124. For example, the cycle prediction section 124 can predict the cycle from time $(t_c+1)$ to prediction target time $(t_c+L)$ by producing a prediction model based on a model production algorithm such as the Yule Walker method, the Burg method, a least-square method and a gradient method, and a model evaluation algorithm such as the AIC or the most likelihood method using the time series information of the estimated value of the fluctuation of the cycle of the input time series signal till current time $t_c$ and the time series signal of the reliability of the estimated value which are outputs of the cycle estimation section 123, and carrying out prediction using the prediction model.

(1.4.5) In—Phase Time Estimation Section 125

The in-phase time estimation section 125 outputs in-phase time information of the phase of an input time series signal having a phase same as that at the prediction target time and the reliability information of the in-phase time information, which are information effective to prevent the problem that the prediction accuracy of the model production section 11 deteriorates by a cause of a cycle fluctuation of the input time series signal using the input time series signal to the control section 1, time series information of the correlation analysis result of the input time series signal, and the time series information of the prediction result of the period of the input time series signal till the prediction target time.

The in-phase time estimation section 125 illustrated in FIGS. 5 and 10A receives, as inputs thereto, the input time series signal $$\{x(\tau)\}_{\tau=1}^{t_c}$$

the time series information $$\{C(\tau)\}_{\tau=1}^{t_c}$$

of the correlation analysis result which is an output of the cache memory 122 and the time series information $$\{\tilde{P}(t_c,t_c+l)\}_{l=1}^{L}$$

of the prediction result of the cycle of the input time series signal till the prediction target time, and outputs the time $$T^L(t_c) = [T_1^L(t_c) T_2^L(t_c) \ldots T_{D_{im}}^L(t_c)] \quad \text{[Expression 45]}$$

$$T_j^L(t_c) = [T_j^L(t_c,1) T_j^L(t_c,2) \ldots T_j^L(t_c,M_T)]^T \quad \text{[Expression 46]}$$

of the phase of the input time series signal of a phase same as that of the prediction target time, and the reliability $$C_{T^L}(t_c) = [\, C_{T_1^L}(t_c) \;\; C_{T_2^L}(t_c) \;\; \ldots \;\; C_{T_{D_{im}}^L}(t_c) \,] \quad \text{[Expression 47]}$$

$$C_{T_j^L}(t_c) = [\, C_{T_j^L}(t_c,1) \;\; C_{T_j^L}(t_c,2) \;\; \ldots \;\; C_{T_j^L}(t_c,M_T) \,]^T \quad \text{[Expression 48]}$$

of the time of the phase of the input time series signal. Here, $$T_j^L(t_c,m)$$

is the mth highest value from among the time values of the time series signal $$\{x_j(\tau)\}_{\tau=1}^{t_c}$$

of a phase same as that of the prediction value of the phase of the seasonal dynamics at the prediction target time $(t_c+L)$, and has such a relationship as illustrated in FIG. 6B. Further, $$C_{T_j^L}(t_c,m)$$

is the reliability of $$T_j^L(t_c,m)$$

and $$M_T$$

is an arbitrary positive constant. A calculation method of $$T_j^L(t_c,m)$$

and $$C_{T_j^L}(t_c,m)$$

is described below.

First, with regard to an arbitrary constant $$\delta_{K_j^{[u1]}}$$

it is verified whether or not a condition of $$(K_j^{[u1]}(t_c) \leq \min(P_j) \nu(\max(P_j \leq K_j^{[u1]}(t_c)) \nu(C_{K_j^{[u1]}}(t_c) < \delta_{K_j^{[u1]}})) \quad \text{[Expression 49]}$$

is satisfied. If the condition is satisfied, then it is decided that the latest seasonal dynamics are not suitable for prediction, and $$\begin{cases} T_j^L(t_c, k) = 0 \\ C_{T_j^L}(t_c, k) = 0 \end{cases} \quad \text{[Expression 50]}$$

$$k = 1, 2, \ldots, M_T$$

is set, and then the processing of the in-phase time estimation section 125 is ended.

On the other hand, in the case where the condition described hereinabove is not satisfied, since the time value which is lower than the current time value $t_c$ and is nearest to $t_c$ (the leftmost star mark surrounded by a rectangle in FIG. 10B) from among the time values of the phase of the input time series signal (star mark in FIG. 10B) having a phase same as that the phase (rightmost asterisk in FIG. 10B) of the prediction target time ($t_c$+L) has such a relationship as illustrated in FIG. 10B, it is calculated in accordance with the following expression.

$$T_j^L(t_c,1) = t_1(M_i) \qquad \text{[Expression 51]}$$

$$t_1(i) = t_1(i-1) - R(\tilde{P}_j(t_c, t_1(i-1))) \qquad \text{[Expression 52]}$$

$$t_1(0) = t_c + L \qquad \text{[Expression 53]}$$

Here,

R(•)

is a function for rounding an input and outputting the rounded input, and $M_I$ is a minimum value of i which satisfies $$t_1(i) < t_c, i \in \{1, 2, \ldots\} \qquad \text{[Expression 54]}$$

Further, the reliability of $T^L(t_c, 1)$ is given by $$C_{T_j^L}(t_c, 1) = 1 \qquad \text{[Expression 55]}$$

Further, $T_j^L(t_c, m)$ (time of the first and second asterisks from the left in FIG. 10D) at m=2, 3, . . . , MT and the reliability $C_{T_j^L}(t_c, m)$ of the value are calculated as weighted averages of the values determined within an appropriate range of $t_s$ in accordance with the following expressions.

$$T_j^L(t_c, m) = \qquad \text{[Expression 56]}$$

$$\begin{cases} 0 & \text{if } \sum_{t_s=T_j^L(t_c,1)}^{t_c} C_{T_j^L}(t_c, m, t_s) = 0 \\ \dfrac{\sum_{t_s=T_j^L(t_c,1)}^{t_c} C_{T_j^L}(t_c, m, ts) \cdot T_j^L(t_c, m, t_s)}{\sum_{t_s=T_j^L(t_c,1)}^{t_c} C_{T_j^L}(t_c, m, t_s)} & \text{otherwise} \end{cases}$$

$$C_{T_j}^L(t_c, m) = \frac{1}{t_c - T_j^L(t_c, 1) + 1} \sum_{t_s=T_j^L(t_c,1)}^{t_c} C_{T_j^L}(t_c, m, t_s)$$

$$T_j^L(t_c, m, t_s) = T_j^L(t_c, 1) - s_j(ts, m-1)$$

$$C_{T_j^L}(t_c, m, t_s) = C_{s_j}(t_s, m-1)$$

$$s_j(t_s, n) = \begin{cases} 0 & \text{if there is no } n\text{ th upper peak} \\ \arg_k \text{Get\_}[n]\text{th\_Upper\_Peak}(C_j(t_s, k)) & \text{otherwise} \end{cases}$$

$$C_{s_j}(t_s, n) = \begin{cases} 0 & \text{if there is no } n\text{ th upper peak} \\ C_j(t_s, s_j(t_s, u)) & \text{otherwise} \end{cases}$$

Here, $\arg_k \text{Get\_}_{[n]th}\text{\_Upper\_Peak}(C_j(t_s, k))$ is a function which outputs, where k is gradually changed from 0 to $\max(P_j)$ as illustrated in FIG. 10C, a value of k of a convex peak formed by the nth value of $C_j(t_s, k)$ In particular, the in-phase time estimation section 125 of the present example functions as an example of an in-phase time estimation section for estimating the in-phase time information and reliability of the in-phase time information using a result of the correlation analysis by the correlation analysis section 121 and the cycle predicted by the cycle prediction section 124. For example, the in-phase time estimation section 125 can estimate in-phase time information of the input time series signal of a phase same as that at the prediction target time and the reliability information of the in-phase time information, which are information effective to prevent the problem that the prediction accuracy of the control section 1 deteriorates using the input time series signal to the control section 1, the time series signal of the correlation analysis result of the input time series signal which is an output of the cache memory 122 and the time series information of the prediction result of the cycle of the input time series signal, which is an output of the cycle prediction section 124, till the prediction target time.

(1.4.6) Time Delay Section 126

The time delay section 126 outputs information whose time is delayed by an arbitrary period with respect to arbitrary input information having a time parameter.

The time delay section 126 illustrated in FIG. 5 receives, as an input thereto, prediction information $\{\tilde{P}(t_c, t_c+1)\}_{l=1}^L$ of the cycle from time ($t_c$+1) to prediction target time ($t_c$+L) which is an output of the cycle prediction section 124 and outputs $\{\tilde{P}(t_c-L, t_c-L+1)\}_{l=1}^L$ whose time parameter is delayed by L.

(1.4.7) Cache Memory 127

The cache memory 127 is a memory which stores time series information $\{\tilde{P}(t_c-L, t_c-L+1)\}_{l=1}^L$ of the prediction value of the cycle which is an output of the time delay section 126 and outputs an arbitrary one of pieces of information stored for a fixed period of time in the past.

The cache memory 127 illustrated in FIG. 5 outputs time series information $$\{\tilde{P}(\tau-L,\tau)\}_{\tau=2max(P_j)+L}^{t_c}$$

of the prediction result whose cycle prediction period is L from within the information cached in the past.

(1.4.8) Difference Processing Section 128

The difference processing section 128 illustrated in FIG. 5 carries out a difference process for $$\{P(\tau)\}_{\tau=2max(P_j)}^{t_c}$$

which is part of an output of the cycle estimation section 123 and $$\{\tilde{P}(\tau-L,\tau)\}_{\tau=2max(P_j)+L}^{t_c}$$

which is an output of the cache memory 127, and outputs time series information $$\{\Delta^L P(\tau)\}_{\tau=2max(P_j)+L}^{t_c} \equiv \{\|\tilde{P}(\tau-L,\tau) - P(\tau)\|\}_{\tau=2max(P_j)+L}^{t_c} \quad \text{[Expression 57]}$$

of a prediction error (accuracy) of the output of the cache memory 127.

In particular, the difference processing section 128 of the present example can estimate accuracy information of the predicted cycle using a cycle fluctuation estimated by the cycle estimation section 123 and a cycle predicted by the cycle prediction section 124.

(1.5) Variables Estimation Section 13

The variables estimation section 13 estimates variable quantities of arbitrary input information having a time parameter per unit time and outputs the variation quantities.

The variables estimation section 13 illustrated in FIG. 5 receives, as an input thereto, an input time series signal $$\{x(\tau)\}_{\tau=1}^{t_c}$$

to the control section 1 and outputs time series information of the variation per unit time estimated in accordance with the following expressions.

$$\{\Delta x(\tau)\}_{\tau=1}^{t_c}$$

$$\Delta x(\tau)=[\Delta x_1(\tau) \Delta x_2(\tau) \ldots \Delta x_{D_{in}}(\tau)] \quad \text{[Expression 58]}$$

$$\Delta x_j(\tau)=\|x_j(\tau+1)-x_j(\tau+1)\|/2 \quad \text{[Expression 59]}$$

(1.6) Cache Memory 14

The cache memory 14 is a memory for storing information $$I^{\tilde{x}}(t_c=L)$$

of an output calculation procedure which is an output of the model production section 11, and outputs an arbitrary one of pieces of information stored therein for a fixed period of time in the past.

The cache memory 14 illustrated in FIG. 5 outputs a time series $$\{I^{\tilde{x}}(\tau+L)\}_{\tau=1}^{t_c}$$

of all information stored therein after time $\tau$ till current time $t_c$.

(1.7) Cache Memory 15

The cache memory 15 is a memory for storing a prediction value $$\tilde{x}(t_c+L)$$

of the prediction target time ($t_c+L$) of the input time series signal to the control section 1 which is an output of the model production section 11, and outputs an arbitrary one of pieces of information stored for a fixed period of time in the past.

The cache memory 15 illustrated in FIG. 5 outputs a time series $$\{\tilde{x}(\tau+L)\}_{\tau=1}^{t_c}$$

of all information stored therein after time $\tau=1$ to current time $t_c$.

(1.8) Prediction Accuracy Estimation Section 16

The prediction accuracy estimation section 16 evaluates error transition and the effectiveness (contribution to the prediction) of the sub models 111-1 to 111-S in the prediction in the past and estimates the variation per unit time at the prediction target time of the input time series signal using an input time series signal to the control section 1, time series information of the variation per unit time of the input time series signal which is an output signal of the variables estimation section 13, time series information of the prediction value at the prediction target time of the input time series signal, which is an output of the model production section 11, and the calculation procedure of the prediction value, in-phase time information of a phase same as that at the prediction target time of an input time series signal, which is an output of the cycle fluctuation analysis section 12, and reliability information of the in-phase time information, and time series information of the prediction accuracy of the cycle fluctuation till the prediction target time. Then, the prediction accuracy estimation section 16 outputs the accuracy information of the prediction value at the prediction target time of the input time series signal and model design information for the sub models 111-1 to 111-S and the synthesis processing section 112 for optimum prediction at the target prediction time.

An idea of the prediction accuracy estimation section 16 which estimates accuracy information of the prediction value of the input time series signal at the prediction target time and model information for optimum prediction at the target prediction time is described below.

Generally, where the variation of a time series signal per unit time is great, the prediction accuracy is low, but where the variation is small, the prediction accuracy is high. Further, from the difference of the variation, also a type of a model and a parameter for model design which are suitable for prediction are difference. In particular, to estimate a variation per unit time of a time series signal at prediction target time can make significant information for estimating the prediction accuracy at the prediction target time and selecting a type of a model or a parameter for model design. Therefore, in the present example, time series information of the variation per unit time of an input time series signal which is an output of the variables estimation section 13 is used to estimate the variation per unit time of the time series signal at the prediction target time.

Further, generally in the case where a principal component of an input time series signal is seasonal dynamics, there is a fixed correlation between the prediction accuracy at the prediction target time and the prediction accuracy at time of the phase in the past same as the phase at the prediction target time. Therefore, the prediction accuracy estimation section 16 calculates a weighted average error in the case where various design parameters are used for the sub models 111-1 to 111-S and the synthesis processing section 112 from information of the input time series signal, prediction value of the input time series signal at the in-phase time, time series information of the calculation process of the prediction value and variation per unit time of the time series signal at the prediction target time estimated formerly, for example, in the case where the reliability of the in-phase time corresponding to the time at which the phase is same as that at the prediction target time of the input time series signal. Then, the prediction accuracy estimation section 16 uses information of the evaluation of the same and the variation per unit time of the time series signal at the prediction target time predicted formerly to estimate optimum model design information. Further, the prediction accuracy estimation section 16 determines a result of arbitrary correction carried out when necessary for the weighted average error corresponding to the optimum model design information as an estimated value of the accuracy information of the prediction value.

Figure 12A:
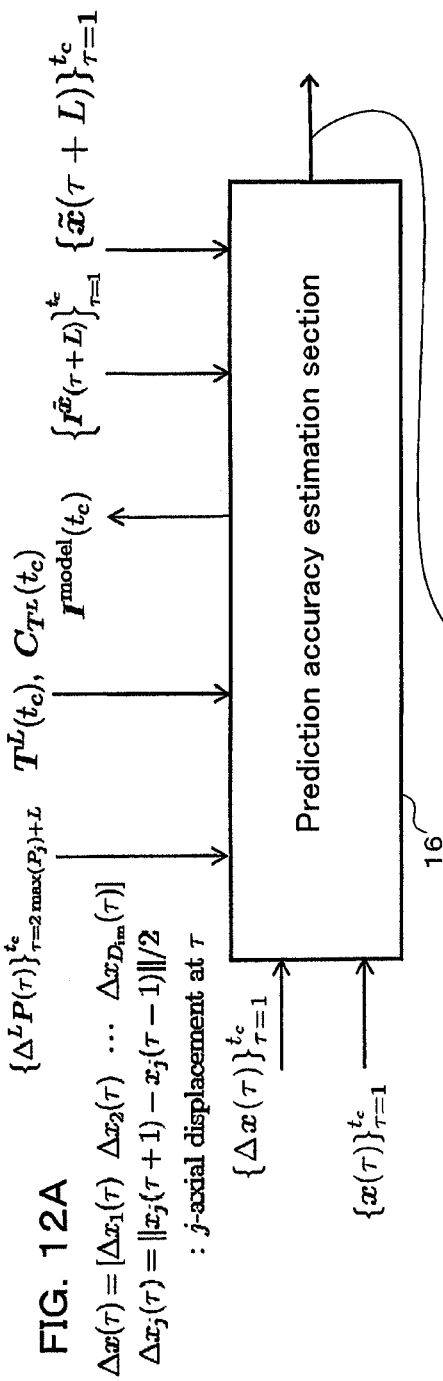
FIGS. 12A and 12B are views illustrating an example of operation of a prediction accuracy estimation section 16.

The prediction accuracy estimation section 16 illustrated in FIGS. 5 and 12A receives, as inputs thereto, an input time series signal $$\{x(\tau)\}_{\tau=1}^{t_c}$$

time series information $$\{\Delta x(\tau)\}_{\tau=1}^{t_c}$$

of the variation per unit time of an input time series signal which is an output of the variables estimation section 13, a time series signal $$\{\tilde{x}(\tau+L)\}_{\tau=1}^{t_c}$$

of the prediction value for an input time series signal till now, which is an output of the model production section 11, and time series information $$\{I^{\tilde{x}}(\tau=L)\}_{\tau=1}^{t_c}$$

of the calculation procedure of the time series information of the prediction value, in-phase time information $$T^L(t_c)$$

at the prediction target time of an input time series signal which is an output of the cycle fluctuation analysis section 12 and reliability information $$C_{T^L}(t_c)$$

of the in-phase time information, and time series information $$\{\Delta_L P(\tau)\}_{\tau=2max(P_j)+L}^{t_c}$$

of the prediction accuracy of the cycle fluctuation till the prediction target time, and outputs an estimated value $$\tilde{e}(t_c+L)=[\tilde{e}_1(t_c+L)\tilde{e}_2(t_c+L)\ldots\tilde{e}_{D_{im}}(t_c+L)] \quad \text{[Expression 60]}$$

of the prediction error which is accuracy information of the prediction value at the prediction target time of the input time series signal, an estimated value $$\Delta\tilde{x}(t_c+L)=[\Delta\tilde{x}_1(t_c+L)\Delta\tilde{x}_2(t_c+L)\ldots\Delta\tilde{x}_{D_{im}}(t_c+L)] \quad \text{[Expression 61]}$$

of the variation per unit time of the time series signal, and model design information $$I^{model}(t_c)$$

of the submodels 111-1 to 111-S and the synthesis processing section 112 for optimum prediction at the prediction target time.

For example, first, an error at the prediction target time of the input time series signal and an estimated value of the variation per unit time of the input time series signal with regard to a uth candidate $$I_{cand}^{model}(u), u=1,2,\ldots,U$$

from among U different kinds of model design information candidates prepared arbitrarily are defined in the following manner.

$$\tilde{e}_j^{cand}(t_c+L,u)=F_j^e(I_{cand}^{model}(u),\text{ALL\_Input}(t_c)) \quad \text{[Expression 62]}$$

$$\Delta\tilde{x}_j^{cand}(t_c+L,u)=F_j^{\Delta\tilde{x}}(I_{cand}^{model}(u),\text{ALL\_Input}(t_c)) \quad \text{[Expression 63]}$$

Here, $$F_j^e(\bullet)$$

and $$F_j^{\Delta\tilde{x}}(\bullet)$$

are functions which rely upon the sub models 111-1 to 111-S and the synthesis processing section 112, respectively, and an argument $$\text{ALL\_Input}(t_c)=\{\{x(\tau)\}_{\tau=1}^{t_c}\cdot\{\Delta x(\tau)\}_{\tau=1}^{t_c}\cdot\{\tilde{x}(\tau+L)\}_{\tau=1}^{t_c}\cdot\{I^{\tilde{x}}(\tau+L)\}_{\tau=1}^{t_c}\cdot T^L(t_c)\cdot C_{T^L}(t_c)\cdot\{\Delta_L P(\tau)\}_{\tau=2max(P_j)+L}^{t_c}\} \quad \text{[Expression 64]}$$

of the functions is all input information to the cache memory 15.

Then, a number $$u^c=\arg_u\min(\|\tilde{e}^{cand}(t_c+L,u)\|) \quad \text{[Expression 65]}$$

of a candidate which exhibits a minimum prediction error from among all candidates is selected. However, $$\tilde{e}^{cand}(t_c+L,u)=[\tilde{e}_1^{cand}(t_c+L,u)\tilde{e}_2^{cand}(t_c+L,u)\ldots\tilde{e}_{Dim}^{cand}(t_c+L,u)] \quad \text{[Expression 66]}$$

From this number of the selected candidate, model design information is determined as given by $$I^{model}(t_c)=I_{cand}^{model}(u^c) \quad \text{[Expression 67]}$$

and also the error at the prediction target time and the estimated value of the variation per unit time of the time series signal are determined in the following manner.

$$\tilde{e}_j(t_c+L)=c_e\cdot\tilde{e}_j^{cand}(t_c+L,u^c) \quad \text{[Expression 68]}$$

$$\Delta\tilde{x}_j(t_c+L)=c_{\Delta\tilde{x}_j}\cdot\Delta\tilde{x}_j^{cand}(t_c+L,u^c) \quad \text{[Expression 69]}$$

Here, $$c_e$$

and $$c_{\Delta\tilde{x}_j}$$

are individually arbitrary constants.

Further, in order to indicate a more particular example, it is assumed that the number S of the sub models 111-1 to 111-S is 1. In this instance, an error at the prediction target time and an estimated value of the variation per unit time of the time series signal may be determined, for example, using a weighted average amount of the actually measured value in the proximity of the time at which the input time series has a phase same as that at the prediction target time of the input time series signal, as given by the following expressions.

$$\tilde{e}_j(t_c+L) = \begin{cases} \max(e_j) & \ldots \text{ if } \upsilon_j(t_c)=0 \\ \sum_{m=1}^{M'}\sum_{d\in S_{\Delta_L P_j}(T_j^L(t_c,m))}C_{\Delta_L P_j}(d)\times \\ \prod_{k=1}^{Dim}I_k^{\tilde{x}}(T_k^L(t_c,m)+d+L,1,1)\times & \ldots \text{ otherwise} \\ F^{e_j}(T_j^L(t_c,m)+d)C_{T_j^L}(t_c,m)\times \\ e_j(T_j^L(t_c,m)+d)/\upsilon_j(t_c) \end{cases} \quad \text{[Expression 70]}$$

-continued $$\Delta \tilde{x}_j(t_c + L) = \qquad \text{[Expression 71]}$$

$$\begin{cases} \max(\Delta x_j) & \ldots \text{ if } \upsilon_j(t_c) = 0 \\ \sum_{m=1}^{M} \sum_{d \in S_{\Delta L_{P_j}}(T_j^L(t_c, m))} C_{\Delta L_{P_j}}(d) \times \\ \prod_{k=1}^{Dim} I_k^{\tilde{x}}(T_k^L(t_c, m) + d + L, 1, 1) \times & \ldots \text{ otherwise} \\ F^{ej}(T_j^L(t_c, m) + d) C_{T_j^L}(t_c, m) \times \\ \Delta x_j^I(T_j^L(t_c, m) + d)/\upsilon_j(t_c) \end{cases}$$

$$\upsilon_j(t_c) \equiv \sum_{m=1}^{M_T} \sum_{d \in S_{\Delta L_{P_j}}(T_j^L(t_c, m))} C_{\Delta L_{P_j}}(d) \times \qquad \text{[Expression 72]}$$

$$\prod_{k=1}^{Dim} I_k^{\tilde{x}}(T_k^L(t_c, m) + d + L, 1, 1) \times$$

$$F^{ej}(T_j^L(t_c, m) + d) C_{T_j^L}(t_c, m)$$

$$F^{ej}(\tau) = \begin{cases} 0 & \ldots \text{ if } \|e_j(\tau)\| > \max(e_j) \\ 1 & \ldots \text{ otherwise} \end{cases} \qquad \text{[Expression 73]}$$

$$e_j(\tau) \equiv \|x_j(\tau) - \tilde{x}_j(\tau)\| \quad \tau = L+1, L+2, \ldots, t_c \qquad \text{[Expression 74]}$$

Figure 12B:
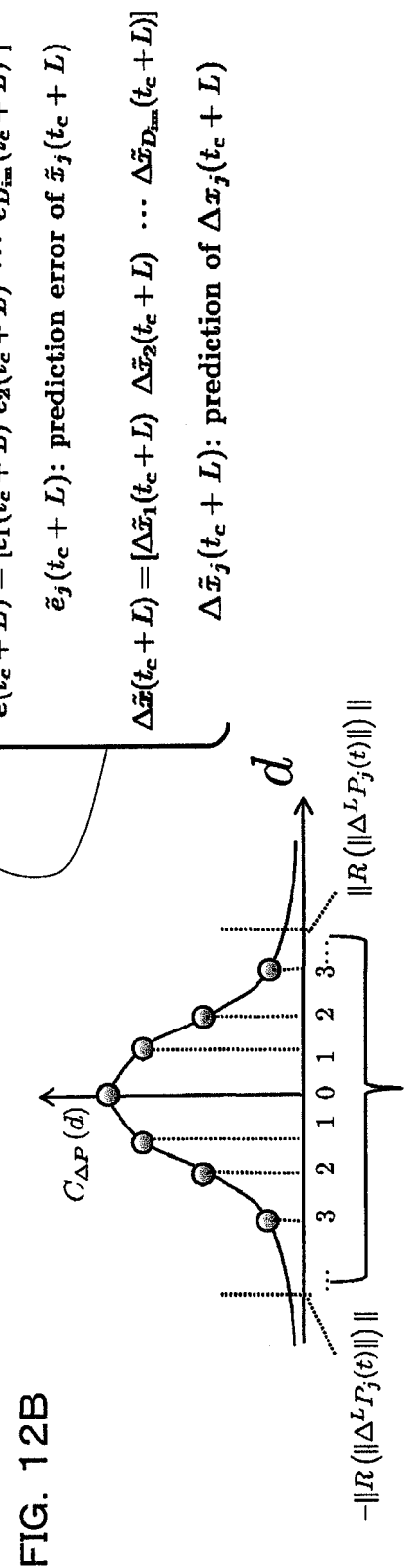

Here, max($e_j$)

and max($\Delta x_j$)

are estimated values of the error which may appear in ordinary prediction for the input time series signal and a maximum value of the variation per unit time of the time series signal. Further, a function $C_{\Delta L_{P_j}}(d)$ illustrated in FIG. 12B is a arbitrary weight function which takes an influence of the error of the cycle prediction at the prediction target time into consideration, and an argument d of the function is determined as given by the following expression.

$$d \in S_{\Delta L_{P_j}}(t) = \{x \in Z | x \leq \|R(\|\Delta^L P_j(t)\|)\|\} \qquad \text{[Expression 75]}$$

Here

Z is a set of integers, and

R(•)

is a function which rounds an input and outputs the rounded input.

Meanwhile, as another particular example, an error at the prediction target time and an estimated value of the variation per unit time of the time series signal may be calculated, using a weighted average amount of the actually measured value in the proximity of time in the past which is a neighboring point with the position of the prediction target time from within a locus of the input time series signal, as given by the following expressions.

$$\tilde{e}_j(t_r + L) = \qquad \text{[Expression 76]}$$

$$\begin{cases} \max(e_j) & \ldots \text{ if } w_j(t_c) = 0 \\ \sum_{i \in A_L(t_c, \delta_e)} \sum_{d \in S_{\Delta L_{P_j}}(i)} C_{\Delta L_{P_j}}(d) \times \\ \prod_{k=1}^{Dim} I_k^{\tilde{x}}(i + d, 1, 1) F^{ej}(i + d) \times & \ldots \text{ otherwise} \\ e_j(i + d)/w_j(t_c) \end{cases}$$

$$\Delta \tilde{x}_j(t_c | L) = \qquad \text{[Expression 77]}$$

$$\begin{cases} \max(\Delta x_j) & \ldots \text{ if } w_j(t_c) = 0 \\ \sum_{i \in A_L(t_c, \delta_e)} \sum_{d \in S_{\Delta L_{P_j}}(i)} C_{\Delta L_{P_j}}(d) \times \\ \prod_{k=1}^{Dim} I_k^{\tilde{x}}(i + d, 1, 1) F^{ej}(i + d) \times & \ldots \text{ otherwise} \\ \Delta x_j^I(i + d)/w_j(t_c) \end{cases}$$

$$w_j(t_c) \equiv \qquad \text{[Expression 78]}$$

$$\sum_{i \in A} \sum_{d \in S_{\Delta L_{P_j}}(i)} C_{\Delta L_{P_j}}(d) \prod_{k=1}^{Dim} I_k^{\tilde{x}}(i + d, 1, 1) F^{ej}(i + d)$$

$$A_L(t_c, \delta_e) = \qquad \text{[Expression 79]}$$
$$\{\tau | \tau = 1, 2, \ldots, t_c, \Lambda \|x(\tau) - \bar{x}(tc + L)\| < \delta_e\}$$

Here, $\delta_e$ is an arbitrary positive constant.

It is to be noted that, in the case where the number S of the sub models 111-1 to 111-S is 1 and particulars of the model are decided uniquely as in the particular examples described above, $$I^{model}(t_c) = 0 \qquad \text{[Expression 80]}$$

may be applied.

In particular, the prediction accuracy estimation section 16 of the present example functions as a prediction accuracy estimation section adapted to estimate model design information for predicting a value of the input time series signal after the predetermined time and accuracy of the prediction of the value of the input time series signal after the predetermined time based on the model design information using the input time series signal, the time series information of a variation per unit time of the input time series signal and the in-phase time information and reliability of the in-phase time information calculated by the cycle fluctuation analysis section 12.

Further, the prediction accuracy estimation section 16 of the present example can estimate accuracy information of the prediction value of the input time series signal at the prediction target time and model design information of the sub models 111-1 to 111-S and the synthesis processing section 112 for optimum prediction of the target prediction time by evaluating the effectiveness of the error transition and the sub models 111-1 to 111-S in the prediction in the past using the input time series signal to the control section 1, the time series information of the variation per unit time of an input time series signal which is an output of the variables estimation section 13, the time series information of the prediction value at the prediction target time of an input time series signal which is an output of the model production section 11 and the calculation procedure of the prediction value, and the time series information of the in-phase time information of the same phase as the phase at the prediction target time of an input time series signal which is an output signal of the cycle fluctuation analysis section 12 and the reliability information of the in-phase time information and the prediction accuracy of the cycle fluctuation till the prediction target time, and by estimating the variation per unit time of the input time series at the prediction target time.

Further, the prediction accuracy estimation section 16 can estimate the model design information using information regarding the calculation procedure of the value of the input time series signal after the predetermined time, which is outputted from the model production section 11.

Further, the prediction accuracy estimation section 16 can estimate prediction accuracy information in the case where the value of the input time series signal after the predetermined time is predicted using the prediction mode described hereinabove.

(1.9) Example of Flow of the Present Control

Here, an example of a flow of the control described above is described with reference to flow charts illustrated in FIGS. 19 to 28.

Figure 19:
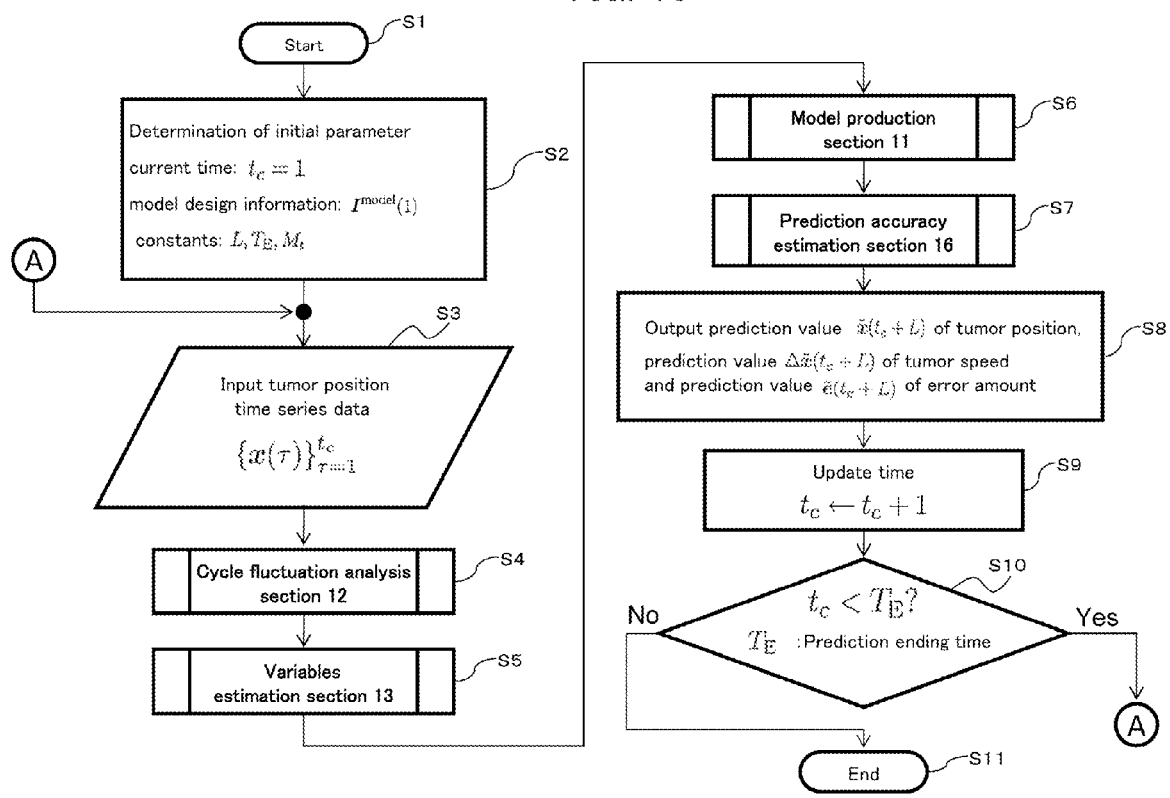
FIG. 19 is a flow chart illustrating an example of a prediction method of the present example.

First, as illustrated in FIG. 19, after the control described above is started (step S1), the control section 1 determines initial parameters to be used for prediction of an input time series signal after the predetermined time (step S2). The initial parameters include, for example, $t_c=1$ as the current time, $$I^{model}(1)$$

as the model design information, and L, $T_E$ and $M_t$ as constants. Here, $T_E$ represents the prediction target time.

Then, if, for example, as time series data of the tumor position, an input time series signal $$\{x(\tau)\}_{\tau=1}^{t_c}$$

is inputted to the control section 1 (step S3), then the control section 1 switches over processing thereof to the cycle fluctuation analysis section 12 (step S4).

Figure 20:
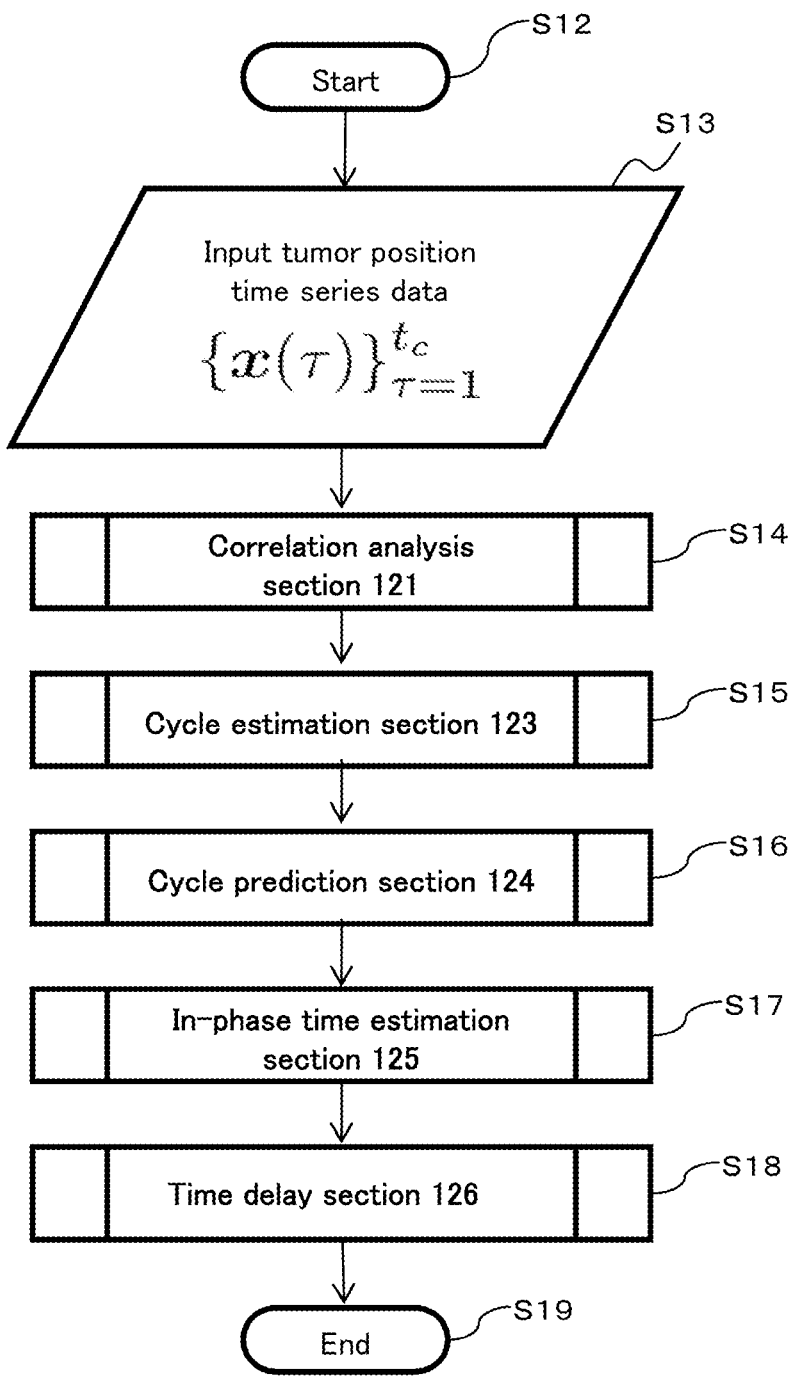
FIG. 20 is a flow chart illustrating another example of the prediction method of the present example.

After the processing is switched over to the cycle fluctuation analysis section 12 at step S4, the cycle fluctuation analysis section 12 starts processing thereof as illustrated in FIG. 20 (step S12).

Then, if the input time series signal $$\{x(\tau)\}_{\tau=1}^{t_c}$$

is inputted, for example, as time series data of the tumor position from the control section 1 (step S13), then the cycle fluctuation analysis section 12 successively switches over the processing to the correlation analysis section 121, cycle estimation section 123, cycle prediction section 124, in-phase time estimation section 125 and time delay section 126 (steps S14 to S18), and then the processing by the cycle fluctuation analysis section 12 is ended (step S19).

Figure 21:
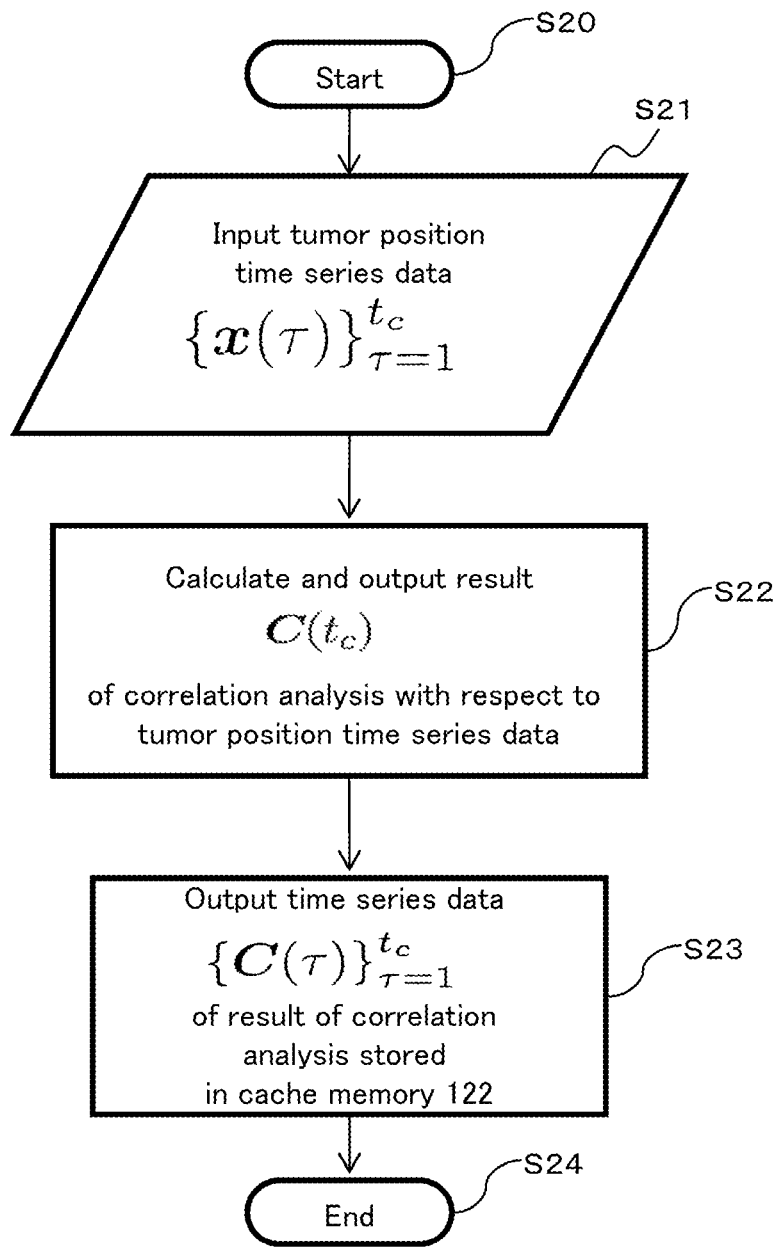
FIG. 21 is a flow chart illustrating a further example of the prediction method of the present example.

When the processing is switched over to the correlation analysis section 121 at step S14, the correlation analysis section 121 starts processing thereof as illustrated in FIG. 21 (step S20).

Then, if the input time series signal $$\{x(\tau)\}_{\tau=1}^{t_c}$$

is inputted, for example, as time series data of the tumor position from the control section 1 (step S21), then the correlation analysis section 121 calculates and outputs a result $$C(t_c)$$

of a correlation analysis between part of the input time series signal and the input time series signal (step S22).

Further, the correlation analysis section 121 outputs the time series data $$\{C(\tau)\}_{\tau=1}^{t_c}$$

of the result of the correlation analysis stored in the cache memory 122 (step S23), and then the processing by the correlation analysis section 121 is ended (step S24).

Figure 22:
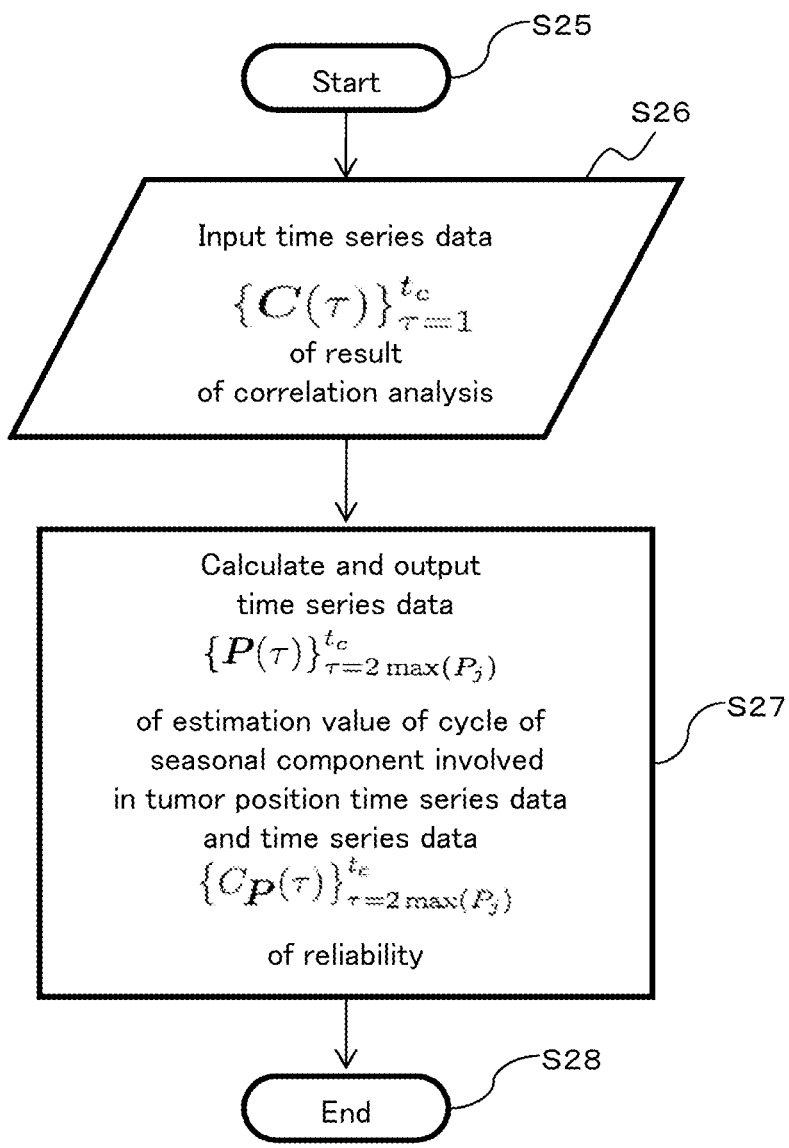
FIG. 22 is a flow chart illustrating a still further example of the prediction method of the present example.

Then, if the processing is changed over to the cycle estimation section 123 at step S15, then the cycle estimation section 123 starts processing thereof as illustrated in FIG. 22 (step S25).

Then, if the time series data $$\{C(\tau)\}_{\tau=1}^{t_c}$$

for example, of the result of the correlation analysis is inputted from the correlation analysis section 121 (step S26), then the cycle estimation section 123 calculates and outputs time series data $$\{P(\tau)\}_{\tau=2max(P_j)}^{t_c}$$

of the estimated value of the cycle of a seasonal component involved in the input time series signal and time series data $$\{C_P(\tau)\}_{\tau=2max(P_j)}^{t_c}$$

of the reliability value of the time series data of the estimated value (step S27), and then the processing by the cycle estimation section 123 is ended (step S28).

Figure 23:
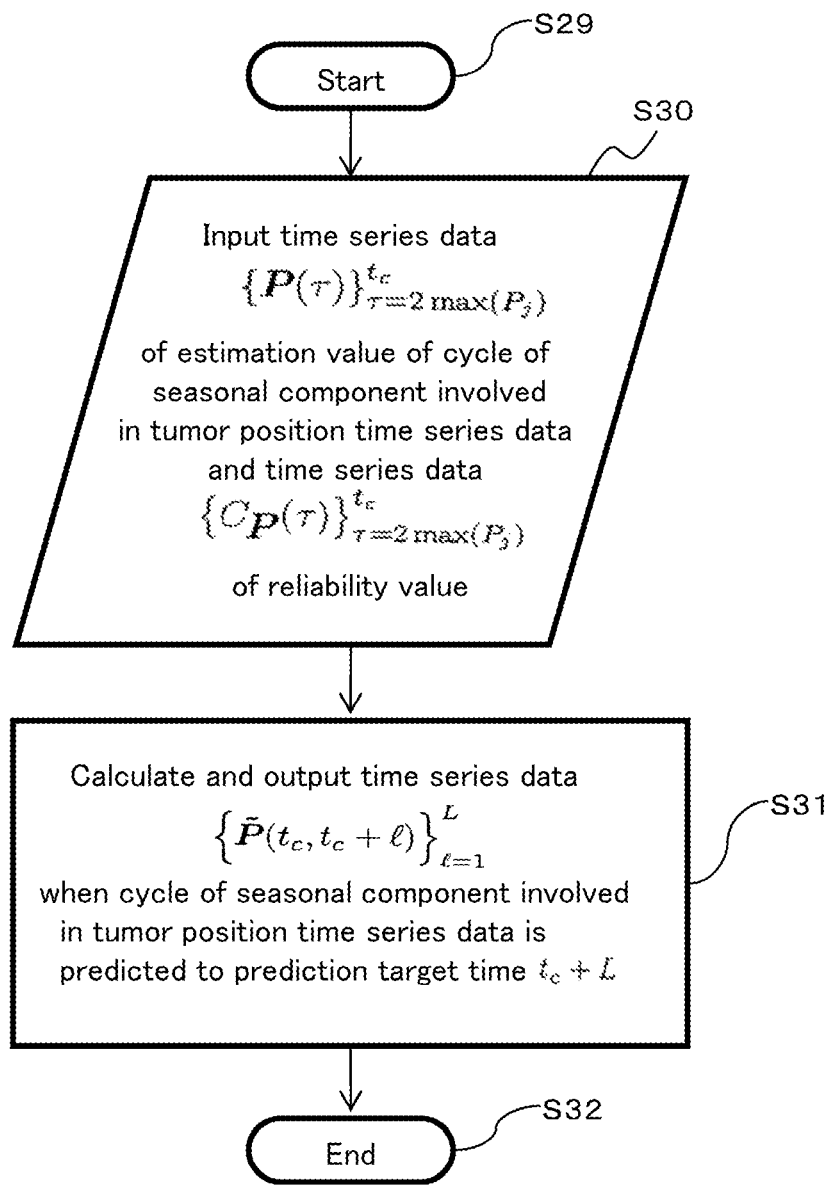
FIG. 23 is a flow chart illustrating a yet further example of the prediction method of the present example.

Then, if the processing is switched over to the cycle prediction section 124 at step S16, then the cycle prediction section 124 starts processing thereof as illustrated in FIG. 23 (step S29).

Then, if the time series data $$\{P(\tau)\}_{\tau=2max(P_j)}^{t_c}$$

of the estimated value of the cycle of the seasonal component involved in the input time series signal described hereinabove and the time series data $$\{C_P(\tau)\}_{\tau=2max(P_j)}^{t_c}$$

of the reliability value of the time series data of the estimated value are inputted from the cycle estimation section 123 (step S30), then the cycle prediction section 124 calculates and outputs time series data $$\{\tilde{P}(t_c,t_c+l)\}_{l=1}^{L}$$

obtained by prediction of the cycle of the seasonal component involved in the input time series signal till the prediction target time ($t_c+L$) (step S31), and then the processing by the cycle prediction section 124 is ended (step S32).

Figure 24:
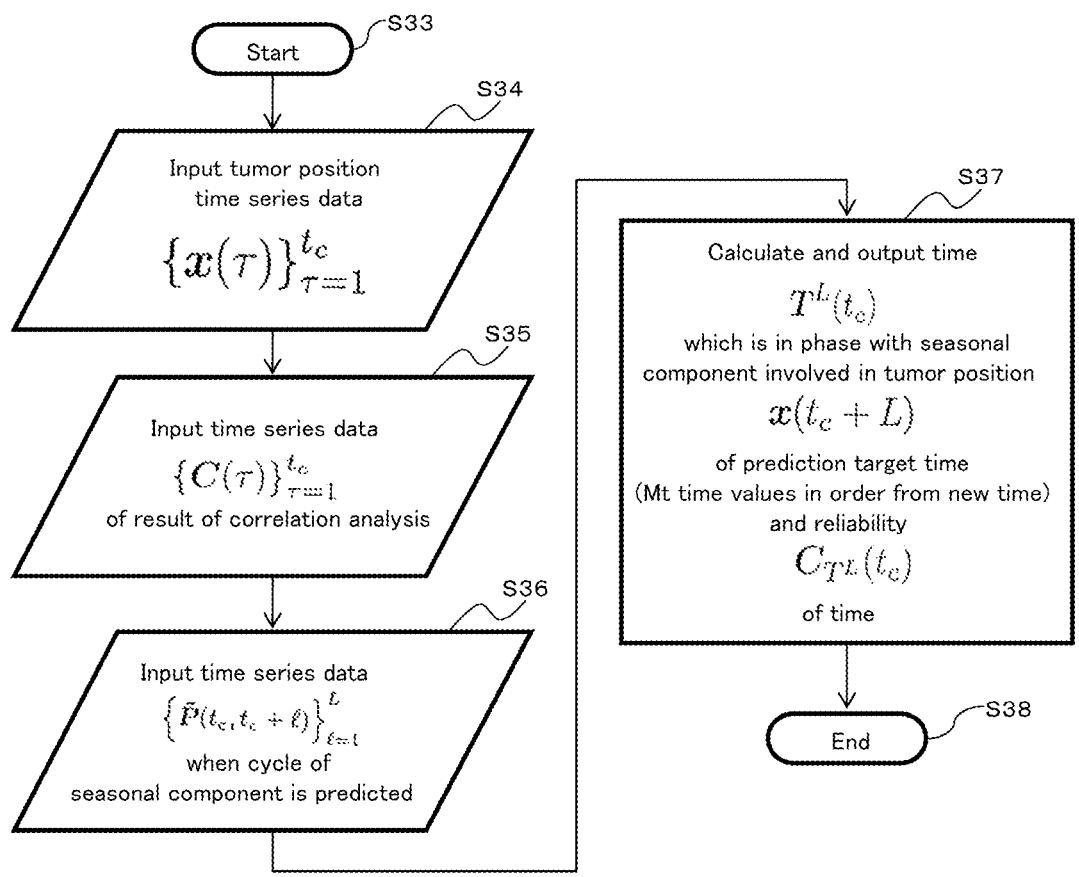
FIG. 24 is a flow chart illustrating a yet further example of the prediction method of the present example.

Then, when the processing is switched over to the in-phase time estimation section 125 at step S17, the in-phase time estimation section 125 starts processing thereof as illustrated in FIG. 24 (step S33).

Then, when the in-phase time estimation section 125 receives, as an input thereto, the input time series signal $$\{x(\tau)\}_{\tau=1}^{t_c}$$

for example, as time series data of the tumor position, from the control section 1 (step S34) and further receives, as another input thereto, the time series data $$\{C(\tau)\}_{\tau=1}^{t_c}$$

of the result of the correlation analysis from the correlation analysis section 121 (step S35) and besides receives, as a further input thereto, the time series data $$\{\tilde{P}(t_c,t_c+l)\}_{l=1}^{L}$$

of the cycle prediction result from the cycle prediction section 124 (step S36), the in-phase time estimation section 125 calculates and outputs time at which the phase is same as that of the seasonal component involved in the input time series signal (for example, the tumor position at the prediction target time or the like)

$$x(t_c+L)$$

at the prediction target time $$T^L(t_c)$$

and the reliability $$C_{T^L}(t_c)$$

of the time of the same phase (step S37), and the processing by the in-phase time estimation section 125 is ended (step S38). It is to be noted that, for example, $M_t$ values of the time at which the phase is same as that of the seasonal component involved in the input time series signal $$x(t_c+L)$$

at the prediction target time may be calculated in order, for example, from the newest one.

Figure 25:
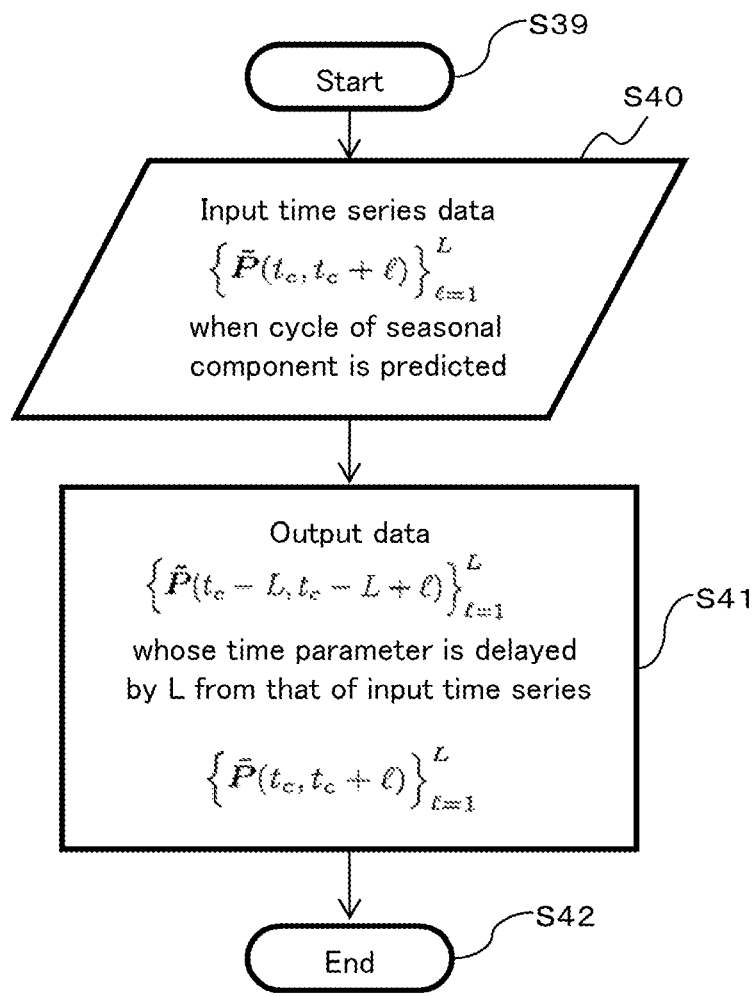
FIG. 25 is a flow chart illustrating a yet further example of the prediction method of the present example.

Then, when the processing is switched over to the cycle fluctuation analysis section 12 at step S18, the time delay section 126 starts processing thereof as illustrated in FIG. 25 (step S39).

Then, if the time series data $$\{\tilde{P}(t_c,t_c+l)\}_{l=1}^L$$

of the cycle prediction result is inputted from the cycle prediction section 124 (step S40), then the time delay section 126 calculates and outputs $$\{\tilde{P}(t_c,t_c+l)\}_{l=1}^L$$

in which the time parameters of the input time series $$\{\tilde{P}(t_c-L,t_c-L+l)\}_{l=1}^L$$

are delayed by L (step S41), and the processing by the time delay section 126 is ended (step S42).

After the processing by the cycle fluctuation analysis section 12 comes to an end, referring back to FIG. 19, the control section 1 switches over the processing to the variables estimation section 13 (step S5).

Figure 26:
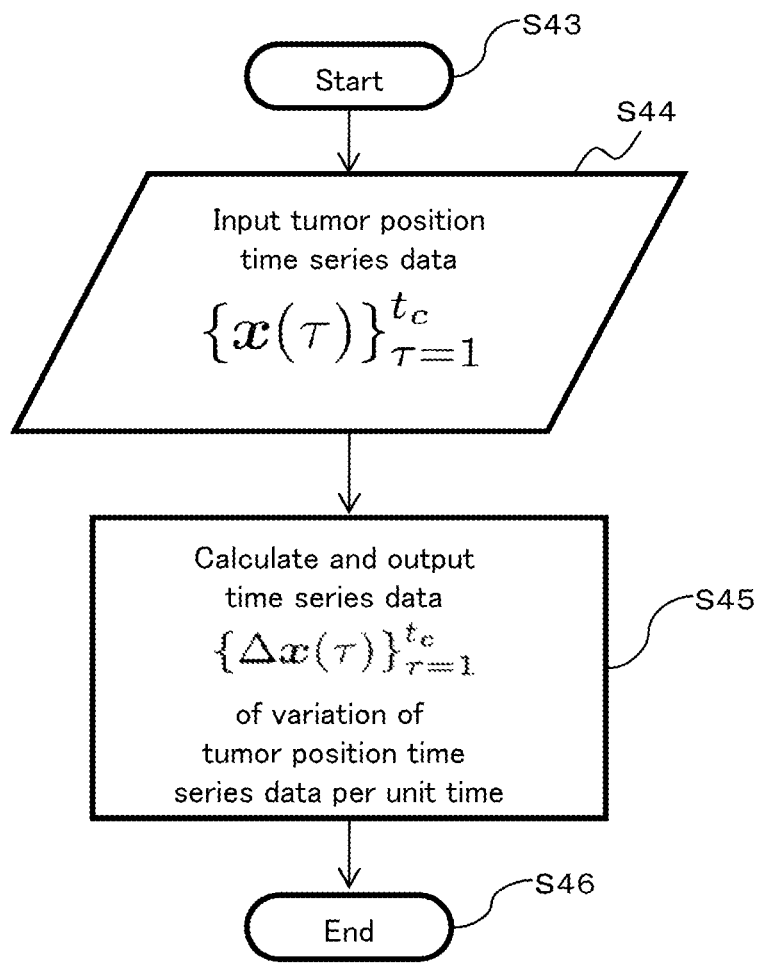
FIG. 26 is a flow chart illustrating a yet further example of the prediction method of the present example.

After the processing is switched over to the variables estimation section 13 at step S5, the variables estimation section 13 starts processing thereof as illustrated in FIG. 26 (step S43).

Then, if the input time series signal $$\{x(\tau)\}_{\tau=1}^{t_c}$$

is inputted, for example, as the time series data of the tumor position, from the control section 1 (step S44), then the variables estimation section 13 calculates and outputs time series data $$\{\Delta x(\tau)\}_{\tau=1}^{t_c}$$

of the variation per unit time of the input time series signal (step S45), and then the processing by the variables estimation section 13 is ended (step S46).

After the processing by the variables estimation section 13 comes to an end, referring back to FIG. 19, the control section 1 switches over the processing to the model production section 11 (step S6).

Figure 27:
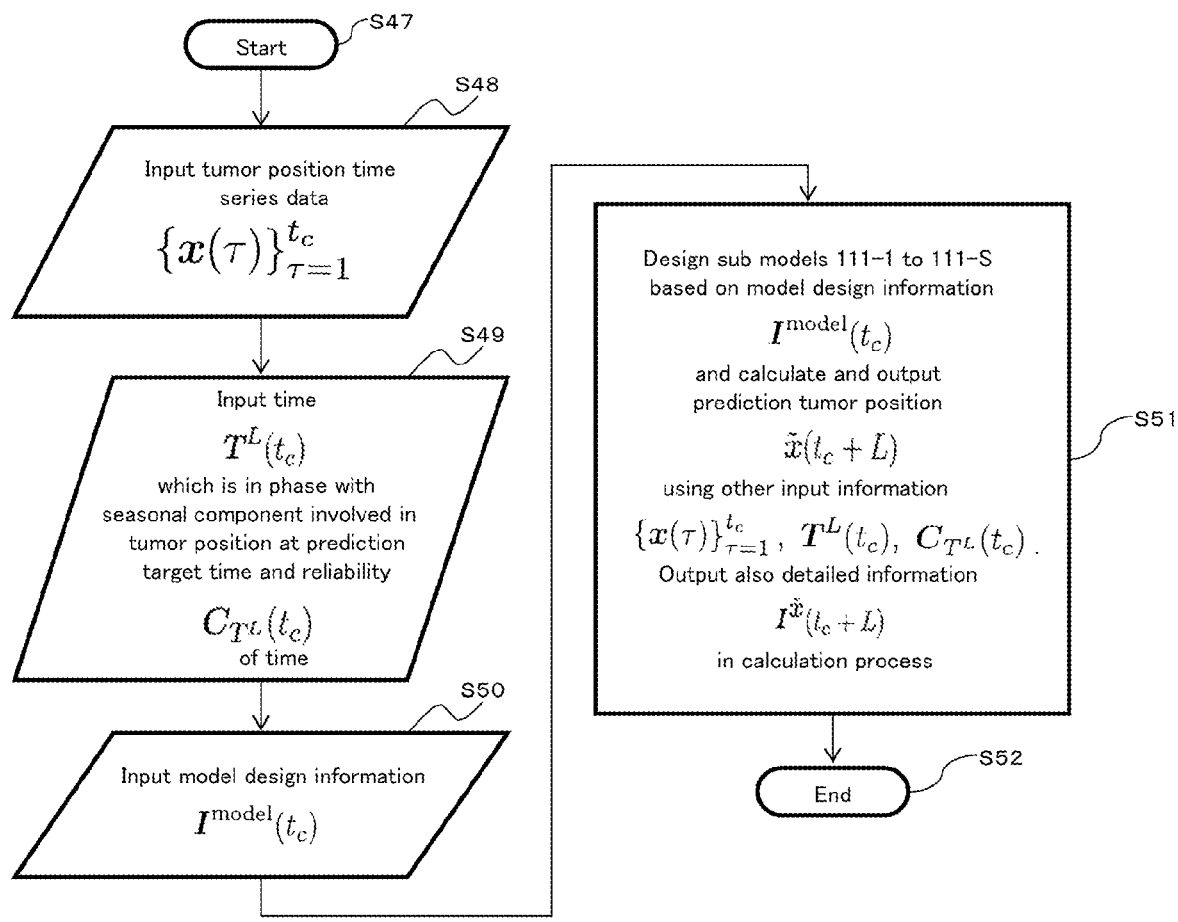
FIG. 27 is a flow chart illustrating a yet further example of the prediction method of the present example.

After the processing is switched over to the model production section 11 at step S6, the model production section 11 starts processing thereof as illustrated in FIG. 27 (step S47).

Then, if the model production section 11 receives, as an input thereto, the input time series signal $$\{x(\tau)\}_{\tau=1}^{t_c}$$

for example, as time series data of the tumor position, from the control section 1 (step S48) and receives, as inputs thereto, the time $$T^L(t_c)$$

at which the phase is same as that of the seasonal component involved in the input time series signal (for example, the tumor position at the prediction target time and so forth)

$$x(t_c+L)$$

at the prediction target time and the reliability $$C_{T^L}(t_c)$$

of the time from the in-phase time estimation section 125 (step S49) and besides receives, as an input thereto, the model design information $$I^{model}(t_c)$$

from the control section 1 (step S6), then the model production section 11 designs the sub models 111-1 to 111-S based on the model design information $$I^{model}(t_c)$$

and uses the other input information $$\{x(\tau)\}_{\tau=1}^{t_c}$$

$$T^L(t_c)$$

and $$C_{T^L}(t_c)$$

to calculate the prediction time series signal (for example, the predicted tumor position and so forth)

$$\tilde{x}(t_c+L)$$

of the input time series signal after the predetermined time and outputs the calculated prediction time series signal, and then outputs $$I^{\tilde{x}}(t_c+L)$$

as detailed information regarding the calculation procedure (step S51), whereafter the processing by the model production section 11 is ended (step S52).

After the processing by the model production section 11 comes to an end, referring back to FIG. 19, the control section 1 switches over the processing to the prediction accuracy estimation section 16 (step S7).

Figure 28:
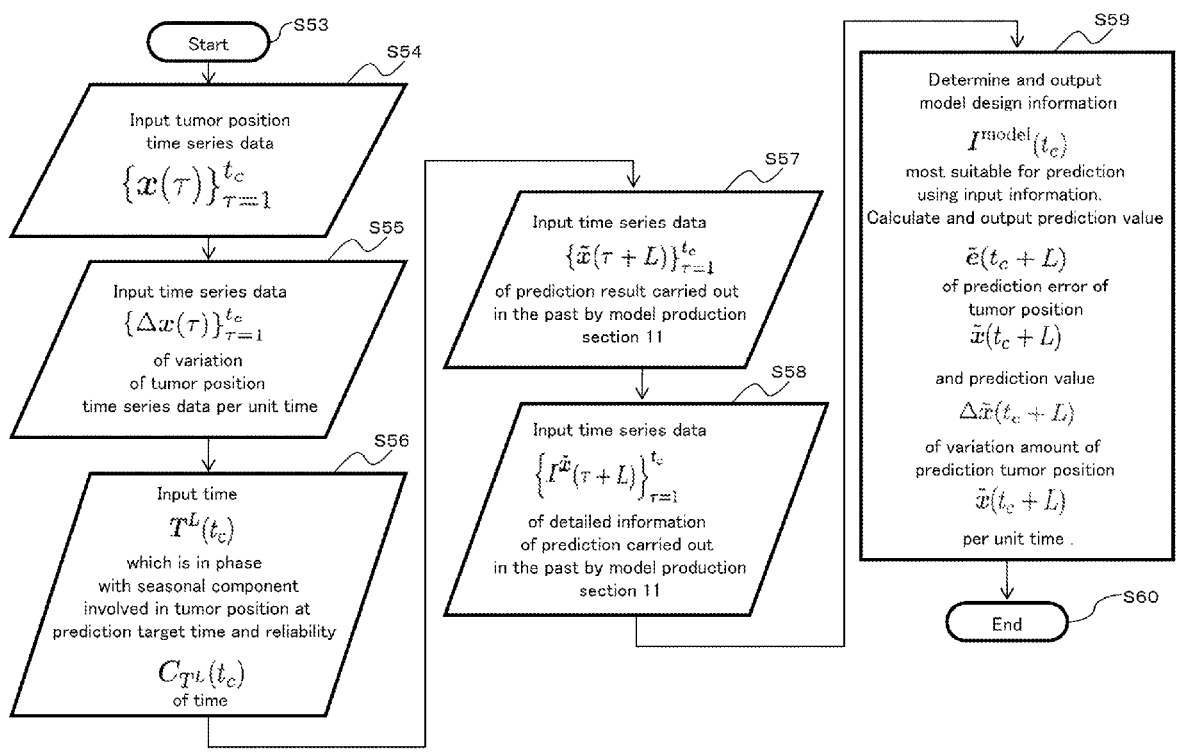
FIG. 28 is a flow chart illustrating a yet further example of the prediction method of the present example.

After the processing is switched over to the prediction accuracy estimation section 16 at step S7, the prediction accuracy estimation section 16 starts processing thereof as illustrated in FIG. 28 (step S53).

Then, if the prediction accuracy estimation section 16 receives, as an input thereto, the input time series signal $$\{x(\tau)\}_{\tau=1}^{t_c}$$

for example, as the time series data of the tumor position, from the control section 1 (step S54), receives, as inputs thereto, the time series data $$\{\Delta x(\tau)\}_{\tau=1}^{t_c}$$

of the variation per unit time of the input time series signal from the variables estimation section 13 (step S55), receives, as inputs thereto, time $$T^L(t_c)$$

and the reliability $$C_{T^L}(t_c)$$

of the time at which the phase is same as that of the seasonal component involved in the input time series signal (for example, the tumor position at the prediction target time and so forth)

$$x(t_c+L)$$

at the prediction target from the in-phase time estimation section 125 (step S56) and receives, as inputs thereto, the time series data $$\{\tilde{x}(\tau+L)\}_{\tau=1}^{t_c}$$

of the prediction result carried out in the past and detailed information $$\{I^{\tilde{x}(\tau+L)}\}_{\tau=1}^{t_c}$$

regarding the calculation procedure of the prediction from the model production section 11 through the cache memory 14 and the cache memory 15 (steps S57 and S58), then the prediction accuracy estimation section 16 determines and outputs model design information $$I^{model}(t_c)$$

optimum for prediction using the input information mentioned hereinabove and calculates and outputs the prediction value $$\tilde{e}(t_c+L)$$

of the error of the predicted tumor position $$\tilde{x}(t_c+L)$$

and the prediction value $$\Delta\tilde{x}(t_c+L)$$

of the variation per unit time at the predicted tumor position $$\tilde{x}(t_c+L)$$

(step S59), and then the processing by the prediction accuracy estimation section 16 is ended (step S60).

After the processing by the prediction accuracy estimation section 16 comes to an end, referring back to FIG. 19, the control section 1 outputs the prediction value $$\tilde{x}(t_c+L)$$

of the tumor position, the prediction value (prediction value of the tumor speed)

$$\Delta\tilde{x}(t_c+L)$$

of the variation per unit time at the predicted tumor position $$\tilde{x}(t_c+L)$$

and the prediction value $$\tilde{e}(t_c+L)$$

of the error of the predicted tumor position (step S8).

Then, the control section 1 increments the preset time $t_c$ to update the time (step S9) and decides whether or not the updated time is smaller than prediction end time $T_E$ (step S10).

Here, in the case where the control section 1 decides that the updated time is smaller than the prediction end time $T_E$ (Yes route at step S10), the processes at steps S3 to S9 in FIG. 19 are repeated.

On the other hand, if the control section 1 decides that the updated time is greater than the prediction end time $T_E$ (No route at step S10), then the prediction process is ended (step S11).

(1.10) Experiment Example

The effectiveness of the prediction function by the control section 1 described above is described based on an example of an experiment in which a time series signal of the observation position of an actual affected area 260 is used.

Figure 13:
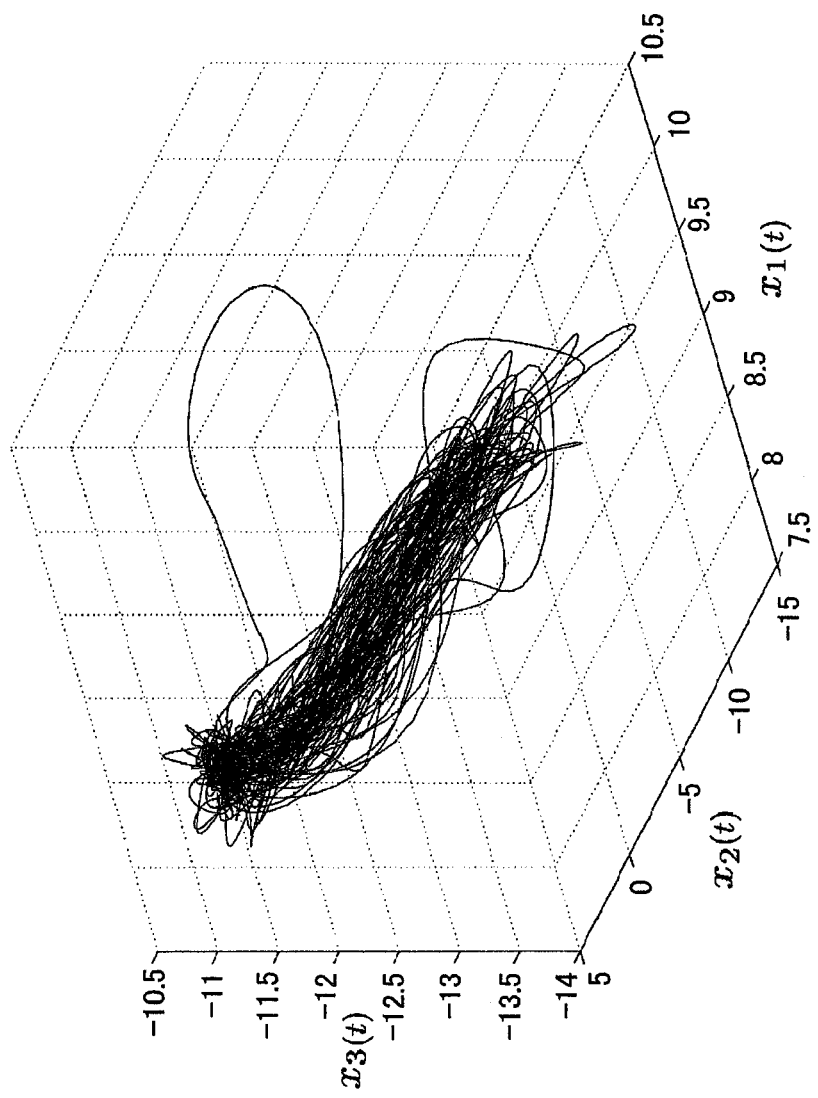
FIG. 13 is a view illustrating a three-dimensional plot of a predetermined observation position of an affected area 260.
Figure 14:
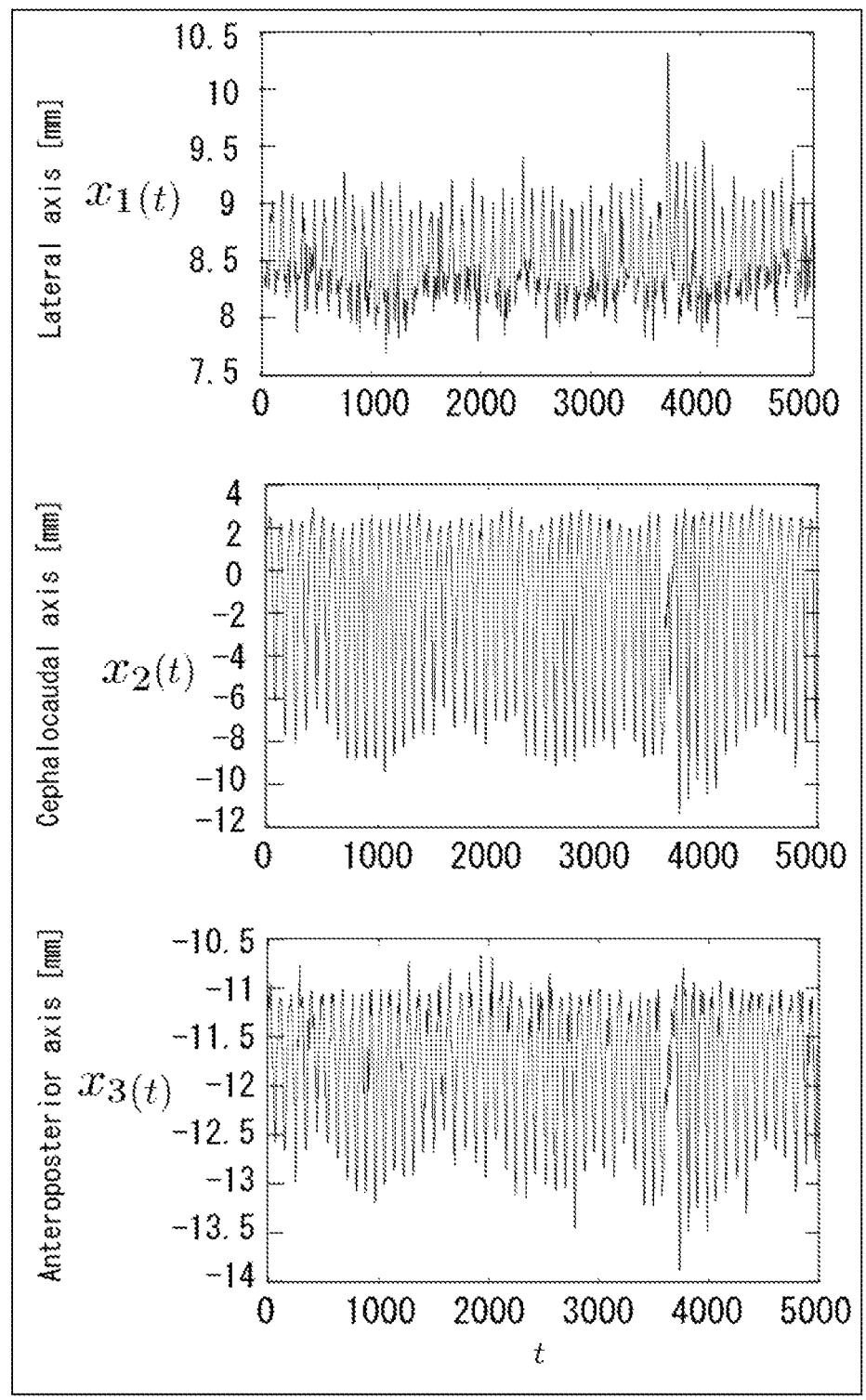
FIG. 14 is a view illustrating axial components of the three-dimensional plot illustrated in FIG. 13.

FIG. 13 is a view of the time series signal of an observation position of a certain affected area 260 plotted on a three-dimensional space. Further, if components of the time series signal for individual three-dimensional directions are represented as a graph, then such a time series signal as illustrated in FIG. 14 is obtained. Here, the scale of the axis of ordinate is millimeter (mm) and the scale of the axis of abscissa is 0.33 seconds/step. From FIG. 13, it can be seen that a principal component of the input time series signal is seasonal dynamics whose behavior is monotonous and stable. It is to be noted that it is found by a correlation analysis that the cycle of the input time series signal is time-variable.

Figure 15:
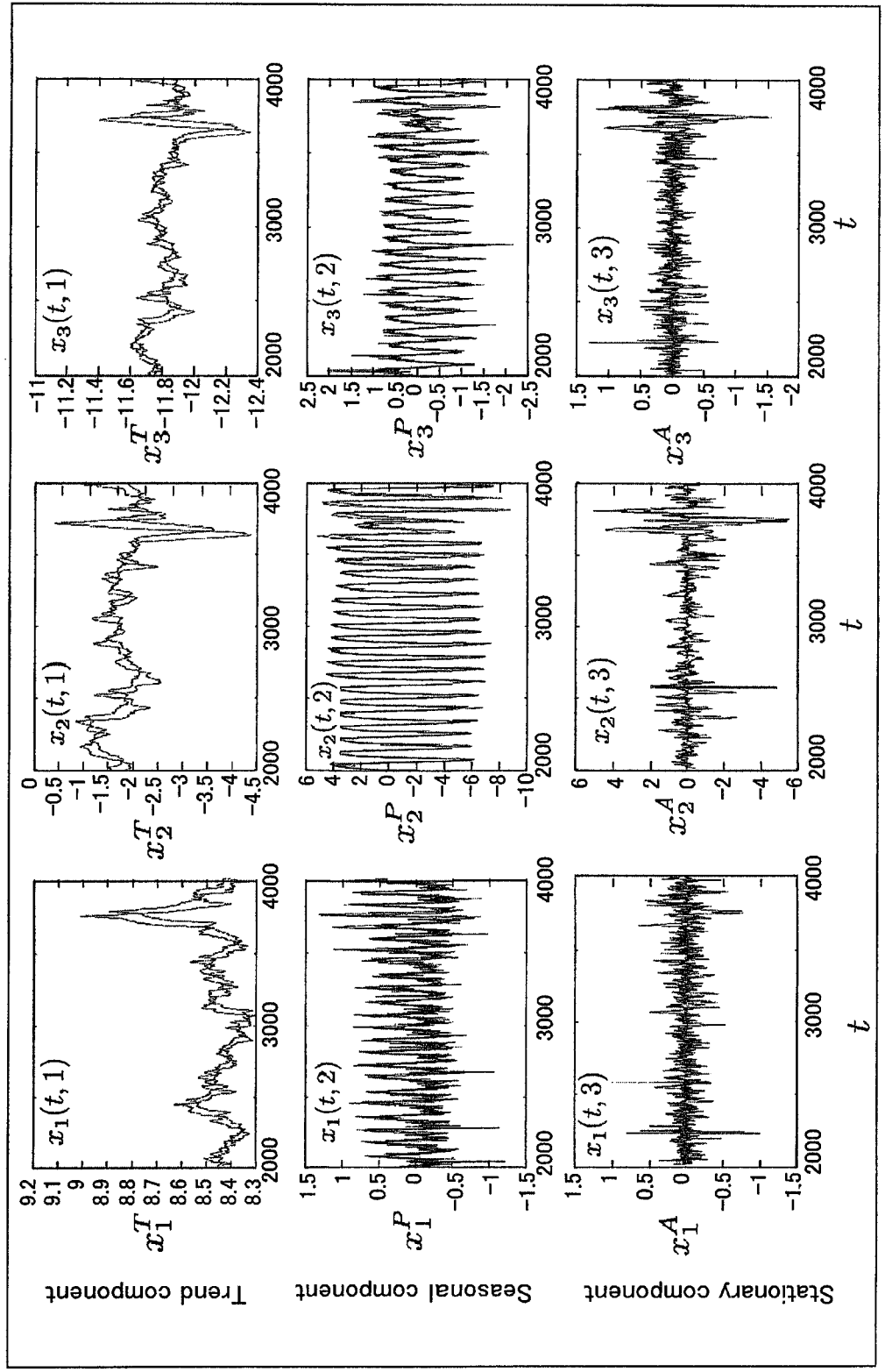
FIG. 15 is a view illustrating actual measurement values of a target time series on sub models regarding the axial components illustrated in FIG. 14 and prediction values for the actual measurement values.
Figures 16A, 16B, 16C:
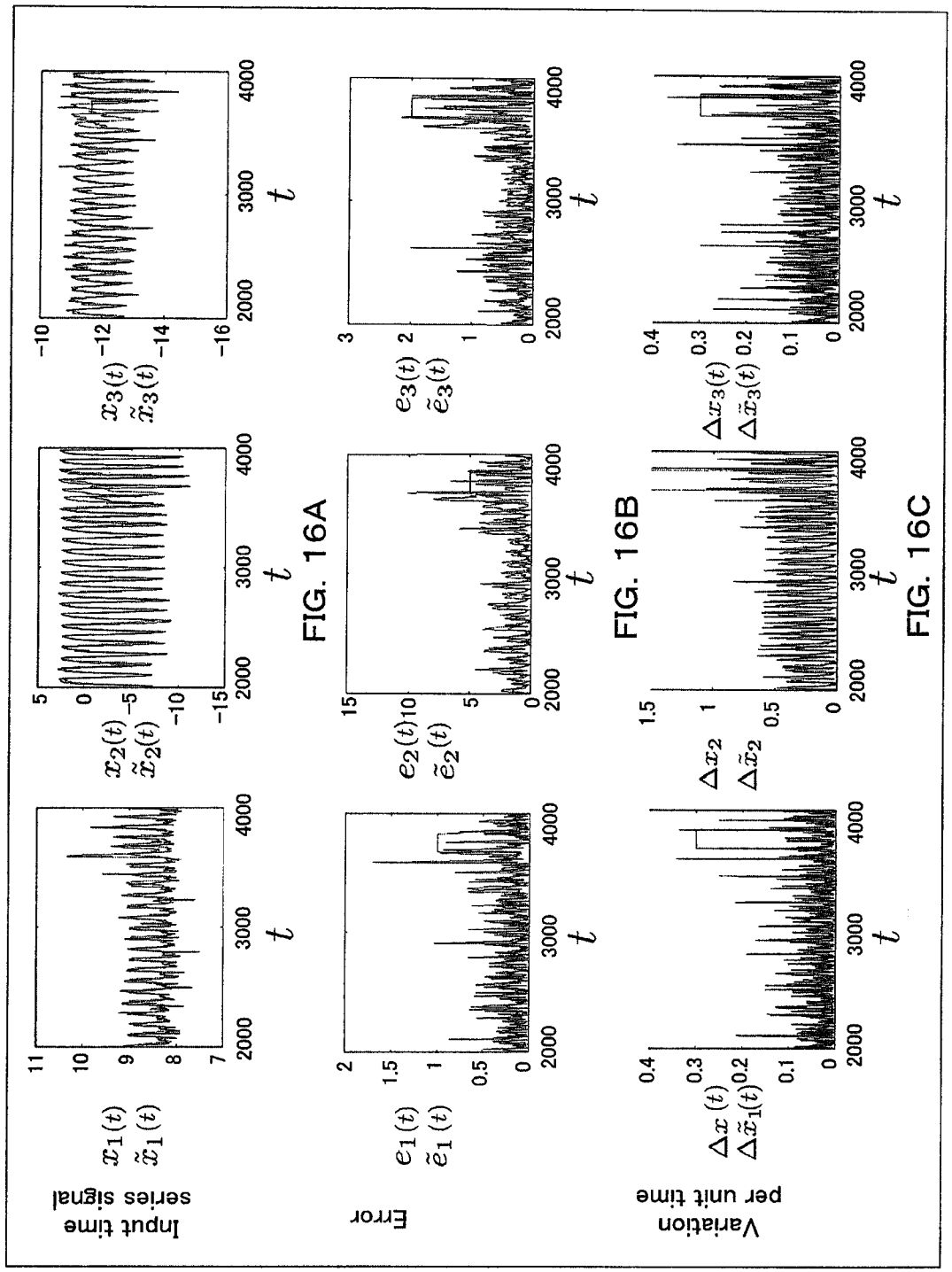
FIG. 16A is a view illustrating actual measurement values and prediction values of the axial components illustrated in FIG. 14.
FIGS. 16B and 16C are views illustrating prediction accuracy estimation information by the prediction accuracy estimation section 16.
Figure 17:
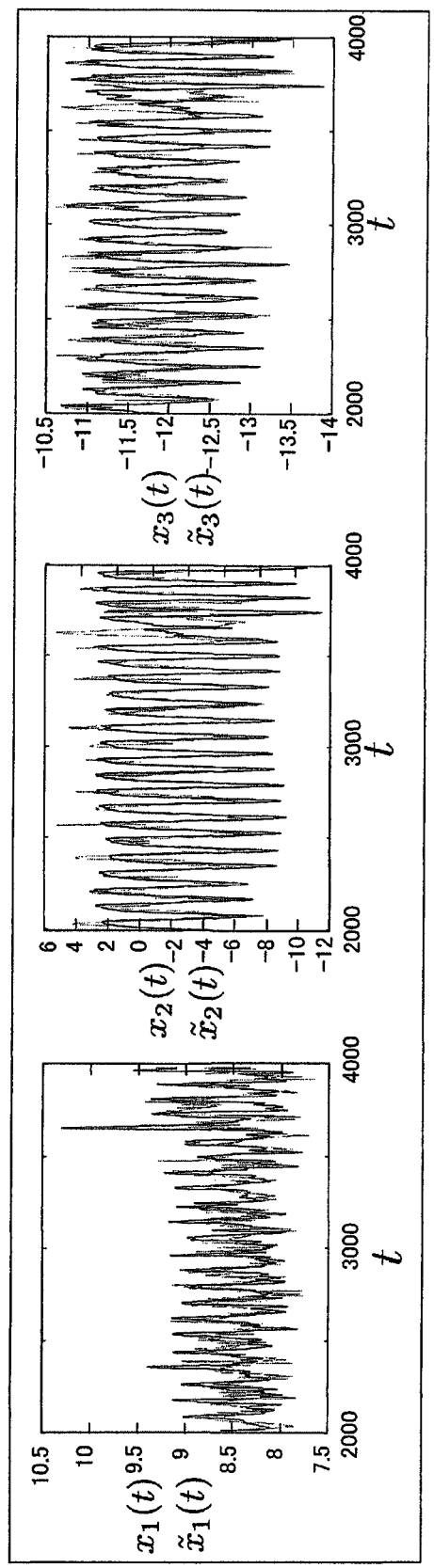
FIG. 17 is a view illustrating actual measurement values of the signal components regarding the axial components illustrated in FIG. 14 and the prediction values by a conventional method.

In the present example, a trend component was separated by calculating a moving average of the input time series signal in the length of the cycle, and the residual time series signal was separated into a seasonal component and other stationary components by calculating a difference of the value delayed by time of the length of the cycle from the residual time series signal. A result when a value of a time series signal of each component as a time series signal after filter processing used as an object of the sub models 111-1 to 111-S (S=3) later by 30 steps [L=30 (approximately one second)] is illustrated in FIG. 15, and a result when an input time series signal is predicted as a synthesis of the outputs is illustrated in FIG. 16A. Here, a blue line corresponds to an actually measured value and a red line corresponds to a result of the prediction, and $x_j^T, x_j^P, x_j^A$, j=1, 2, 3 in FIG. 15 represent sub time series corresponding to a trend component, a seasonal component and a stationary component of jth directional direction data, respectively. For comparison, also a result when the input time series signal was predicted using a conventional general SARIMA mode is illustrated in FIG. 17. Here, a green line corresponds to a result of prediction with an ARMA model. It is to be noted that, in the figures, the axis of abscissa is restricted to an interval of 2000 steps through 4000 steps so that it can be visually observed well.

From the result of FIG. 15, it can be recognized that the accuracy of the prediction for the seasonal component is good in comparison with the prediction accuracy for the tread component and the stationary component. In the present example, the prediction accuracy estimation section 16 detects this situation by evaluation of actual results of prediction in the past, and sets the prediction model of the trend component as a zero-order hold model and produces model design information wherein the ratio of the result of the prediction of the seasonal component to the entire prediction result is increased while the ratio of the prediction result of the stationary component to the entire prediction result is decreased. From the result illustrated in FIG. 16A, it can be recognized that the accuracy of the prediction result of the input time series signal obtained by synthesizing all components is better than that according to the conventional general SARIMA model illustrated in FIG. 17.

The error at the prediction target time estimated by the prediction accuracy estimation section 16 and the time series information of the variation per unit time of the time series signal are illustrated in FIGS. 16B and 16C, respectively. Here, a blue line corresponds to an actually measured value, and a red line corresponds to an estimated value. From those results, it can be recognized that the estimation result by the prediction accuracy estimation section of the present example has a high correlation with the actually measured value.

Figure 18:
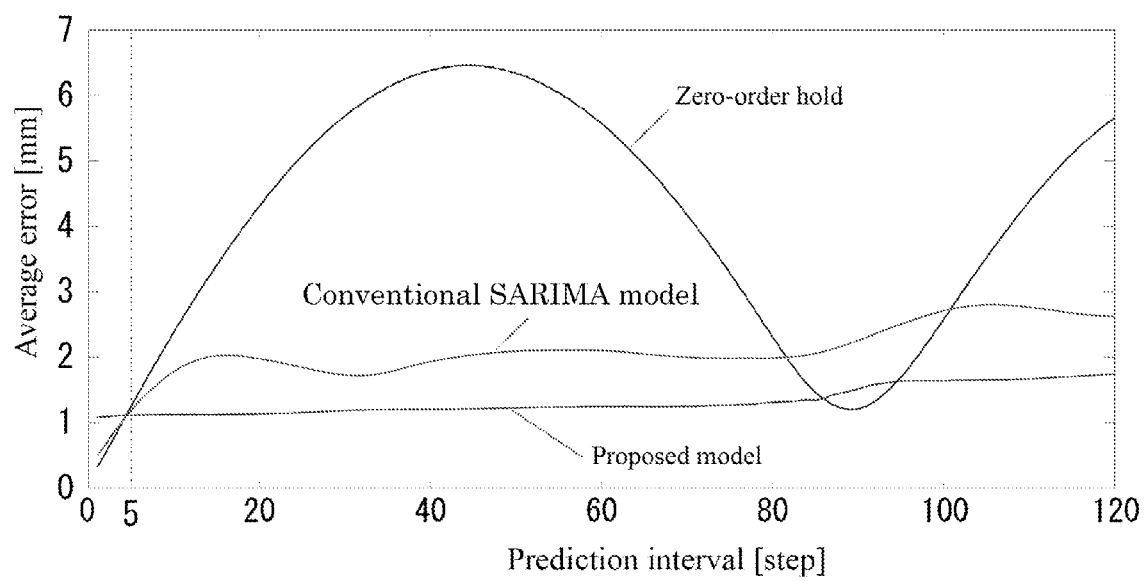
FIG. 18 is a view illustrating a comparison result between a prediction method of the present example and the conventional prediction method.

Further, a variation of the average prediction error where the length L of the prediction period is varied is illustrated in FIG. 18. The axis of abscissa of FIG. 8 indicates the prediction interval (L), and the axis of ordinate indicates the average value of the prediction error. It is to be noted that a result denoted by "Zero-order hold" in the figure represents an error in the case where the latest data of the input time series signal is used as it is as a prediction value. As illustrated in FIG. 18, it can be recognized that, for mid-range prediction more than 5 steps (0.167 seconds), the prediction method of the present example is effective.

In this manner, since the control section 1 of the present embodiment can carry out long term (approximately one second) prediction of the movement of the affected area 260 and estimation of prediction accuracy information of the same, for example, prior to time required for irradiation range formation control of the MLC 210, the MLC 210 can be driven and controlled. As a result, continuous radiation irradiation following up the movement of the affected area 260 can be implemented.

Incidentally, it can be recognized that a specific variation of the dynamics appears in the proximity of the 3700th step of the input time series signal. In the present example, since the prediction accuracy estimation section 16 carries out collation and analysis of result information (error and variation of the time series signal per unit time) of prediction in the past corresponding to the latest prediction, such a specific variation of the dynamics can be detected from the fact that the error and the estimated value of the variation of the time series signal per unit time exhibit assumed maximum values (the outputs at the relevant portions of FIGS. 16B and 16C are saturated). In particular, in the case where the specific variation of the dynamics continues for a long period and radiation irradiation by accurate prediction and follow-up of the movement of the affected area 260 are difficult, it is possible to stop the irradiation of the radiation based on the detection information thereby to prevent irradiation upon normal cells other than those of the affected area 260.

From the results described above, it can be recognized that the method of the present example that "an arbitrary time series signal whose principal component is cycle time-variable seasonal dynamics is used to synthesize a plurality of sub models taking an influence of the cycle time variation into consideration and based on information of a prediction result in the past to carry out prediction and estimate the accuracy of the prediction" is effective.

Further, also it is possible for the cycle fluctuation analysis section 12 of the present example to carry out processes in the case where a plurality of values are set arbitrarily for $$C_j(t_c, k) = \begin{cases} 0 & \ldots \text{if } t_c < 2\max(P_j) \\ \dfrac{\sum_{l=1}^{\max(P_j)} (y_j(t_c, 0, l) - \bar{y}_j(t_c, 0))(y_j(t_c, k, l) - \bar{y}_j(t_c, k))}{\sqrt{\sum_{l=1}^{\max(P_j)} (y_j(t_c, 0, l) - \bar{y}_j(t_c, 0))^2 \sum_{l=1}^{\max(P_j)} (y_j(t_c, k, l) - \bar{y}_j(t_c, k))^2}} & \ldots \text{otherwise} \end{cases}$$ [Expression 81]

$$y_j(t_c, k, l) \equiv x_j(t_c - \max(P_j) + l - k)$$

$$\bar{y}_j(t_c, k) \equiv \frac{1}{\max(P_j)} \sum_{l=1}^{\max(P_j)} x(t_c, k, l)$$

and $\max(P_j)$ in the process $\bar{y}_j(t_c, k)$ of the correlation analysis section 121 simultaneously and in parallel.

This signifies that the correlation analysis section 121 sets a plurality of calculation expressions or data ranges arbitrarily for correlation analysis and calculates $T^L(t_c)$, $C_{T^L}(t_c)$ and $$\{\Delta^L P(\tau)\}_{\tau=2\max(P_j)+L}^{t_c} \equiv \{\|\vec{P}(\tau-L,\tau) - P(\tau)\|\}_{\tau=2\max(P_j)+L}^{t_c}$$ [Expression 57]

of the individual settings simultaneously and in parallel.

Further, the prediction accuracy estimation section 16 can use $T^L(t_c)$, $C_{T^L}(t_c)$ and $$\{\Delta^L P(\tau)\}_{\tau=2\max(P_j)+L}^{t_c} \equiv \{\|\vec{P}(\tau-L,\tau) - P(\tau)\|\}_{\tau=2\max(P_j)+L}^{t_c}$$ [Expression 57]

calculated simultaneously and in parallel by the cycle fluctuation analysis section 12 to estimate more various model design information $I^{model}(t_c)$.

In this instance, for example, the model production section 11 can produce a variety of sub models 111-1 to 111-S which are different from each other not only in the type or the parameter value of the filters and the models but also in combination with the values of $\max(P_j)$ and $\bar{y}_j(t_c, k)$ Here, if the prediction method of the present example before the improvement described above wherein a plurality of values are set for $\max(P_j)$ and $\bar{y}_j(t_c, k)$ to diversify the sub models is applied is referred to as "prediction method (1) of the present example" and the prediction method of the present example after the improvement described above is applied is referred to as "prediction method (2) of the present example", then the relationship between the prediction interval length and the prediction error is such as illustrated in FIG. 31. As illustrated in FIG. 31, it can be recognized that the prediction method (1) of the present example is effective in comparison with a seasonal adjustment index soothing method or a prediction method based on a SARIMA model which are examples of a conventional prediction method, and further, the prediction method (2) of the present example is more effective than the prediction method (1) of the present example.

[2] Others

It is to be noted that the functions as the control section 1 described hereinabove may be implemented by a computer (including a CPU, an information processing apparatus, and various terminals) executing a predetermined application program (signal processing program).

In particular, the program described above is a signal processing program for causing, in the control section 1 for predicting a value of an input time series signal after predetermined time, a computer to implement the above-described prediction function, the signal processing program causing the computer to implement a cycle fluctuation analysis function for assuming a certain component of an input time series signal as a time series signal whose cycle varies with respect to time to carry out a correlation analysis between part of the input time series signal and the input time series signal, estimating a cycle fluctuation of the input time series signal and reliability of the cycle fluctuation using a result of the correlation analysis, predicting a cycle of the input time series signal after predetermined time using the cycle fluctuation and the reliability of the cycle fluctuation and calculating, using the result of the correlation analysis and the predicted cycle, in-phase time information which represents time of the input time series signal whose phase becomes same as a phase of the input time series signal after the predetermined time and the reliability of the in-phase time information, a prediction accuracy estimation function for estimating model design information for predicting a value of the input time series signal after the predetermined time and accuracy of the prediction of the value of the input time series signal after the predetermined time based on the model design information using the input time series signal, the time series information of a variation per unit time of the input time series signal and the in-phase time information and reliability of the in-phase time information calculated by the cycle fluctuation analysis function, and a model production function for producing, using the input time series signal, the in-phase time information and the reliability of the in-phase time information calculated by the cycle fluctuation analysis function and the model design information estimated by the prediction accuracy estimation function, a prediction model for predicting the value of the input time series signal after the predetermined time and predicting and outputting the value of the input time series signal after the predetermined time using the prediction model.

Further, the program described above can be provided in a form in which it is recorded on or in a computer-readable recording medium such as, for example, a flexible disk, a CD (CD-ROM, CD-R, CD-RW or the like) or a DVD (DVD-ROM, DVD-RAM, DVD-R, DVD-RW, DVD+R, DVD+RW or the like). In this instance, a computer can read the signal processing program from the recording medium, transfer and store the signal processing program to and into an internal storage device or an external storage device and then use the signal processing program. Or, the program may be recorded on a storage device (recording medium) such as, for example, a magnetic disk, an optical disk or a magneto-optical disk such that it is provided from the storage device to a computer through a communication line.

Here, the computer is a concept including hardware and an OS (operating system) and signifies hardware which operates under the control of the OS. Further, in such a case that an OS is unnecessary and hardware can be operated solely by an application program, the hardware itself corresponds to a computer. The hardware includes at least a microprocessor such as a CPU and means for reading a computer program recorded in or on a recording medium.

An application program as the signal processing program described above includes program codes for causing such a computer as described above to implement the functions as the control section 1. Further, some of the functions may be implemented not by an application program but by an OS.

It is to be noted that also it is possible to utilize, as the recording medium as the present embodiment, various computer-readable media such as an IC card, a ROM cartridge, a magnetic tape, a punched card, an internal storage device of a computer (a memory such as a RAM or a ROM), an external storage device, a printed matter on which codes such as bar codes are printed and so forth in addition to a flexible disk, a CD, a DVD, a magnetic disk, an optical disk and a magneto-optical disk described hereinabove.

Further, the configurations and the processes of the radiotherapy apparatus and the control section 1 described hereinabove may be selectively used as occasion demands or may be combined suitably.

For example, while, in the examples described hereinabove, the prediction accuracy estimation section 16 uses information regarding a calculation process of a value of an input time series signal after predetermined time, which is outputted from the model production section 11, to set model design information, also it is possible to omit this estimation process.

Further, while, in the examples described hereinabove, an input time series signal is separated into a trend component, a seasonal component and a stationary component and a prediction model is applied to each of them to carry out prediction of the input time series signal, one of the components may be selectively separated from an input time series signal and used for the prediction process.

For example, similar effects to those described hereinabove can be obtained even if only a seasonal component which has a periodicity stronger than the other signal components involved in an input time series signal is separated to apply a predetermined prediction model.

Also it is possible to apply the signal processing method of the present example, for example, to a system which predicts the height of a wave or a position fluctuation arising from the beat of the heart. For example, by predicting a position fluctuation arising from the beat of the heart by the signal processing method described hereinabove, it is possible to implement a system which issues a warning with regard to by what degree the beat of the heart is displaced from that in a normal state (such as arrhythmia).

Furthermore, also it is possible to apply the signal processing method of the present example to power demand forecast, prediction of the communication amount of the Internet or the server load and so forth.

As described in detail above, according to the present invention, an input time series signal at an affected area position can be predicted accurately and for a longer period of time in comparison with that in an alternative case in which an autoregressive model is applied simply to an input time series signal obtained using an observation signal of an affected area position to carryout prediction as in the prior art. Accordingly, it is possible to implement radiation irradiation which follows up a movement of the affected area position and the present invention is considered very useful in the field of the radiation irradiation.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments have been described in detail, it should be understood that the various changes, substitutions, and alterations could be made hereto without departing from the spirit and scope of the invention.

What is claimed is:

1. A radiotherapy apparatus for irradiating a radiation on an affected area of a patient, the radiotherapy apparatus comprising:
   a radiation generator configured to generate the radiation;
   a measure configured to measure a position of the affected area; and
   a signal processing apparatus comprising:
      a cycle fluctuation analyzer configured to assume an input time series signal, which represents values at respective time points until a first time point, as a time series signal whose cycle length, which is a length of a cycle, varies with respect to time to carry out a correlation analysis between part of the input time series signal and the input time series signal, calculate multiple cycle lengths, which are respectively at different time points, as a cycle length fluctuation of the input time series signal and reliability of the cycle length fluctuation using a result of the correlation analysis, predict a cycle length of the time series signal until a second time point after the first time point using the cycle length fluctuation and the reliability of the cycle length fluctuation and calculate, using the result of the correlation analysis and the predicted cycle length, in-phase time information, which represents a time point before the second time point in the input time series signal, and reliability of the in-phase time information, a phase at the time point in the input time series signal becoming same as a phase at the second time point in the time series signal;
      a prediction accuracy estimator configured to estimate model design information for predicting a value of the time series signal at the second time point and accuracy of the prediction of the value of the time series signal at the second time point using the input time series signal, the time series information of a variation per unit time of the value and the in-phase time information and the reliability of the in-phase time information calculated by said cycle fluctuation analyzer, the accuracy being based on the estimated model design information; and
      a model producer configured to produce, using the input time series signal, the in-phase time information and the reliability of the in-phase time information calculated by said cycle fluctuation analyzer and the model design information estimated by said prediction accuracy estimator, a prediction model for predicting the value of the time series signal at the second time point and predict and output the value of the time series signal at the second time point using the prediction model, wherein
   said signal processing apparatus is adapted to predict a position of the affected area at the second time point and estimate accuracy information of the prediction position using, as the input time series signal, a time series signal regarding the position of the affected area measured by said measure.

2. The radiotherapy apparatus according to claim 1, wherein said prediction accuracy estimator estimates the model design information using information outputted from said model producer regarding a calculation process of the value of the time series signal at the second time point.

3. The radiotherapy apparatus according to claim 1, wherein said cycle fluctuation analyzer includes:
   a correlation analyzer configured to carry out a correlation analysis between part of the input time series signal and the input time series signal;
   a cycle estimator configured to estimate the cycle length fluctuation and the reliability of the cycle length fluctuation using a result of the analysis by said correlation analyzer;
   a cycle predictor configured to predict the cycle length of the time series signal until the second time point after the first time point using the cycle length fluctuation and the reliability of the cycle length fluctuation estimated by said cycle estimator; and
   an in-phase time estimator configured to estimate the in-phase time information and the reliability of the in-phase time information using a result of the correlation analysis by said correlation analyzer and the cycle length predicted by said cycle predictor.

4. The radiotherapy apparatus according to claim 1, wherein
   said model producer produces the prediction model using a plurality of sub models whose structures or characteristics are different from each other.

5. The radiotherapy apparatus according to claim 4, wherein
   said plurality of sub models includes at least one of a SARIMA (Seasonal Auto-Regressive Integrated Moving Average) model, a seasonal adjustment index smoothing method model, a non-linear ARIMA (Auto-Regressive Integrated Moving Average) model and a soft computing model.

6. The radiotherapy apparatus according to claim 4, wherein
   said model producer changes the sub models using the accuracy of the prediction of the value of the time series signal at the second time point estimated by said prediction accuracy estimator.

7. A method performed by a radiotherapy apparatus for irradiating a radiation on an affected area of a patient, comprising:
   generating the radiation;
   measuring a position of the affected area;
   assuming an input time series signal, which represents values at respective time points until a first time point, as a time series signal whose cycle length, which is a length of a cycle, varies with respect to time to carry out a correlation analysis between part of the input time series signal and the input time series signal, calculating multiple cycle lengths, which are respectively at different time points, as a cycle length fluctuation of the input time series signal and reliability of the cycle length fluctuation using a result of the correlation analysis, predicting a cycle length of the time series signal until a second time point after the first time point using the cycle length fluctuation and the reliability of the cycle length fluctuation and calculating, using the result of the correlation analysis and the predicted cycle length, in-phase time information, which represents a time point before the second time point in the input time series signal, and reliability of the in-phase time information, a phase at the time point in the input time series signal becoming same as a phase at the second time point in the time series signal;

estimating model design information for predicting a value of the time series signal at the second time point and accuracy of the prediction of the value of the time series signal at the second time point using the input time series signal, the time series information of a variation per unit time of the value and the calculated in-phase time information and the calculated reliability of the in-phase time information, the accuracy being based on the estimated model design information; and producing, using the input time series signal, the calculated in-phase time information and the calculated reliability of the in-phase time information and the estimated model design information, a prediction model for predicting the value of the time series signal at the second time point and predicting and outputting the value of the time series signal at the second time point using the prediction model, wherein said method includes predicting a position of the affected area at the second time point and estimating accuracy information of the prediction position using, as the input time series signal, a time series signal regarding the position of the affected area measured by said measure.

8. The radiotherapy apparatus according to claim 1, further comprising:

a collimator section adapted to form an irradiation range of the radiation generated from said radiation generator into a desired shape; and a driving controller configured to calculate, using the position, which is predicted by said signal processing apparatus, of the affected area at the second time point and the accuracy information estimated by said signal processing apparatus, an irradiation position and an irradiation range of the radiation and control and drive said collimator section based on a result of the calculation.

9. The radiotherapy apparatus according to claim 8, further comprising:

a timing controller configured to control a generation timing of the radiation by said radiation generator using the position of the affected area at the second time point and the accuracy information estimated by said signal processing apparatus.

10. The radiotherapy apparatus according to claim 1, further comprising:

a controller configured to control an irradiation timing of the radiation by said radiation generator using the position, which is predicted by said signal processing apparatus, of the affected area at the second time point and the accuracy information estimated by said signal processing apparatus.

11. A non-transitory computer-readable recording medium storing a signal processing program for causing, in a radio radiotherapy apparatus for irradiating a radiation on an affected area of a patient comprising a radiation generator for generating the radiation, a measure for measuring a position of the affected area, and a signal processing apparatus for predicting a value of a time series signal at a second time point after a first time point, a computer to implement a prediction function that is stored, the signal processing program causing the computer to implement:

a cycle fluctuation analysis function for assuming an input time series signal, which represents values at respective time points until the first time point, as the time series signal whose cycle length, which is a length of a cycle, varies with respect to time to carry out a correlation analysis between part of the input time series signal and the input time series signal, calculating multiple cycle lengths, which are respectively at different time points, as a cycle length fluctuation of the input time series signal and reliability of the cycle length fluctuation using a result of the correlation analysis, predicting a cycle length of the time series signal until the second time point using the cycle length fluctuation and the reliability of the cycle length fluctuation and calculating, using the result of the correlation analysis and the predicted cycle length, in-phase time information, which represents a time point before the second time point in the input time series signal, and reliability of the in-phase time information, a phase at the time point in the input time series signal becoming same as a phase at the second time point in the time series signal;

a prediction accuracy estimation function for estimating model design information for predicting a value of the time series signal at the second time point and accuracy of the prediction of the value of the time series signal at the second time point using the input time series signal, the time series information of a variation per unit time of the value and the in-phase time information and the reliability of the in-phase time information calculated by said cycle fluctuation analysis function, the accuracy being based on the estimated model design information; and a model production function for producing, using the input time series signal, the in-phase time information and the reliability of the in-phase time information calculated by said cycle fluctuation analysis function and the model design information estimated by said prediction accuracy estimation function, a prediction model for predicting the value of the time series signal at the second time point and predicting and outputting the value of the time series signal at the second time point using the prediction model, wherein said signal processing apparatus is adapted to predict a position of the affected area at the second time point and estimate accuracy information of the prediction position using, as the input time series signal, a time series signal regarding the position of the affected area measured by said measure.

12. The radiotherapy apparatus according to claim 8, wherein
the driving controller controls and drives said collimator section in such a manner that the irradiation position follows up the position of the affected area.

13. The radiotherapy apparatus according to claim 8, wherein
the driving controller controls at least one of said radiation generator and said collimator section in such a manner that the radiation is not irradiated on the patient in the case that a variation of the input time series signal per unit time is equal to or larger than a predetermined threshold value.

14. The radiotherapy apparatus according to claim 10, wherein
the driving controller controls said radiation generator in such a manner that the radiation is not irradiated on the patient in the case that a variation of the input time series signal per unit time is equal to or larger than a predetermined threshold value.

* * * * *